US012760097B2

(12) United States Patent
Prussak et al.

(10) Patent No.: US 12,760,097 B2
(45) Date of Patent: Oct. 13, 2026

(54) CHIMERIC ANTIGEN RECEPTOR MODIFIED T-CELLS (CAR-T) FOR THE TREATMENT OF HEMATOLOGICAL AND SOLID TUMOR CANCERS

(71) Applicant: The Regents of the University of California, Oakland, CA (US)

(72) Inventors: Charles E. Prussak, Oakland, CA (US); Thomas J. Kipps, Oakland, CA (US); George F. Widhopf, II, Oakland, CA (US); Christopher S. Oh, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 1295 days.

(21) Appl. No.: 17/598,200

(22) PCT Filed: Mar. 26, 2020

(86) PCT No.: PCT/US2020/025069
§ 371 (c)(1),
(2) Date: Sep. 24, 2021

(87) PCT Pub. No.: WO2020/198531
PCT Pub. Date: Oct. 1, 2020

(65) Prior Publication Data

US 2023/0312708 A1 Oct. 5, 2023

Related U.S. Application Data

(60) Provisional application No. 62/969,569, filed on Feb. 3, 2020, provisional application No. 62/931,103, filed on Nov. 5, 2019, provisional application No. 62/824,080, filed on Mar. 26, 2019.

(51) Int. Cl.

| | |
|---|---|
| ***C07K 16/00*** | (2006.01) |
| ***A61K 40/11*** | (2025.01) |
| ***A61K 40/31*** | (2025.01) |
| ***A61K 40/32*** | (2025.01) |
| ***A61K 40/33*** | (2025.01) |
| ***A61K 40/42*** | (2025.01) |
| ***A61P 35/02*** | (2006.01) |
| ***C07K 14/705*** | (2006.01) |
| ***C07K 16/28*** | (2006.01) |
| ***C12N 5/0783*** | (2010.01) |
| *A61K 39/00* | (2006.01) |

(52) U.S. Cl.
CPC .......... *C07K 16/2803* (2013.01); *A61K 40/11* (2025.01); *A61K 40/31* (2025.01); *A61K 40/32* (2025.01); *A61K 40/33* (2025.01); *A61K 40/421* (2025.01); *A61P 35/02* (2018.01); *C07K 14/7051* (2013.01); *C07K 14/70521* (2013.01); *C07K 14/70578* (2013.01); *C12N 5/0636* (2013.01); *C12N 5/0646* (2013.01); *A61K 2039/505* (2013.01); *A61K 2239/13* (2023.05); *A61K 2239/21* (2023.05); *A61K 2239/22* (2023.05); *A61K 2239/38* (2023.05); *A61K 2239/48* (2023.05); *C07K 2317/622* (2013.01); *C07K 2319/03* (2013.01)

(58) Field of Classification Search
None
See application file for complete search history.

(56) References Cited

U.S. PATENT DOCUMENTS

| | | | |
|---|---|---|---|
| 2013/0266551 A1 | 10/2013 | Campana et al. | |
| 2016/0208018 A1* | 7/2016 | Chen | A61P 35/00 |
| 2017/0283497 A1 | 10/2017 | Schiffer-Mannioui | |
| 2017/0333480 A1 | 11/2017 | Cooper et al. | |
| 2018/0066063 A1 | 3/2018 | Kipps et al. | |
| 2018/0125892 A1 | 5/2018 | Brannetti et al. | |
| 2018/0265593 A1 | 9/2018 | Chen et al. | |
| 2018/0369406 A1 | 12/2018 | Lannutti et al. | |

FOREIGN PATENT DOCUMENTS

| | | |
|---|---|---|
| WO | WO-03/080672 A1 | 10/2003 |
| WO | WO-2014/031174 A1 | 2/2014 |
| WO | WO-2016/115559 A1 | 7/2016 |
| WO | WO-2017/127664 A1 | 7/2017 |
| WO | WO-2021/102055 A1 | 5/2021 |

OTHER PUBLICATIONS

Choi et al. (Jun. 2015). "Pre-clinical Specificity and Safety of UC-961, a First-In-Class Monoclonal Antibody Targeting ROR1," *Clinical Lymphoma Myeloma and Leukemia* 15(0):S167-S169.
International Search Report mailed on Sep. 24, 2020, for PCT Application No. PCT/US2020/025069, filed Mar. 26, 2020, 4 pages.
Written Opinion mailed on Sep. 24, 2020, for PCT Application No. PCT/US2020/025069, filed Mar. 26, 2020, 11 pages.
Extended European Search Report mailed on Sep. 30, 2022 for EP Patent Application No. 20778519.7, 11 pages.
Hudecek, M. et al. (Jun. 15, 2013, e-published Apr. 25, 2013). "Receptor affinity and extracellular domain modifications affect tumor recognition by ROR1-specific chimeric antigen receptor T cells," *Clin Cancer Res* 19(12):3153-3164.

(Continued)

*Primary Examiner* — Meera Natarajan
(74) *Attorney, Agent, or Firm* — Mintz Levin Cohn Ferris Glovsky and Popeo. P.C

(57) ABSTRACT

Provided herein is a chimeric antigen receptor (CAR) and CAR-expressing immune cells that target human RORI expressed aberrantly on a tumor cancers. Described herein are chimeric antigen receptors that target human ROR-1, cell compositions expressing the chimeric antigen receptors, and methods and uses of the chimeric antigen receptors and/or the cell compositions. The chimeric antigen receptors described herein can be expressed by the T lymphocytes isolated from an individual afflicted with cancer and re-administered to the individual.

21 Claims, 31 Drawing Sheets

Specification includes a Sequence Listing.

(56) References Cited

OTHER PUBLICATIONS

Guedan, S. et al. (Dec. 31, 2018). "Engineering and Design of Chimeric Antigen Receptors," *Mol Ther Methods Clin Dev* 12:145-156.
Rudikoff, S. et al. (Mar. 1982). "Single amino acid substitution altering antigen-binding specificity," PNAS USA 79(6):1979-1983.
Tamura, M. et al. (Feb. 1, 2000). "Structural correlates of an anticarcinoma antibody: identification of specificity-determining residues (SDRs) and development of a minimally immunogenic antibody variant by retention of SDRs only," *J Immunol* 164(3):1432-1441.

* cited by examiner

CHIMERIC ANTIGEN RECEPTOR MODIFIED T-CELLS (CAR-T) FOR THE TREATMENT OF HEMATOLOGICAL AND SOLID TUMOR CANCERS

CROSS-REFERENCES TO RELATED APPLICATIONS

This application is the national stage filing which claims the benefit under 35 U.S.C. § 371 of International Application No. PCT/US20/25069 filed Mar. 26, 2020, which claims priority to U.S. Provisional Application No. 62/824,080, filed Mar. 26, 2019, U.S. Provisional Application No. 62/931,103, filed Nov. 5, 2019 and U.S. Provisional Application No. 62/969,569, filed Feb. 3, 2020, which are hereby incorporated by reference in their entirety and for all purposes.

SEQUENCE LISTING

The Sequence Listing written in file 048537-623NO1US_SL_ST25.txt, created on Nov. 21, 2025, 71,674 bytes, machine format IBM-PC, MS-Windows operating system, is hereby incorporated by reference.

BACKGROUND

The utility of chimeric antigen receptor modified T-cells (CAR-T) to treat cancer has been demonstrated in a number of clinical studies including the approval by the FDA of two of these products for the treatment of pediatric acute lymphocytic leukemia and transformed non-Hodgkins Lymphoma. These successful CAR-Ts, tisagenlecleucel and axicabtagene ciloleucel developed by Novartis and Kite Pharmaceuticals, respectively, are autologous products that target the B-cell antigen CD-19. Although they target the same cancer antigen, the CAR-T products they created have distinct structures and production methods. Along with these approved products, many additional CAR-T clinical studies, sponsored by a variety of domestic and foreign pharmaceutical and biotech companies, are ongoing that target the same antigen and like the approved products, involve unique structures and manufacturing methods. Along with the CD-19 targeting CARs, a number of additional cancer-associated antigens are targeted in ongoing clinical studies by CARs variably employing unique structures, T-cell targets, activation and manufacturing methods and patient pretreatment protocols. The large number of clinical studies employing these differing agents and approaches highlight the complex pharmacology of CAR-Ts. The compositions and methods provided herein address current needs in the art for ROR-1 specific CARs and their use in therapeutics and diagnostics.

SUMMARY

Described herein are chimeric antigen receptors that target human ROR-1, cell compositions expressing the chimeric antigen receptors, and methods and uses of the chimeric antigen receptors and/or the cell compositions. The chimeric antigen receptors described herein can be expressed by the T lymphocytes isolated from an individual afflicted with cancer and re-administered to the individual. Administration of T cells expressing the CARs described herein serves as an effective therapeutic treatment for cancers that express ROR-1. Further, described herein are optimized intracellular signaling domains and membrane spacers that result in improved function of anti-ROR-1 CAR-T cells.

Aspects disclosed herein provide a chimeric antigen receptor targeting ROR-1. The chimeric receptor comprises i) an antigen binding region, wherein the antigen binding region specifically binds ROR-1 and wherein the antigen binding region comprises a light chain variable domain and a heavy chain variable domain, ii) a spacer domain, wherein the spacer domain comprises a spacer of between 10 and 240 amino acids in length, iii) a transmembrane domain, and iv) an intracellular domain. The light chain variable domain comprises a CDR L1 as set forth in SEQ ID NO:43, a CDR L2 as set forth in SEQ ID NO:44 and a CDR L3 as set forth in SEQ ID NO:45, and the heavy chain variable domain comprises a CDR H1 as set forth in SEQ ID NO: 46, a CDR H2 as set forth in SEQ ID NO:47, and a CDR H3 as set forth in SEQ ID NO: 48. Alternatively, the light chain variable domain comprises a CDR L1 as set forth in SEQ ID NO: 49, a CDR L2 as set forth in SEQ ID NO:50 and a CDR L3 as set forth in SEQ ID NO: 51, and the heavy chain variable domain comprises a CDR H1 as set forth in SEQ ID NO: 52, a CDR H2 as set forth in SEQ ID NO:53, and a CDR H3 as set forth in SEQ ID NO:54.

In some instances, the light chain variable domain is coupled to N-terminus or C-terminus of the heavy chain variable domain. In some embodiments, the light chain variable domain is covalently coupled to the heavy chain variable domain through a polypeptide linker. In some embodiments, the polypeptide linker comprises an amino acid sequence of SEQ ID NO:24. In some embodiments, the light chain variable domain comprises an amino acid sequence at least about 90%, 95%, 97%, 98%, 99%, or 100% identical to SEQ ID NO:21. In some embodiments, the light chain variable domain consists of an sequence of SEQ ID NO:21. In some embodiments, the heavy chain variable domain comprises an amino acid sequence at least about 90%, 95%, 97%, 98%, 99%, or 100% identical to SEQ ID NO:27. In some embodiments, the heavy chain variable domain consists of an amino acid sequence of SEQ ID NO:27. In some embodiments, the light chain variable domain comprises an amino acid sequence at least about 90%, 95%, 97%, 98%, 99%, or 100% identical to SEQ ID NO:19. In some embodiments, the light chain variable domain consists of an amino acid sequence of SEQ ID NO:19. In some embodiments, the light chain variable domain comprises an amino acid sequence at least about 90%, 95%, 97%, 98%, 99%, or 100% identical to SEQ ID NO:20. In some embodiments, the light chain variable domain consists of an amino acid sequence of SEQ ID NO:20. In some embodiments, the heavy chain variable domain comprises an amino acid sequence at least about 90%, 95%, 97%, 98%, 99%, or 100% identical to SEQ ID NO:25. In some embodiments, the heavy chain variable domain consists of the sequence of SEQ ID NO:25. In some embodiments, the heavy chain variable domain comprises an amino acid sequence at least about 90%, 95%, 97%, 98%, 99%, or 100% identical to SEQ ID NO:26. In some embodiments, the heavy chain variable domain consists of the sequence of SEQ ID NO:26.

In some instances, the spacer domain comprises an antibody domain. In some embodiments, the antibody domain comprises an immunoglobulin hinge domain, an immunoglobulin constant heavy chain 3 (CH3) domain, an immunoglobulin constant heavy chain 2 (CH2) domain, or a combination thereof. In some embodiments, the antibody domain consists of the immunoglobulin hinge domain. In some embodiments, the antibody domain consists of the immunoglobulin hinge domain and the immunoglobulin constant heavy chain 3 (CH3) domain. In some embodiments, the antibody domain consists of the immunoglobulin hinge domain, the immunoglobulin constant heavy chain 3 (CH3) domain and the immunoglobulin constant heavy chain 2 (CH2) domain.

In some instances, the spacer domain is between 14 and 120 amino acids in length. In some embodiments, the spacer domain comprises an amino acid sequence of SEQ ID NO:29, SEQ ID NO:41 or SEQ ID NO:42. In some embodiments, the spacer domain consists of an amino acid sequence of SEQ ID NO:29, SEQ ID NO:41 or SEQ ID NO:42.

In some instances, the transmembrane domain comprises a CD8α transmembrane domain, a CD28 transmembrane domain, a CD4 transmembrane domain, a CD3ζ transmembrane domain, or any combination thereof. In some embodiments, transmembrane domain is a CD28 transmembrane domain. In some embodiments, the CD28 transmembrane domain comprises an amino acid sequence of SEQ ID NO:32. In some embodiments, the CD28 transmembrane domain consists of an amino acid sequence of SEQ ID NO:32.

In some instances, the intracellular domain comprises an intracellular co-stimulatory signaling domains, an intracellular T-cell signaling domains, or a combination thereof. In some embodiments, the intracellular co-stimulatory signaling domains is a 4-1BB intracellular co-stimulatory signaling domain, a CD28 intracellular co-stimulatory signaling domain, a ICOS intracellular co-stimulatory signaling domain, an OX-40 intracellular co-stimulatory signaling domain, or any combination thereof. In some embodiments, the 4-1BB intracellular co-stimulatory signaling domain comprises an amino acid sequence of SEQ ID NO:33. In some embodiments, the 4-1BB intracellular co-stimulatory signaling domain consists of an amino acid sequence of SEQ ID NO:33. In some embodiments, the intracellular costimulatory signaling domain comprises a CD28 intracellular co-stimulatory signaling domain and a 4-1BB intracellular co-stimulatory signaling domain. In some embodiments, the intracellular costimulatory signaling domain comprises an intracellular T-cell signaling domain. In some embodiments, the intracellular T-cell signaling domain is a CD3ζ intracellular T-cell signaling domain. In some embodiments, the CD3ζ intracellular T-cell signaling domain comprises an amino acid sequence of SEQ ID NO:34. In some embodiments, the CD3 intracellular T-cell signaling domain consists of an amino acid sequence of SEQ ID NO:34. In some embodiments, the chimeric antigen receptor binds to a cell expressing ROR-1.

Aspects disclosed herein provide a nucleic acid encoding the chimeric antigen receptor described herein. In some embodiments, the nucleic acid is a viral vector. In some embodiments, the viral vector is a lentiviral vector.

Aspects disclosed herein provide a cell comprising the nucleic acid described herein. Aspects disclosed herein also provide a cell expressing the chimeric antigen receptor described herein. In some embodiments, the cell is a T lymphocyte. In some embodiments, the T lymphocyte is a CD4+ T lymphocyte or a CD8+ T lymphocyte. In some embodiments, the cell is a natural killer cell, a genetically engineered natural killer cell or a CD56+ cell.

Aspects disclosed herein provide a pharmaceutical composition comprising a therapeutically effective amount of the cells described herein and a pharmaceutically acceptable diluent, carrier, or excipient. In some embodiments, the composition is formulated for intravenous injection.

Aspects disclosed herein provide a method of treating cancer in an individual in need thereof by administering to the individual the pharmaceutical composition as described herein. In some embodiments, the cancer comprises a leukemia, a lymphoma, chronic lymphocytic leukemia, adult acute myeloid leukemia, acute lymphoblastic leukemia, a mantle cell lymphoma, ovarian cancer, colon cancer, lung cancer, skin cancer, pancreatic cancer, testicular cancer, bladder cancer, uterine cancer, prostate cancer, or adrenal cancer. In some embodiments, the method further comprises administering cirmtuzumab to the individual. In some embodiments, the cirmtuzumab and the pharmaceutical composition are administered separately.

Aspects disclosed herein provide a method of treating cancer in an individual in need thereof or the use of the chimeric antigen receptor or chimeric antigen receptor T cells for a method of treating cancer in an individual, wherein the cancer is a CD19 negative cancer or has reduced CD19 expression as a result of a prior treatment that targets CD19. In some embodiments, the individual has previously been treated with a therapeutic that targets CD19. In some embodiments, the therapeutic that targets CD19 is an antibody that binds to CD19. In some embodiments, the therapeutic that targets CD19 is a chimeric antigen receptor T cell that targets CD19. In some embodiments, the therapeutic that targets CD19 is a chimeric antigen receptor NK cell that targets CD19. In some embodiments, the cancer expresses ROR1.

Aspects disclosed herein provide a pharmaceutical composition as described herein for use in a method of treating cancer in an individual. In some embodiments, the cancer comprises a leukemia, a lymphoma, chronic lymphocytic leukemia, adult acute myeloid leukemia, acute lymphoblastic leukemia, a mantle cell lymphoma, ovarian cancer, colon cancer, lung cancer, skin cancer, pancreatic cancer, testicular cancer, bladder cancer, uterine cancer, prostate cancer, or adrenal cancer.

DETAILED DESCRIPTION

Definitions

Figure 1A:
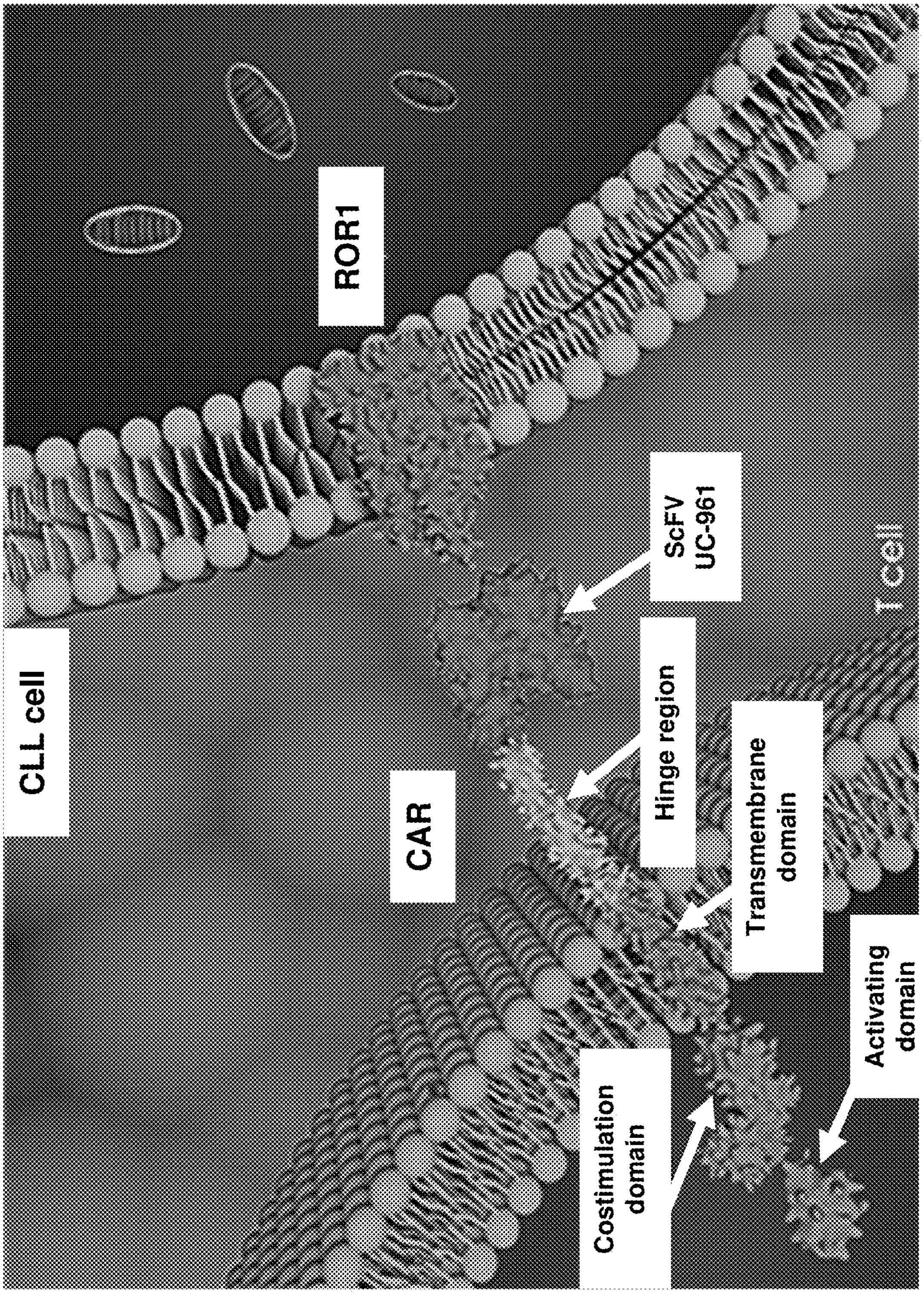
FIG. 1A illustrates an anti-ROR-1 CAR-T cell interacting with an ROR-1 expressing chronic lymphocytic leukemia (CLL) cell.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Unless defined otherwise, technical and scientific terms used herein have the same meaning as commonly understood by a person of ordinary skill in the art. See, e.g., Singleton et al., Dictionary Of Microbiology And Molecular Biology 2nd ed., J. Wiley & Sons (New York, NY 1994); Sambrook et al., Molecular Cloning, A Laboratory Manual, Cold Springs Harbor Press (Cold Springs Harbor, NY 1989). Any methods, devices and materials similar or equivalent to those described herein can be used in the practice of this invention. The following definitions are provided to facilitate understanding of certain terms used frequently herein and are not meant to limit the scope of the present disclosure.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers to nucleic acids that have the same basic chemical structure as a naturally occurring nucleic acid. Such analogues have modified sugars and/or modified ring substituents, but retain the same basic chemical structure as the naturally occurring nucleic acid. A nucleic acid mimetic refers to chemical compounds that have a structure that is different from the general chemical structure of a nucleic acid, but that functions in a manner similar to a naturally occurring nucleic acid. Examples of such analogues include, without limitation, phosphorothiolates, phosphoramidates, methyl phosphonates, chiral-methyl phosphonates, 2-O-methyl ribonucleotides, and peptide-nucleic acids (PNAs).

The term "gene" means the segment of DNA involved in producing a protein; it includes regions preceding and following the coding region (leader and trailer) as well as intervening sequences (introns) between individual coding segments (exons). The leader, the trailer, as well as the introns, include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules may be detected by standard PCR or Northern blot methods well known in the art. See, Sambrook et al., 1989 *Molecular Cloning: A Laboratory Manual,* 18.1-18.88.

Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell.

The terms "transfection", "transduction", "transfecting" or "transducing" are used interchangeably throughout and are defined as a process of introducing a nucleic acid molecule or a protein to a cell. Nucleic acids are introduced to a cell using non-viral or viral-based methods. The nucleic acid molecules may be gene sequences encoding complete proteins or functional portions thereof. Non-viral methods of transfection include any appropriate transfection method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection, and electroporation. In some embodiments, the nucleic acid molecules are introduced into a cell using electroporation following standard procedures well known in the art. For viral-based methods of transfection any useful viral vector may be used in the methods described herein. Examples for viral vectors include, but are not limited to retroviral, adenoviral, lentiviral and adeno-associated viral vectors. In some embodiments, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) *Gene Therapy* 8:1-4 and Prochiantz (2007) *Nat. Methods* 4:119-20.

The term "plasmid" or "expression vector" refers to a nucleic acid molecule that encodes for genes and/or regulatory elements necessary for the expression of genes. Expression of a gene from a plasmid can occur in cis or in trans. If a gene is expressed in cis, gene and regulatory elements are encoded by the same plasmid. Expression in trans refers to the instance where the gene and the regulatory elements are encoded by separate plasmids.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "numbered with reference to" or "corresponding to," when used in the context of the numbering of a given amino acid or polynucleotide sequence, refer to the numbering of the residues of a specified reference sequence when the given amino acid or polynucleotide sequence is compared to the reference sequence. An amino acid residue in a protein "corresponds" to a given residue when it occupies the same essential structural position within the protein as the given residue. One skilled in the art will immediately recognize the identity and location of residues corresponding to a specific position in a protein (e.g., ROR-1) in other proteins with different numbering systems. For example, by performing a simple sequence alignment with a protein (e.g., ROR-1) the identity and location of residues corresponding to specific positions of the protein are identified in other protein sequences aligning to the protein. For example, a selected residue in a selected protein corresponds to glutamic acid at position 138 when the selected residue occupies the same essential spatial or other structural relationship as a glutamic acid at position 138. In some embodiments, where a selected protein is aligned for maximum homology with a protein, the position in the aligned selected protein aligning with glutamic acid 138 is the to correspond to glutamic acid 138. Instead of a primary sequence alignment, a three dimensional structural alignment can also be used, e.g., where the structure of the selected protein is aligned for maximum correspondence with the glutamic acid at position 138, and the overall structures compared. In this case, an amino acid that occupies the same essential position as glutamic acid 138 in the structural model is the to correspond to the glutamic acid 138 residue.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

The term "recombinant" when used with reference, for example, to a cell, a nucleic acid, a protein, or a vector, indicates that the cell, nucleic acid, protein or vector has been modified by or is the result of laboratory methods. Thus, for example, recombinant proteins include proteins produced by laboratory methods. Recombinant proteins can include amino acid residues not found within the native (non-recombinant) form of the protein or can be include amino acid residues that have been modified (e.g., labeled).

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then the to be "substantially identical." This definition also refers to the complement of a test sequence. Optionally, the identity exists over a region that is at least about 50 nucleotides in length, or more preferably over a region that is 100 to 500 or 1000 or more nucleotides in length.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Any methods of alignment of sequences for comparison well known in the art are contemplated. Optimal alignment of sequences for comparison can be conducted, e.g., e.g., by the local homology algorithm of Smith and Waterman (1970) *Adv. Appl. Math.* 2: 482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross-reactive with the antibodies raised against the polypeptide encoded by the second nucleic acid, as described below. Thus, a polypeptide is typically or substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

Antibodies are large, complex molecules (molecular weight of ~150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions come together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-dimensional space to form the actual antibody binding site which docks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs.

An "antibody variant" as provided herein refers to a polypeptide capable of binding to an antigen and including one or more structural domains (e.g., light chain variable domain, heavy chain variable domain) of an antibody or fragment thereof. Non-limiting examples of antibody variants include single-domain antibodies or nanobodies, monospecific Fab2, bispecific Fab2, trispecific Fab3, monovalent IgGs, scFv, bispecific antibodies, bispecific diabodies, trispecific triabodies, scFv-Fc, minibodies, IgNAR, V-NAR, hcIgG, VhH, or peptibodies. A "peptibody" as provided herein refers to a peptide moiety attached (through a covalent or non-covalent linker) to the Fc domain of an antibody. Further non-limiting examples of antibody variants known in the art include antibodies produced by cartilaginous fish or camelids. A general description of antibodies from camelids and the variable regions thereof and methods for their production, isolation, and use may be found in references WO97/49805 and WO 97/49805 which are incorporated by reference herein in their entirety and for all purposes. Likewise, antibodies from cartilaginous fish and the variable regions thereof and methods for their production, isolation, and use may be found in WO2005/118629, which is incorporated by reference herein in its entirety and for all purposes.

The terms "CDR L1", "CDR L2" and "CDR L3" as provided herein refer to the complementarity determining regions (CDR) 1, 2, and 3 of the variable light (L) chain of an antibody. In embodiments, the variable light chain provided herein includes in N-terminal to C-terminal direction a CDR L1, a CDR L2 and a CDR L3. Likewise, the terms "CDR H1", "CDR H2" and "CDR H3" as provided herein refer to the complementarity determining regions (CDR) 1, 2, and 3 of the variable heavy (H) chain of an antibody. In embodiments, the variable light chain provided herein includes in N-terminal to C-terminal direction a CDR L1, a CDR L2 and a CDR L3.

The term "antibody" is used according to its commonly known meaning in the art. Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_{H1}$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

The term "antigen" as provided herein refers to molecules capable of binding to the antibody binding domain provided herein. An "antigen binding domain" as provided herein is a region of an antibody that binds to an antigen (epitope). As described above, the antigen binding domain is generally composed of one constant and one variable domain of each of the heavy and the light chain ($V_L$, $V_H$, $C_L$ and $C_H1$, respectively). The paratope or antigen-binding site is formed on the N-terminus of the antigen binding domain. The two variable domains of an antigen binding domain typically bind the epitope on an antigen.

Antibodies exist, for example, as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to $V_H$-$C_H1$ by a disulfide bond. The F(ab)'2 may be reduced under mild conditions to break the disulfide linkage in the hinge region, thereby converting the F(ab)'2 dimer into an Fab' monomer. The Fab' monomer is essentially the antigen binding portion with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., e.g., single chain Fv) or those identified using phage display libraries (see, e.g., e.g., McCafferty et al., Nature 348:552-554 (1990)).

A single-chain variable fragment (scFv) is typically a fusion protein of the variable regions of the heavy ($V_H$) and light chains ($V_L$) of immunoglobulins, connected with a short linker peptide of 10 to about 25 amino acids. The linker may usually be rich in glycine for flexibility, as well as serine or threonine for solubility. The linker can either connect the N-terminus of the $V_H$ with the C-terminus of the $V_L$, or vice versa.

The epitope of an antibody is the region of its antigen to which the antibody binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 30% but preferably 50%, 75%, 90% or even 99% as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

The term "ROR-1" or "ROR1" as used herein refers to any of the recombinant or naturally-occurring forms of tyrosine kinase-like orphan receptor 1 (ROR-1) or variants or homologs thereof that maintain ROR-1 activity (e.g., within at least 50%, 80%, 90%, 95%, 96%, 97%, 98%, 99% or 100% activity compared to ROR-1). In some aspects, the variants or homologs have at least 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring ROR-1 protein. In embodiments, the ROR-1 protein is substantially identical to the protein identified by Accession No. NP_005003.1 or a variant or homolog having substantial identity thereto. In embodiments, the ROR-1 protein includes the amino acid sequence of SEQ ID NO:55. In embodiments, the ROR-1 protein is the amino acid sequence of SEQ ID NO: 55. In embodiments, the ROR-1 protein includes the amino acid sequence of SEQ ID NO:56. In embodiments, the ROR-1 protein includes the amino acid sequence of SEQ ID NO:57.

The terms "cirmtuzumab", "UC-961", and "99961.1" refer to a humanized monoclonal antibody capable of binding the extracellular domain of the human receptor tyrosine kinase-like orphan receptor 1 (ROR-1). In embodiments, cirmtuzumab is any one of the antibodies or fragments thereof disclosed in U.S. patent application Ser. No. 14/422,519, which is incorporated by reference herein in its entirety and for all purposes.

The term "CD28 transmembrane domain" as provided herein includes any of the recombinant or naturally-occurring forms of the transmembrane domain of CD28, or variants or homologs thereof that maintain CD28 transmembrane activity (e.g. within at least 50%, 80%, 90%, 95%, 96%, 97%, 98%, 99% or 100% activity compared to the CD28 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD28 transmembrane domain polypeptide. In embodiments, the CD28 transmembrane domain is a human CD28 transmembrane domain protein. In embodiments, a variant or mutant of the CD28 transmembrane domain protein includes no more than 5, 4, 3, 2, or 1 deletions compared to the naturally occurring CD28 transmembrane domain protein. In embodiments, a variant or mutant of the CD28 transmembrane domain protein includes no more than 5, 4, 3, 2, or 1 insertions compared to the naturally occurring CD28 transmembrane domain protein. In embodiments, a variant or mutant of the CD28 transmembrane domain protein does not include deletions compared to the naturally occurring CD28 transmembrane domain protein. In embodiments, a variant or mutant of the CD28 transmembrane domain protein does not include insertions compared to the naturally occurring CD28 transmembrane domain protein. In embodiments, a variant or mutant of the CD28 transmembrane domain protein includes substitutions that are conservative substitutions compared to the naturally occurring CD28 transmembrane domain protein. In embodiments, the CD28 transmembrane domain includes all or a portion of the protein as identified by NCBI sequence reference NP_001230006.1, or an isoform or naturally occurring mutant or variant thereof. In embodiments, the CD28 transmembrane domain includes all or a portions of the protein as identified by the NCBI sequence reference NP_001230007.1, or an isoform or naturally occurring mutant or variant thereof. In embodiments, the CD28 transmembrane domain includes all or a portion of the protein as identified by the NCBI sequence reference NP_006130.1, or an isoform or naturally occurring mutant or variant thereof.

The term "CD4 transmembrane domain" as provided herein includes any of the recombinant or naturally-occurring forms of the transmembrane domain of CD4, or variants or homologs thereof that maintain CD4 transmembrane domain activity (e.g. within at least 50%, 80%, 90%, 95%, 96%, 97%, 98%, 99% or 100% activity compared to the CD4 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD4 transmembrane domain polypeptide. In embodiments, the CD4 transmembrane domain is a human CD4 transmembrane domain protein. In embodiments, a variant or mutant of the CD4 transmembrane domain protein includes no more than 5, 4, 3, 2, or 1 deletions compared to the naturally occurring CD4 transmembrane domain protein. In embodiments, a variant or mutant of the CD4 transmembrane domain protein includes no more than 5, 4, 3, 2, or 1 insertions compared to the naturally occurring CD4 transmembrane domain protein. In embodiments, a variant or mutant of the CD4 transmembrane domain protein does not include deletions compared to the naturally occurring CD4 transmembrane domain protein. In embodiments, a variant or mutant of the CD4 transmembrane domain protein does not include insertions compared to the naturally occurring CD4 transmembrane domain protein. In embodiments, a variant or mutant of the CD4 transmembrane domain protein includes substitutions that are conservative substitutions compared to the naturally occurring CD4 transmembrane domain protein. In embodiments, the CD4 transmembrane domain includes all or a portion of the protein identified by the NCBI sequence reference NP_000607.1, or an isoform or naturally occurring mutant or variant thereof. In embodiments, the CD4 transmembrane domain includes all or a portion of the protein identified by the NCBI sequence reference NP_001181943.1, or an isoform or naturally occurring mutant or variant thereof. In embodiments, the CD4 transmembrane domain includes all or a portion of the protein identified by the NCBI sequence reference NP_001181944.1, or an isoform or naturally occurring mutant or variant thereof. In embodiments, the CD4 transmembrane domain includes all or a portion of the protein identified by the NCBI sequence reference NP_001181945.1, or an isoform or naturally occurring mutant or variant thereof. In embodiments, the CD4 transmembrane domain includes all or a portion of the protein identified by the NCBI sequence reference NP_001181946.1, or an isoform or naturally occurring mutant or variant thereof.

The term "CD8 transmembrane domain" as provided herein includes any of the recombinant or naturally-occurring forms of the transmembrane domain of CD8, or variants or homologs thereof that maintain CD8 transmembrane domain activity (e.g. within at least 50%, 80%, 90%, 95%, 96%, 97%, 98%, 99% or 100% activity compared to the CD8 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD8 transmembrane domain polypeptide. In embodiments, the CD8 transmembrane domain is CD8A transmembrane domain. In embodiments, the CD8 transmembrane domain is a CD8B transmembrane domain. In embodiments, the CD8 transmembrane domain is a human CD8 transmembrane domain protein. In embodiments, a variant or mutant of the CD8 transmembrane domain protein includes no more than 5, 4, 3, 2, or 1 deletions compared to the naturally occurring CD8 transmembrane domain protein. In embodiments, a variant or mutant of the CD8 transmembrane domain protein includes no more than 5, 4, 3, 2, or 1 insertions compared to the naturally occurring CD8 transmembrane domain protein. In embodiments, a variant or mutant of the CD8 transmembrane domain protein does not include deletions compared to the naturally occurring CD8 transmembrane domain protein. In embodiments, a variant or mutant of the CD8 transmembrane domain protein does not include insertions compared to the naturally occurring CD8 transmembrane domain protein. In embodiments, a variant or mutant of the CD8 transmembrane domain protein includes substitutions that are conservative substitutions compared to the naturally occurring CD8 transmembrane domain protein. In embodiments, the CD8 transmembrane domain includes all or a portion of the protein identified by the NCBI sequence reference NP_001139345.1, or an isoform or naturally occurring mutant or variant thereof. In embodiments, the CD8 transmembrane domain includes all or a portion of the protein identified by the NCBI sequence reference NP_001181943.1, or an isoform or naturally occurring mutant or variant thereof. In embodiments, the CD8 transmembrane domain includes all or a portion of the protein identified by the NCBI sequence reference NP_001181944.1, or an isoform or naturally occurring mutant or variant thereof. In embodiments, the CD8 transmembrane domain includes all or a portion of the protein identified by the NCBI sequence reference NP_001181945.1, or an isoform or naturally occurring mutant or variant thereof. In embodiments, the CD8 transmembrane domain includes all or a portion of the protein identified by the NCBI sequence reference NP_741969.1, or an isoform or naturally occurring mutant or variant thereof. In embodiments, the CD8 transmembrane domain includes all or a portion of the protein identified by the NCBI sequence reference NP_001759.3, or an isoform or naturally occurring mutant or variant thereof. In embodiments, the CD8 transmembrane domain includes all or a portion of the protein identified by the NCBI sequence reference XP_011531466.1, or an isoform or naturally occurring mutant or variant thereof. In embodiments, the CD8 transmembrane domain includes all or a portion of the protein identified by the NCBI sequence reference NP_001171571.1, or an isoform or naturally occurring mutant or variant thereof. In embodiments, the CD8 transmembrane domain includes all or a portion of the protein identified by the NCBI sequence reference NP_757362.1, or an isoform or naturally occurring mutant or variant thereof. In embodiments, the CD8 transmembrane domain includes all or a portion of the protein identified by the NCBI sequence reference NP_742100.1, or an isoform or naturally occurring mutant or variant thereof. In embodiments, the CD8 transmembrane domain includes all or a portion of the protein identified by the NCBI sequence reference NP_742099.1, or an isoform or naturally occurring mutant or variant thereof. In embodiments, the CD8 transmembrane domain includes all or a portion of the protein identified by the NCBI sequence reference NP_004922.1, or an isoform or naturally occurring mutant or variant thereof.

The term "CD3-zeta transmembrane domain" as provided herein includes any of the recombinant or naturally-occurring forms of the transmembrane domain of CD3-zeta, or variants or homologs thereof that maintain CD3-zeta transmembrane domain activity (e.g. within at least 50%, 80%, 90%, 95%, 96%, 97%, 98%, 99% or 100% activity compared to the CD3-zeta transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD3-zeta transmembrane domain polypeptide. In embodiments, the CD3-zeta transmembrane domain is a human CD3-zeta transmembrane domain protein. In embodiments, a variant or mutant of the CD3-zeta transmembrane domain protein includes no more than 5, 4, 3, 2, or 1 deletions compared to the naturally occurring CD3-zeta transmembrane domain protein. In embodiments, a variant or mutant of the CD3-zeta transmembrane domain protein includes no more than 5, 4, 3, 2, or 1 insertions compared to the naturally occurring CD3-zeta transmembrane domain protein. In embodiments, a variant or mutant of the CD3-zeta transmembrane domain protein does not include deletions compared to the naturally occurring CD3-zeta transmembrane domain protein. In embodiments, a variant or mutant of the CD3-zeta transmembrane domain protein does not include insertions compared to the naturally occurring CD3-zeta transmembrane domain protein. In embodiments, a variant or mutant of the CD3-zeta transmembrane domain protein includes substitutions that are conservative substitutions compared to the naturally occurring CD3-zeta transmembrane domain protein. In embodiments, the CD3-zeta transmembrane domain includes all or a portion of the protein identified by the NCBI sequence reference NP_000725.1, or an isoform or naturally occurring mutant or variant thereof. In embodiments, the CD3-zeta transmembrane domain includes all or a portion of the protein identified by the NCBI sequence reference NP_932170.1, or an isoform or naturally occurring mutant or variant thereof.

The term "CD28 co-stimulatory domain" as provided herein includes any of the recombinant or naturally-occurring forms of the co-stimulatory domain of CD28, or variants or homologs thereof that maintain CD28 co-stimulatory domain activity (e.g. within at least 50%, 80%, 90%, 95%, 96%, 97%, 98%, 99% or 100% activity compared to the CD28 co-stimulatory domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD28 co-stimulatory domain polypeptide. In embodiments, the CD28 co-stimulatory domain is a human CD28 co-stimulatory domain protein. In embodiments, a variant or mutant of the CD28 co-stimulatory domain protein includes no more than 5, 4, 3, 2, or 1 deletions compared to the naturally occurring CD28 co-stimulatory domain protein. In embodiments, a variant or mutant of the CD28 co-stimulatory domain protein includes no more than 5, 4, 3, 2, or 1 insertions compared to the naturally occurring CD28 co-stimulatory domain protein. In embodiments, a variant or mutant of the CD28 co-stimulatory domain protein does not include deletions compared to the naturally occurring CD28 co-stimulatory domain protein. In embodiments, a variant or mutant of the CD28 co-stimulatory domain protein does not include insertions compared to the naturally occurring CD28 co-stimulatory domain protein. In embodiments, a variant or mutant of the CD28 co-stimulatory domain protein includes substitutions that are conservative substitutions compared to the naturally occurring CD28 co-stimulatory domain protein. In embodiments, the CD28 co-stimulatory domain includes all or a portion of the protein identified by the NCBI sequence reference NP_001230006.1, or an isoform or naturally occurring mutant or variant thereof. In embodiments, the CD28 co-stimulatory domain includes all or a portion of the protein identified by the NCBI sequence reference NP_001230007.1, or an isoform or naturally occurring mutant or variant thereof. In embodiments, the CD28 co-stimulatory domain includes all or a portion of the protein identified by the NCBI sequence reference NP_006130.1, or an isoform or naturally occurring mutant or variant thereof.

The term "4-1BB co-stimulatory domain" as provided herein includes any of the recombinant or naturally-occurring forms of the co-stimulatory domain of 4-1BB, or variants or homologs thereof that maintain 4-1BB co-stimulatory domain activity (e.g. within at least 50%, 80%, 90%, 95%, 96%, 97%, 98%, 99% or 100% activity compared to the 4-1BB co-stimulatory domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring 4-1BB co-stimulatory domain polypeptide. In embodiments, the 4-1BB co-stimulatory domain is a human 4-1BB co-stimulatory domain protein. In embodiments, a variant or mutant of the 4-1BB co-stimulatory domain protein includes no more than 5, 4, 3, 2, or 1 deletions compared to the naturally occurring 4-1BB co-stimulatory domain protein. In embodiments, a variant or mutant of the 4-1BB co-stimulatory domain protein includes no more than 5, 4, 3, 2, or 1 insertions compared to the naturally occurring 4-1BB co-stimulatory domain protein. In embodiments, a variant or mutant of the 4-1BB co-stimulatory domain protein does not include deletions compared to the naturally occurring 4-1BB co-stimulatory domain protein. In embodiments, a variant or mutant of the 4-1BB co-stimulatory domain protein does not include insertions compared to the naturally occurring 4-1BB co-stimulatory domain protein. In embodiments, a variant or mutant of the 4-1BB co-stimulatory domain protein includes substitutions that are conservative substitutions compared to the naturally occurring 4-1BB co-stimulatory domain protein. In embodiments, the 4-1BB co-stimulatory domain protein amino acid sequence has at least or about 50%, 60%, 70%, 75%, 80%, 85%, 90%, 91%, 92%, 93%, 94%, 95%, 96%, 97%, 98%, or 99% sequence identify to SEQ ID NO:14. In embodiments, the 4-1BB co-stimulatory domain includes all or a portion of the protein identified by the NCBI sequence reference NP_001552.2 or an isoform or naturally occurring mutant or variant thereof.

The term "ICOS co-stimulatory domain" as provided herein includes any of the recombinant or naturally-occurring forms of the co-stimulatory domain of ICOS, or variants or homologs thereof that maintain ICOS co-stimulatory domain activity (e.g. within at least 50%, 80%, 90%, 95%, 96%, 97%, 98%, 99% or 100% activity compared to the ICOS co-stimulatory domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring ICOS co-stimulatory domain polypeptide. In embodiments, the ICOS co-stimulatory domain is a human ICOS co-stimulatory domain protein. In embodiments, a variant or mutant of the ICOS co-stimulatory domain protein includes no more than 5, 4, 3, 2, or 1 deletions compared to the naturally occurring ICOS co-stimulatory domain protein. In embodiments, a variant or mutant of the ICOS co-stimulatory domain protein includes no more than 5, 4, 3, 2, or 1 insertions compared to the naturally occurring ICOS co-stimulatory domain protein. In embodiments, a variant or mutant of the ICOS co-stimulatory domain protein does not include deletions compared to the naturally occurring ICOS co-stimulatory domain protein. In embodiments, a variant or mutant of the ICOS co-stimulatory domain protein does not include insertions compared to the naturally occurring ICOS co-stimulatory domain protein. In embodiments, a variant or mutant of the ICOS co-stimulatory domain protein includes substitutions that are conservative substitutions compared to the naturally occurring ICOS co-stimulatory domain protein. In embodiments, the ICOS co-stimulatory domain includes all or a portion of the protein identified by the NCBI sequence reference NP_036224.1, or an isoform or naturally occurring mutant or variant thereof.

The term "OX-40 co-stimulatory domain" as provided herein includes any of the recombinant or naturally-occurring forms of the co-stimulatory domain of OX-40, or variants or homologs thereof that maintain OX-40 co-stimulatory domain activity (e.g. within at least 50%, 80%, 90%, 95%, 96%, 97%, 98%, 99% or 100% activity compared to the OX-40 co-stimulatory domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring OX-40 co-stimulatory domain polypeptide. In embodiments, the OX-40 co-stimulatory domain is a human OX-40 co-stimulatory domain protein. In embodiments, a variant or mutant of the OX-40 co-stimulatory domain protein includes no more than 5, 4, 3, 2, or 1 deletions compared to the naturally occurring OX-40 co-stimulatory domain protein. In embodiments, a variant or mutant of the OX-40 co-stimulatory domain protein includes no more than 5, 4, 3, 2, or 1 insertions compared to the naturally occurring OX-40 co-stimulatory domain protein. In embodiments, a variant or mutant of the OX-40 co-stimulatory domain protein does not include deletions compared to the naturally occurring OX-40 co-stimulatory domain protein. In embodiments, a variant or mutant of the OX-40 co-stimulatory domain protein does not include insertions compared to the naturally occurring OX-40 co-stimulatory domain protein. In embodiments, a variant or mutant of the OX-40 co-stimulatory domain protein includes substitutions that are conservative substitutions compared to the naturally occurring OX-40 co-stimulatory domain protein. In embodiments, the OX-40 co-stimulatory domain includes all or a portion of the protein identified by the NCBI sequence reference NP_003318.1, or an isoform or naturally occurring mutant or variant thereof.

The term "CTLA-4 co-stimulatory domain" as provided herein includes any of the recombinant or naturally-occurring forms of the co-stimulatory domain of CTLA-4, or variants or homologs thereof that maintain CTLA-4 co-stimulatory domain activity (e.g. within at least 50%, 80%, 90%, 95%, 96%, 97%, 98%, 99% or 100% activity compared to the CTLA-4 co-stimulatory domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CTLA-4 co-stimulatory domain polypeptide. In embodiments, CTLA-4 co-stimulatory domain protein is a human CTLA-4 co-stimulatory domain protein. In embodiments, the CTLA-4 co-stimulatory domain includes no more than 5, 4, 3, 2, or 1 deletions. In embodiments, the CTLA-4 co-stimulatory domain protein includes no more than 5, 4, 3, 2, or 1 insertions. In embodiments, the CTLA-4 co-stimulatory domain protein does not include deletions. In embodiments, CTLA-4 co-stimulatory domain protein does not include insertions. In embodiments, the CTLA-4 co-stimulatory domain protein includes substitutions that are conservative substitutions. In embodiments, the CTLA-4 co-stimulatory domain is a human CTLA-4 co-stimulatory domain protein. In embodiments, a variant or mutant of the CTLA-4 co-stimulatory domain protein includes no more than 5, 4, 3, 2, or 1 deletions compared to the naturally occurring CTLA-4 co-stimulatory domain protein. In embodiments, a variant or mutant of the CTLA-4 co-stimulatory domain protein includes no more than 5, 4, 3, 2, or 1 insertions compared to the naturally occurring CTLA-4 co-stimulatory domain protein. In embodiments, a variant or mutant of the CTLA-4 co-stimulatory domain protein does not include deletions compared to the naturally occurring CTLA-4 co-stimulatory domain protein. In embodiments, a variant or mutant of the CTLA-4 co-stimulatory domain protein does not include insertions compared to the naturally occurring CTLA-4 co-stimulatory domain protein. In embodiments, a variant or mutant of the CTLA-4 co-stimulatory domain protein includes substitutions that are conservative substitutions compared to the naturally occurring CTLA-4 co-stimulatory domain protein.

The term "CD3ζ intracellular T-cell signaling domain" as provided herein includes any of the recombinant or naturally-occurring forms of the CD3 intracellular T-cell signaling domain, or variants or homologs thereof that maintain CD3ζ intracellular T-cell signaling domain activity (e.g. within at least 50%, 80%, 90%, 95%, 96%, 97%, 98%, 99% or 100% activity compared to the CD3ζ intracellular T-cell signaling domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD3ζ intracellular T-cell signaling domain polypeptide. In embodiments, the CD3ζ intracellular T-cell signaling domain is a human CD3ζ intracellular T-cell signaling domain protein. In embodiments, a variant or mutant of the CD3ζ intracellular T-cell signaling domain protein includes no more than 5, 4, 3, 2, or 1 deletions compared to the naturally occurring CD3ζ intracellular T-cell signaling domain protein. In embodiments, a variant or mutant of the CD3ζ intracellular T-cell signaling domain protein includes no more than 5, 4, 3, 2, or 1 insertions compared to the naturally occurring CD3ζ intracellular T-cell signaling domain protein. In embodiments, a variant or mutant of the CD3ζ intracellular T-cell signaling domain protein does not include deletions compared to the naturally occurring CD3ζ intracellular T-cell signaling domain protein. In embodiments, a variant or mutant of the CD3ζ intracellular T-cell signaling domain protein does not include insertions compared to the naturally occurring CD3ζ intracellular T-cell signaling domain protein. In embodiments, a variant or mutant of the CD3ζ intracellular T-cell signaling domain protein includes substitutions that are conservative substitutions compared to the naturally occurring CD3ζ intracellular T-cell signaling domain protein. In embodiments, the CD3ζ intracellular T-cell signaling domain includes all or a portion of the protein identified by the NCBI sequence reference NP_000725.1, or an isoform or naturally occurring mutant or variant thereof. In embodiments, the CD3ζ intracellular T-cell signaling domain includes all or a portion of the protein identified by the NCBI sequence reference NP_932170.1, or an isoform or naturally occurring mutant or variant thereof. Non-limiting examples of human CD3-zeta amino acid sequences available under NCBI sequence references are identified supra.

In embodiments, the CD3ζ intracellular T-cell signaling domain is encoded by all or a portion of the nucleic acid sequence identified by the NCBI sequence reference NM_000734.3, or an isoform or naturally occurring mutant or variant thereof. In embodiments, the CD3ζ intracellular T-cell signaling domain is encoded by all or a portion of the nucleic acid sequence identified by the NCBI sequence reference NM_198053.2, or an isoform or naturally occurring mutant or variant thereof. In embodiments, a variant or mutant of the CD3ζ intracellular T-cell signaling domain nucleic acid sequence includes no more than 5, 4, 3, 2, or 1 deletions compared to the naturally occurring CD3ζ intracellular T-cell signaling domain nucleic acid sequence. In embodiments, a variant or mutant of the CD3ζ intracellular T-cell signaling domain nucleic acid sequence includes no more than 5, 4, 3, 2, or 1 insertions compared to the naturally occurring CD3ζ intracellular T-cell signaling domain nucleic acid sequence. In embodiments, a variant or mutant of the CD3ζ intracellular T-cell signaling domain nucleic acid sequence does not include deletions compared to the naturally occurring CD3ζ intracellular T-cell signaling domain nucleic acid sequence. In embodiments, a variant or mutant of the CD3ζ intracellular T-cell signaling domain nucleic acid sequence does not include insertions compared to the naturally occurring CD3ζ intracellular T-cell signaling domain nucleic acid sequence. In embodiments, a variant or mutant of the CD3 intracellular T-cell signaling domain nucleic acid sequence includes substitutions that are conservative substitutions compared to the naturally occurring CD3ζ intracellular T-cell signaling domain nucleic acid sequence.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). Controls are also valuable for determining the significance of data. For example, if values for a given parameter are widely variant in controls, variation in test samples will not be considered as significant.

As used herein, the term "cancer" or "tumor" refers to all types of cancer, neoplasm or malignant tumors found in mammals (e.g. humans), including leukemias, lymphomas, carcinomas and sarcomas. Exemplary cancers that may be treated with a compound or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is no prophylactic treatment.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g., achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, Dosage Calculations (1999); and *Remington: The Science and Practice of Pharmacy,* 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

An "anticancer agent" as used herein refers to a molecule (e.g. compound, peptide, protein, nucleic acid, 0103) used to treat cancer through destruction or inhibition of cancer cells or tissues. Anticancer agents may be selective for certain cancers or certain tissues. In embodiments, anticancer agents herein may include epigenetic inhibitors and multi-kinase inhibit "Anti-cancer agent" and "anticancer agent" are used in accordance with their plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine;

bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclix-imab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride;

hydroxyurea; idarubicin hydrochloride; ifosfamide; iimofosine; interleukin Il (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, Inanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

“Selective” or “selectivity” or the like of a compound refers to the compound’s ability to discriminate between molecular targets (e.g. a compound having selectivity toward ROR1).

“Specific”, “specifically”, “specificity”, or the like of a compound refers to the compound’s ability to cause a particular action, such as inhibition, to a particular molecular target with minimal or no action to other proteins in the cell.

An "ROR1 inhibitor" refers to a compound (e.g. compounds described herein) that reduces the activity of ROR1 when compared to a control, such as absence of the compound or a compound with known inactivity.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation). A "ROR1 inhibitor" is a compound that negatively affects (e.g. decreases) the activity or function of ROR1 relative to the activity or function of ROR1 in the absence of the inhibitor.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "associated" or "associated with" in the context of a substance or substance activity or function associated with a disease (e.g. a protein associated disease, a cancer associated with ROR1 activity, ROR1 associated cancer, ROR1 associated disease (e.g., cancer, inflammatory disease, autoimmune disease, or infectious disease)) means that the disease (e.g. cancer, inflammatory disease, autoimmune disease, or infectious disease) is caused by (in whole or in part), or a symptom of the disease is caused by (in whole or in part) the substance or substance activity or function. As used herein, what is described as being associated with a disease, if a causative agent, could be a target for treatment of the disease. For example, a cancer associated with ROR1 activity or function or a ROR1 associated disease (e.g., cancer, inflammatory disease, autoimmune disease, or infectious disease), may be treated with a ROR1 modulator or ROR1 inhibitor, in the instance where increased ROR1 activity or function (e.g. signaling pathway activity) causes the disease (e.g., cancer, inflammatory disease, autoimmune disease, or infectious disease). For example, an inflammatory disease associated with ROR1 activity or function or an ROR1 associated inflammatory disease, may be treated with an ROR1 modulator or ROR1 inhibitor, in the instance where increased ROR1 activity or function (e.g. signaling pathway activity) causes the disease.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Compositions

Provided herein are recombinant protein/chimeric antigen receptor (these terms are used interchangeably throughout) compositions and methods of using the same that are, inter alia, useful for treating hematological malignancies. Applicants have discovered that chimeric antigen receptors (CARs) directed to ROR-1 provide for highly active and efficient immunotherapeutic compositions. Without being bound to any particular theory, antibodies known to inhibit the receptor they bind and downregulate its surface expression are generally not considered good clinical candidates for CARs. Therefore, it was very surprising that CARS including CDRs of ROR-1 antibodies described herein including embodiments thereof exhibit effective cancer-specific cytotoxicity when expressed by T cells.

In one aspect, there is provided a recombinant protein or a composition comprising a recombinant protein, which includes an antigen binding region, preferably a ROR-1 binding domain, and a transmembrane domain. In embodiments, the ROR-1 binding domain is an antibody. In embodiments, the ROR-1 binding domain is an antibody fragment.

In one aspect, there is provided a recombinant protein including (i) an antibody region including: (a) a light chain variable domain comprising a CDR L1 as set forth in SEQ ID NO: 43, a CDR L2 as set forth in SEQ ID NO:44 and a CDR L3 as set forth in SEQ ID NO:45; and (b) a heavy chain variable domain comprising a CDR H1 as set forth in SEQ ID NO:46, a CDR H2 as set forth in SEQ ID NO:47, and a CDR H3 as set forth in SEQ ID NO:48; and (ii) a transmembrane domain.

In one aspect a chimeric antigen receptor is provided. The chimeric antigen receptor includes: i. an antigen binding region, wherein the antigen binding region specifically binds ROR-1, a transmembrane domain, a spacer domain that couples the antigen binding region and the transmembrane domain, and an intracellular domain. The terms "antibody region", "antigen binding region", or "antigen binding domain" as provided herein are used interchangeably throughout and refer to a monovalent or multivalent protein moiety that forms part of the protein (i.e. recombinant protein, chimeric antigen receptor) provided herein including embodiments thereof. A person of ordinary skill in the art would therefore immediately recognize that the antibody region or antigen binding region is a protein moiety capable of binding an antigen (epitope). In embodiments, the ROR-1 binding domain includes an antibody region including a light chain variable region ($V_L$) and a heavy chain variable region ($V_H$). In embodiments, the light chain variable domain includes a CDR L1 as set forth in SEQ ID NO:43, a CDR L2 as set forth in SEQ ID NO:44 and a CDR L3 as set forth in SEQ ID NO:45, and the heavy chain variable domain including a CDR H1 as set forth in SEQ ID NO:46, a CDR H2 as set forth in SEQ ID NO:47, and a CDR H3 as set forth in SEQ ID NO:48. It is noted that those CDRs are of or are derived from cirmtuzumab (also known as UC-961 or 99961.1). The development and structure of cirmtuzumab is disclosed in U.S. patent application Ser. No. 14/422,519, which is incorporated by reference herein in its entirety and for all purposes. In embodiments, the ROR-1 binding domain includes an antibody region including CDR L1 as set forth in SEQ ID NO:49, a CDR L2 as set forth in SEQ ID NO:50 and a CDR L3 as set forth in SEQ ID NO:51, and the heavy chain variable domain includes a CDR H1 as set forth in SEQ ID NO:52, a CDR H2 as set forth in SEQ ID NO:53, and a CDR H3 as set forth in SEQ ID NO:54.

In one aspect a chimeric antigen receptor is provided. The chimeric antigen receptor includes: i. an antigen binding region, wherein the antigen binding region specifically binds ROR-1, and wherein the antigen binding region includes a light chain variable domain and a heavy chain variable domain; (a) wherein the light chain variable domain includes a CDR L1 as set forth in SEQ ID NO:43, a CDR L2 as set forth in SEQ ID NO:44 and a CDR L3 as set forth in SEQ ID NO:45; and the heavy chain variable domain includes a CDR H1 as set forth in SEQ ID NO: 46, a CDR H2 as set forth in SEQ ID NO:47, and a CDR H3 as set forth in SEQ ID NO: 48; or (b) wherein the light chain variable domain includes a CDR L1 as set forth in SEQ ID NO: 49, a CDR L2 as set forth in SEQ ID NO:50 and a CDR L3 as set forth in SEQ ID NO:51; and the heavy chain variable domain includes a CDR H1 as set forth in SEQ ID NO:52, a CDR H2 as set forth in SEQ ID NO:53, and a CDR H3 as set forth in SEQ ID NO:54; ii. a spacer domain, wherein the spacer domain includes a spacer of between 10 and 240 amino acids in length; iii. a transmembrane domain; and iv. an intracellular domain.

In one aspect a chimeric antigen receptor is provided. The chimeric antigen receptor includes: i. an antigen binding region, wherein the antigen binding region specifically binds ROR-1 and wherein the antigen binding region includes a light chain variable domain and a heavy chain variable domain; (a) wherein the light chain variable domain includes a CDR L1 as set forth in SEQ ID NO:43, a CDR L2 as set forth in SEQ ID NO:44 and a CDR L3 as set forth in SEQ ID NO:45; and the heavy chain variable domain includes a CDR H1 as set forth in SEQ ID NO: 46, a CDR H2 as set forth in SEQ ID NO:47, and a CDR H3 as set forth in SEQ ID NO: 48; or (b) wherein said light chain variable domain includes a CDR L1 as set forth in SEQ ID NO: 49, a CDR L2 as set forth in SEQ ID NO:50 and a CDR L3 as set forth in SEQ ID NO: 51; and the heavy chain variable domain including a CDR H1 as set forth in SEQ ID NO:52, a CDR H2 as set forth in SEQ ID NO:53, and a CDR H3 as set forth in SEQ ID NO:54; ii. a transmembrane domain; and iii. an intracellular domain, wherein the intracellular domain includes an intracellular T cell signaling domain and an intracellular co-stimulatory domain selected from, 4-1BB, ICOS, OX-40, and combinations thereof.

The terms "antibody region" and "antigen binding region" as provided herein are used interchangeably throughout and refer to a monovalent or multivalent protein moiety that forms part of the protein (i.e. recombinant protein, chimeric antigen receptor) provided herein including embodiments thereof. A person of ordinary skill in the art would therefore immediately recognize that the antibody region or antigen binding region is a protein moiety capable of binding an antigen (epitope). The antibody region provided herein may include a domain of an antibody or fragment (e.g., Fab) thereof. Thus, the antibody region may include a light chain variable domain (VL) and/or a heavy chain variable domain (VH).

A light chain variable (VL) domain as provided includes CDR sequences and framework region (FR) sequences of the light chain of an antibody, an antibody variant or fragment thereof. In embodiments, the antibody region or antigen binding region includes a variable light chain domain and a variable heavy chain domain. A "variable light chain domain" as provided herein refers to a polypeptide included in (forming part of) a light chain variable (VL) region. In embodiments, the variable light chain region is a light chain variable (VL) domain. A "variable heavy chain domain" as provided herein refers to a polypeptide included in (forming part of) a heavy chain variable (VH) region. In embodiments, the variable heavy chain region is a heavy chain variable (VH) domain. In embodiments, the light chain variable (VL) domain includes CDR L1 (SEQ ID NO:43), CDR L2 (SEQ ID NO:44), and CDR L3 (SEQ ID NO: 45). In embodiments, the heavy chain variable (VH) domain includes CDR H1 (SEQ ID NO: 46), CDR H2 (SEQ ID NO:47), and CDR H3 (SEQ ID NO:48). It is noted that those CDRs are of or are derived from cirmtuzumab (also known as UC-961 or 99961.1). The development and structure of cirmtuzumab is disclosed in U.S. patent application Ser. No. 14/422,519 which is incorporated by reference herein in its entirety and for all purposes.

In embodiments, the light chain variable domain includes the amino acid sequence of SEQ ID NO:21, or an amino acid sequence at least 80%, 85%, 90%, or 95% identical to SEQ ID NO: 21. In embodiments, the light chain variable domain has the amino acid sequence of SEQ ID NO: 21, or an amino acid sequence at least 80%, 85%, 90%, or 95% identical to SEQ ID NO: 21. In embodiments, the heavy chain variable domain includes the amino acid sequence of SEQ ID NO:27, or an amino acid sequence at least 80%, 85%, 90%, or 95% identical to SEQ ID NO: 27. In embodiments, the heavy chain variable domain has the amino acid sequence of SEQ ID NO: 27, or an amino acid sequence at least 80%, 85%, 90%, or 95% identical to SEQ ID NO: 27.

In embodiments, the light chain variable domain includes the amino acid sequence of SEQ ID NO:19, or an amino acid sequence at least 80%, 85%, 90%, or 95% identical to SEQ ID NO:19. In embodiments, the light chain variable domain has the amino acid sequence of SEQ ID NO:19, or an amino acid sequence at least 80%, 85%, 90%, or 95% identical to SEQ ID NO:19. In embodiments, the light chain variable domain includes the amino acid sequence of SEQ ID NO: 20, or a sequence at least 80%, 85%, 90%, or 95% identical to SEQ ID NO:20. In embodiments, the light chain variable domain has the amino acid sequence of SEQ ID NO:20, or an amino acid sequence at least 80%, 85%, 90%, or 95% identical to SEQ ID NO:20. In embodiments, the heavy chain variable domain includes the amino acid sequence of SEQ ID NO: 25, or an amino acid sequence at least 80%, 85%, 90%, or 95% identical to SEQ ID NO:25. In embodiments, the heavy chain variable domain has the amino acid sequence of SEQ ID NO: 25, or an amino acid sequence at least 80%, 85%, 90%, or 95% identical to SEQ ID NO:25. In embodiments, the heavy chain variable domain includes the amino acid sequence of SEQ ID NO: 26, or an amino acid sequence at least 80%, 85%, 90%, or 95% identical to SEQ ID NO:26. In embodiments, the heavy chain variable domain has the amino acid sequence of SEQ ID NO: 26, or an amino acid sequence at least 80%, 85%, 90%, or 95% identical to SEQ ID NO:26.

In embodiments, the C-terminus of the light chain variable domain is bound to the N-terminus of the heavy chain variable domain. In embodiments, the N-terminus of the light chain variable domain is bound to the C-terminus of the heavy chain variable domain. In embodiments, the light chain variable domain is covalently bound to the heavy chain variable domain through a chemical linker. A “chemical linker,” as provided herein, is a covalent linker, a non-covalent linker, a peptide linker (a linker including a peptide moiety), a cleavable peptide linker, a substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene or any combination thereof. Thus, a chemical linker as provided herein may include a plurality of chemical moieties, wherein each of the plurality of chemical moieties is chemically different. Alternatively, the chemical linker may be a non-covalent linker. Examples of non-covalent linkers include without limitation, ionic bonds, hydrogen bonds, halogen bonds, van der Waals interactions (e.g. dipole-dipole, dipole-induced dipole, London dispersion), ring stacking (pi effects), and hydrophobic interactions. In embodiments, a chemical linker is formed using conjugate chemistry including, but not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). In embodiments, the chemical linker is a peptide linker, which comprises 5-100, 5-80, 5-70, 5-60, 5-50, 10-50, 10-40, or 10-30 amino acids in length. Any sequence that provides sufficient flexibility between the light chain variable domain and the heavy chain variable domain is contemplated for the recombinant proteins provided herein including embodiments thereof. In embodiments, the peptide linker includes or has the amino acid sequence of SEQ ID NO: 24. In embodiments, the peptide linker has an amino acid sequence at least 80%, 85%, 90%, or 95% identical to SEQ ID NO:24.

Any transmembrane domain capable of anchoring the proteins provided herein including embodiments thereof are contemplated. While any suitable transmembrane domains are contemplated herein, exemplary, but non-limiting examples of transmembrane domains include the transmembrane domains of CD28, CD8, CD4, CD3ζ, or CD8α. In preferred embodiments, the transmembrane domain is a CD28 transmembrane domain. The term “CD28 transmembrane domain” as provided herein includes any of the recombinant or naturally-occurring forms of the transmembrane domain of CD28, or variants or homologs thereof that maintain CD28 transmembrane domain activity (e.g. within at least 50%, 80%, 90%, 95%, 96%, 97%, 98%, 99% or 100% activity compared to the CD28 transmembrane domain). In some aspects, the variants or homologs have at least 80%, 85%, 90%, 95%, 96%, 97%, 98%, or 99% amino acid sequence identity across the whole sequence or a portion of the a naturally occurring CD28 transmembrane domain polypeptide. In embodiments, the CD28 transmembrane domain includes an amino acid sequence of SEQ ID NO:32. In embodiments, the CD28 transmembrane domain is an amino acid sequence of SEQ ID NO:32. In embodiments, the CD28 transmembrane domain in the ROR1 CAR described herein has a sequence at least 80%, 85%, 90%, or 95% identical to SEQ ID NO:32.

In embodiments, the C-terminus of the heavy chain variable domain is coupled to the N-terminus of the transmembrane domain. In embodiments, the C-terminus of the light chain variable domain is coupled to the N-terminus of the transmembrane domain. In embodiments, the heavy chain variable domain or light chain variable domain is covalently bound to the transmembrane domain through a spacer domain. In embodiments, the binding affinity of the antigen binding region to the antigen is increased in the CAR construct having the spacer domain. In embodiments, the activity of the CAR having the spacer domain is higher than the CAR without the spacer domain. In embodiments, the flexibility of the antigen binding region of the CAR is increased by the presence of the spacer domain.

Any suitable chemical or biological moieties that can provide a space or flexibility to the antigen binding region or antigen binding domain, without providing excessive steric hindrance to the antigen binding domain, are contemplated. Preferably, the spacer domain comprises a polypeptides that are in length of between 10-250 amino acids, between 12-250 amino acids, between 12-200 amino acids, between 14-250 amino acids, between 14-200 amino acids, between 14-150 amino acids. Thus, exemplary spacer domains herein include, but not limited to, immunoglobulin molecules or fragments thereof (e.g., IgG1, IgG2, IgG3, IgG4, or constant heavy chain 1 (CH1), constant heavy chain 2 (CH2), or constant heavy chain 3 (CH3) domain(s) of the IgG1, IgG2, IgG3 or IgG4) or immunoglobulin molecules or fragments thereof (e.g., IgG1, IgG2, IgG3, IgG4) including mutations affecting Fc receptor binding. Alternatively and/or additionally, some contemplated spacer domains include all or parts of an immunoglobulin (e.g., IgG1, IgG2, IgG3, IgG4) hinge region, i.e., the sequence that falls between the CH1 and CH2 domains of an immunoglobulin, e.g., an IgG4 Fc hinge or a CD8 hinge. Some spacer domains include an immunoglobulin CH3 domain or both a CH3 domain and a CH2 domain. The immunoglobulin derived sequences can include one or more amino acid modifications, for example, 1, 2, 3, 4 or 5 substitutions (e.g., substitutions that reduce off-target binding) or addition of less than 10, less than 5, less than 3 amino acid sequences at its N terminal or C terminal ends.

In embodiments, the spacer domain includes a hinge domain, and optionally one of or both of CH3 domain and CH2 domain of an immunoglobulin molecule. Thus, in embodiments, a spacer domain has or consists of a hinge region or a modified hinge region (e.g., with one or more amino acid substitution or addition). In embodiments, a spacer domain has or consists of a hinge region coupled to the CH3 domain of hIgG4 at the C-terminus of the hinge region. In embodiments, a spacer domain has or consists of a hinge region coupled to the CH2 domain of hIgG4 at the C-terminus of the hinge region. Alternatively, a spacer domain has or consists of a hinge region coupled to the CH2-CH3 domain of the hIgG4 at the C-terminus of the hinge region. In embodiments, the hinge region used herein comprises or consist of an amino acid sequence of SEQ ID NO:29, or an amino acid sequence at least 80%, 85%, 90%, or 95% identical to SEQ ID NO:29. In embodiments, the spacer domain includes the amino acid sequence of SEQ ID NO:29, SEQ ID NO:41 or SEQ ID NO:42 or an amino acid sequence at least 80%, 85%, 90%, or 95% identical to SEQ ID NO:29, SEQ ID NO:41 or SEQ ID NO:42. In embodiments, the spacer domain has or consists of the amino acid sequence of SEQ ID NO:29, SEQ ID NO:41 or SEQ ID NO:42 or an amino acid sequence at least 80%, 85%, 90%, or 95% identical to SEQ ID NO:29, SEQ ID NO:41 or SEQ ID NO:42.

In embodiments, the recombinant protein (e.g., the intracellular domain) further includes one or more intracellular co-stimulatory signaling domains. An "intracellular co-stimulatory signaling domain" as provided herein includes amino acid sequences capable of providing co-stimulatory signaling in response to binding of an antigen to the antibody region provided herein including embodiments thereof. In embodiments, the signaling of the co-stimulatory signaling domain results in production of cytokines and proliferation of the T cell expressing the same. In embodiments, the intracellular co-stimulatory signaling domain comprises at least one or more of a CD28 intracellular co-stimulatory signaling domain, a 4-1BB (CD137) intracellular co-stimulatory signaling domain, an ICOS intracellular co-stimulatory signaling domain, an OX-40 intracellular co-stimulatory signaling domain, or any combinations thereof. For example, a preferred intracellular co-stimulatory signaling domain comprises or consists of at least a portion of CD28 intracellular co-stimulatory signaling domain, or at least a portion of a 4-1BB (CD137) intracellular co-stimulatory signaling domain. Another preferred intracellular co-stimulatory signaling domain comprises or consists of at least a portion of CD28 intracellular co-stimulatory signaling domain coupled with at least a portion of a 4-1BB (CD137) intracellular co-stimulatory signaling domain. In embodiments, at least a portion of the CD28 intracellular domain comprises or consists of the amino acid sequence of SEQ ID NO:32 or an amino acid sequence at least 80%, 85%, 90%, or 95% identical to SEQ ID NO:32. In embodiments, at least a portion of the CD28 intracellular domain comprises or consists of the amino acid sequence of SEQ ID NO:32 or an amino acid sequence at least 80%, 85%, 90%, or 95% identical to SEQ ID NO:32. In embodiments, at least a portion of the 4-1BB intracellular co-stimulatory signaling domain comprises or consists of the amino acid sequence of SEQ ID NO: 33 or an amino acid sequence at least 80%, 85%, 90%, or 95% identical to SEQ ID NO:33. In embodiments, at least a portion of the 4-1BB intracellular co-stimulatory signaling domain comprises or consists of the amino acid sequence of SEQ ID NO:33 or an amino acid sequence at least 80%, 85%, 90%, or 95% identical to SEQ ID NO:29. In embodiments, the chimeric antigen receptor disclosed herein or the recombinant protein includes an amino acid sequence of a combination of SEQ ID NO: 32 and SEQ ID NO:33 (either SEQ ID NO: 32 present at the N'-terminus of SEQ ID NO: 33, or SEQ ID NO: 33 present at the N'-terminus of SEQ ID NO: 32), or an amino acid sequence at least 80%, 85%, 90%, or 95% identical to a combination of SEQ ID NO: 32 and SEQ ID NO:33 (either SEQ ID NO: 32 present at the N'-terminus of SEQ ID NO: 33, or SEQ ID NO: 33 present at the N'-terminus of SEQ ID NO: 32).

In embodiments, the recombinant protein further includes an intracellular T-cell signaling domain. An "intracellular T-cell signaling domain" as provided herein includes amino acid sequences capable of providing primary signaling in response to binding of an antigen to the antibody region provided herein including embodiments thereof. In embodiments, the signaling of the intracellular T-cell signaling domain results in activation of the T cell expressing the same. In embodiments, the signaling of the intracellular T-cell signaling domain results in proliferation (cell division) of the T cell expressing the same. In embodiments, the signaling of the intracellular T-cell signaling domain results expression by the T cell of proteins known in the art to characteristic of activated T cell (e.g., CTLA-4, PD-1, CD28, CD69). In embodiments, the intracellular T-cell signaling domain is a CD3ζ intracellular T-cell signaling domain. In embodiments, the CD3ζ intracellular T-cell signaling domain includes the amino acid sequence of SEQ ID NO:34 or an amino acid sequence at least 80%, 85%, 90%, or 95% identical to SEQ ID NO: 34 that generates a CD3ζ intracellular T-cell signaling domain having at least 80%, 85%, 90%, or 95% activity of the CD3ζ intracellular T-cell signaling domain having SEQ ID NO:34. In embodiments, the CD3ζ intracellular T-cell signaling domain has the amino acid sequence of SEQ ID NO:34 or a sequence at least 80%, 85%, 90%, or 95% identical to SEQ ID NO:34 that generates a peptide having at least 80%, 85%, 90%, or 95% activity of the CD3ζ intracellular T-cell signaling domain having SEQ ID NO:34.

In embodiments, the ROR-1 CAR disclosed herein includes or consists of i) ROR1 scFv (having CDR L1 (SEQ ID NO:43), CDR L2 (SEQ ID NO:44), and CDR L3 (SEQ ID NO: 45), CDR H1 (SEQ ID NO:46), CDR H2 (SEQ ID NO:47), and CDR H3 (SEQ ID NO:48), or VL domain having the sequence of SEQ ID NO:21, or a sequence at least 80%, 85%, 90%, or 95% identical to SEQ ID NO:21 and the VH domain having the sequence of SEQ ID NO:27, or a sequence at least 80%, 85%, 90%, or 95% identical to SEQ ID NO:27) or alternatively ROR1 scFv (CDR L1 (SEQ ID NO:49), CDR L2 (SEQ ID NO:50), and CDR L3 (SEQ ID NO:51), CDR H1 (SEQ ID NO:52), CDR H2 (SEQ ID NO:53), and CDR H3 (SEQ ID NO:54), or VL domain having the sequence of SEQ ID NO: 19, or a sequence at least 80%, 85%, 90%, or 95% identical to SEQ ID NO:19 and the VH domain having the sequence of SEQ ID NO:20, or a sequence at least 80%, 85%, 90%, or 95% identical to SEQ ID NO:20), ii) a spacer domain having a hinge and CH2 and CH3 domain, iii) CD28 transmembrane domain, iv) 4-1BB (CD137) costimulatory domain, and v) CD3Z T cell activation domain.

Alternatively, in embodiments, the ROR1 CAR disclosed herein includes or consists of i) ROR1 scFv (having CDR L1 (SEQ ID NO:43), CDR L2 (SEQ ID NO:44), and CDR L3 (SEQ ID NO:45), CDR H1 (SEQ ID NO:46), CDR H2 (SEQ ID NO:47), and CDR H3 (SEQ ID NO: 48), or VL domain having the sequence of SEQ ID NO:21, or a sequence at least 80%, 85%, 90%, or 95% identical to SEQ ID NO:21 and the VH domain having the sequence of SEQ ID NO: 27, or a sequence at least 80%, 85%, 90%, or 95% identical to SEQ ID NO:27) or alternatively ROR1 scFv (CDR L1 (SEQ ID NO:49), CDR L2 (SEQ ID NO:50), and CDR L3 (SEQ ID NO:51), CDR H1 (SEQ ID NO:52), CDR H2 (SEQ ID NO:53), and CDR H3 (SEQ ID NO: 54), or VL domain having the sequence of SEQ ID NO:19, or a sequence at least 80%, 85%, 90%, or 95% identical to SEQ ID NO:19 and the VH domain having the sequence of SEQ ID NO: 20, or a sequence at least 80%, 85%, 90%, or 95% identical to SEQ ID NO:20), ii) a spacer domain having a hinge and CH2 domain, iii) CD28 transmembrane domain, iv) 4-1BB (CD137) costimulatory domain, and v) CD3Z T cell activation domain.

Alternatively, in embodiments, the ROR1 CAR disclosed herein includes or consists of i) ROR1 scFv (having CDR L1 (SEQ ID NO:43), CDR L2 (SEQ ID NO:44), and CDR L3 (SEQ ID NO:45), CDR H1 (SEQ ID NO:46), CDR H2 (SEQ ID NO:47), and CDR H3 (SEQ ID NO: 48), or VL domain having the sequence of SEQ ID NO:21, or a sequence at least 80%, 85%, 90%, or 95% identical to SEQ ID NO:21 and the VH domain having the sequence of SEQ ID NO: 27, or a sequence at least 80%, 85%, 90%, or 95% identical to SEQ ID NO:27) or alternatively ROR1 scFv (CDR L1 (SEQ ID NO:49), CDR L2 (SEQ ID NO:50), and CDR L3 (SEQ ID NO:51), CDR H1 (SEQ ID NO:52), CDR H2 (SEQ ID NO:53), and CDR H3 (SEQ ID NO: 54), or VL domain having the sequence of SEQ ID NO:19, or a sequence at least 80%, 85%, 90%, or 95% identical to SEQ ID NO:19 and the VH domain having the sequence of SEQ ID NO: 20, or a sequence at least 80%, 85%, 90%, or 95% identical to SEQ ID NO:20), ii) a spacer domain having a hinge and CH3 domain, iii) CD28 transmembrane domain, iv) 4-1BB (CD137) costimulatory domain, and v) CD3Z T cell activation domain.

Alternatively, in embodiments, the ROR1 CAR disclosed herein includes or consists of i) ROR1 scFv (having CDR L1 (SEQ ID NO:43), CDR L2 (SEQ ID NO:44), and CDR L3 (SEQ ID NO:45), CDR H1 (SEQ ID NO:46), CDR H2 (SEQ ID NO:47), and CDR H3 (SEQ ID NO: 48), or VL domain having the sequence of SEQ ID NO:21, or a sequence at least 80%, 85%, 90%, or 95% identical to SEQ ID NO:21 and the VH domain having the sequence of SEQ ID NO: 27, or a sequence at least 80%, 85%, 90%, or 95% identical to SEQ ID NO:27) or alternatively ROR1 scFv (CDR L1 (SEQ ID NO:49), CDR L2 (SEQ ID NO:50), and CDR L3 (SEQ ID NO:51), CDR H1 (SEQ ID NO:52), CDR H2 (SEQ ID NO:53), and CDR H3 (SEQ ID NO: 54), or VL domain having the sequence of SEQ ID NO:19, or a sequence at least 80%, 85%, 90%, or 95% identical to SEQ ID NO:19 and the VH domain having the sequence of SEQ ID NO: 20, or a sequence at least 80%, 85%, 90%, or 95% identical to SEQ ID NO:20), ii) a spacer domain having a hinge and a portion of CH3 domain (e.g., a half of CH3 domain, N-terminal 43 amino acids of CH3 domain, etc.), iii) CD28 transmembrane domain, iv) 4-1BB (CD137) costimulatory domain, and v) CD3Z T cell activation domain.

Alternatively, in embodiments, the ROR1 CAR disclosed herein includes or consists of i) ROR1 scFv (having CDR L1 (SEQ ID NO:43), CDR L2 (SEQ ID NO:44), and CDR L3 (SEQ ID NO:45), CDR H1 (SEQ ID NO:46), CDR H2 (SEQ ID NO:47), and CDR H3 (SEQ ID NO: 48), or VL domain having the sequence of SEQ ID NO:21, or a sequence at least 80%, 85%, 90%, or 95% identical to SEQ ID NO:21 and the VH domain having the sequence of SEQ ID NO: 27, or a sequence at least 80%, 85%, 90%, or 95% identical to SEQ ID NO:27) or alternatively ROR1 scFv (CDR L1 (SEQ ID NO:49), CDR L2 (SEQ ID NO:50), and CDR L3 (SEQ ID NO:51), CDR H1 (SEQ ID NO:52), CDR H2 (SEQ ID NO:53), and CDR H3 (SEQ ID NO: 54), or VL domain having the sequence of SEQ ID NO:19, or a sequence at least 80%, 85%, 90%, or 95% identical to SEQ ID NO:19 and the VH domain having the sequence of SEQ ID NO: 20, or a sequence at least 80%, 85%, 90%, or 95% identical to SEQ ID NO:20), ii) a spacer domain having a hinge domain, iii) CD28 transmembrane domain, iv) 4-1BB (CD137) costimulatory domain, and v) CD3Z T cell activation domain.

Consequently, in embodiments, the ROR1 CAR disclosed herein includes or consists of i) ROR1 scFv (having CDR L1 (SEQ ID NO:43), CDR L2 (SEQ ID NO:44), and CDR L3 (SEQ ID NO:45), CDR H1 (SEQ ID NO:46), CDR H2 (SEQ ID NO:47), and CDR H3 (SEQ ID NO: 48), or VL domain having the sequence of SEQ ID NO:21, or a sequence at least 80%, 85%, 90%, or 95% identical to SEQ ID NO:21 and the VH domain having the sequence of SEQ ID NO: 27, or a sequence at least 80%, 85%, 90%, or 95% identical to SEQ ID NO:27) or alternatively ROR1 scFv (CDR L1 (SEQ ID NO:49), CDR L2 (SEQ ID NO:50), and CDR L3 (SEQ ID NO:51), CDR H1 (SEQ ID NO:52), CDR H2 (SEQ ID NO:53), and CDR H3 (SEQ ID NO: 54), or VL domain having the sequence of SEQ ID NO:19, or a sequence at least 80%, 85%, 90%, or 95% identical to SEQ ID NO:19 and the VH domain having the sequence of SEQ ID NO: 20, or a sequence at least 80%, 85%, 90%, or 95% identical to SEQ ID NO:20), ii) a spacer domain having a hinge and CH2 and CH3 domain, iii) CD28 transmembrane domain, iv) CD28 costimulatory domain coupled to 4-1BB (CD137) costimulatory domain, and v) CD3Z T cell activation domain.

Alternatively, in embodiments, the ROR-1 CAR disclosed herein includes or consists of i) ROR1 scFv (having CDR L1 (SEQ ID NO:43), CDR L2 (SEQ ID NO:44), and CDR L3 (SEQ ID NO:45), CDR H1 (SEQ ID NO:46), CDR H2 (SEQ ID NO:47), and CDR H3 (SEQ ID NO: 48), or VL domain having the sequence of SEQ ID NO:21, or a sequence at least 80%, 85%, 90%, or 95% identical to SEQ ID NO:21 and the VH domain having the sequence of SEQ ID NO: 27, or a sequence at least 80%, 85%, 90%, or 95% identical to SEQ ID NO:27) or alternatively ROR1 scFv (CDR L1 (SEQ ID NO:49), CDR L2 (SEQ ID NO:50), and CDR L3 (SEQ ID NO:51), CDR H1 (SEQ ID NO:52), CDR H2 (SEQ ID NO:53), and CDR H3 (SEQ ID NO: 54), or VL domain having the sequence of SEQ ID NO:19, or a sequence at least 80%, 85%, 90%, or 95% identical to SEQ ID NO:19 and the VH domain having the sequence of SEQ ID NO: 20, or a sequence at least 80%, 85%, 90%, or 95% identical to SEQ ID NO:20), ii) a spacer domain having a hinge and CH2 domain, iii) CD28 transmembrane domain, iv) CD28 costimulatory domain coupled to 4-1BB (CD137) costimulatory domain, and v) CD3Z T cell activation domain.

Alternatively, in embodiments, the ROR-1 CAR disclosed herein includes or consists of i) ROR1 scFv (having CDR L1 (SEQ ID NO:43), CDR L2 (SEQ ID NO:44), and CDR L3 (SEQ ID NO:45), CDR H1 (SEQ ID NO:46), CDR H2 (SEQ ID NO:47), and CDR H3 (SEQ ID NO: 48), or VL domain having the sequence of SEQ ID NO:21, or a sequence at least 80%, 85%, 90%, or 95% identical to SEQ ID NO:21 and the VH domain having the sequence of SEQ ID NO: 27, or a sequence at least 80%, 85%, 90%, or 95% identical to SEQ ID NO:27) or alternatively ROR1 scFv (CDR L1 (SEQ ID NO:49), CDR L2 (SEQ ID NO:50), and CDR L3 (SEQ ID NO:51), CDR H1 (SEQ ID NO:52), CDR H2 (SEQ ID NO:53), and CDR H3 (SEQ ID NO: 54), or VL domain having the sequence of SEQ ID NO:19, or a sequence at least 80%, 85%, 90%, or 95% identical to SEQ ID NO:19 and the VH domain having the sequence of SEQ ID NO: 20, or a sequence at least 80%, 85%, 90%, or 95% identical to SEQ ID NO:20), ii) a spacer domain having a hinge and CH3 domain, iii) CD28 transmembrane domain, iv) CD28 costimulatory domain coupled to 4-1BB (CD137) costimulatory domain, and v) CD3Z T cell activation domain.

Alternatively, in embodiments, the ROR-1 CAR disclosed herein includes or consists of i) ROR1 scFv (having CDR L1 (SEQ ID NO:43), CDR L2 (SEQ ID NO:44), and CDR L3 (SEQ ID NO:45), CDR H1 (SEQ ID NO:46), CDR H2 (SEQ ID NO:47), and CDR H3 (SEQ ID NO: 48), or VL domain having the sequence of SEQ ID NO:21, or a sequence at least 80%, 85%, 90%, or 95% identical to SEQ ID NO:21 and the VH domain having the sequence of SEQ ID NO: 27, or a sequence at least 80%, 85%, 90%, or 95% identical to SEQ ID NO:27) or alternatively ROR1 scFv (CDR L1 (SEQ ID NO:49), CDR L2 (SEQ ID NO:50), and CDR L3 (SEQ ID NO:51), CDR H1 (SEQ ID NO:52), CDR H2 (SEQ ID NO:53), and CDR H3 (SEQ ID NO: 54), or VL domain having the sequence of SEQ ID NO:19, or a sequence at least 80%, 85%, 90%, or 95% identical to SEQ ID NO:19 and the VH domain having the sequence of SEQ ID NO: 20, or a sequence at least 80%, 85%, 90%, or 95% identical to SEQ ID NO:20), ii) a spacer domain having a hinge and a portion of CH3 domain (e.g., a half of CH3 domain, N-terminal 43 amino acids of CH3 domain, etc.), iii) CD28 transmembrane domain, iv) CD28 costimulatory domain coupled to 4-1BB (CD137) costimulatory domain, and v) CD3Z T cell activation domain.

Alternatively, in embodiments, the ROR-1 CAR disclosed herein includes or consists of i) ROR1 scFv (having CDR L1 (SEQ ID NO:43), CDR L2 (SEQ ID NO:44), and CDR L3 (SEQ ID NO:45), CDR H1 (SEQ ID NO:46), CDR H2 (SEQ ID NO:47), and CDR H3 (SEQ ID NO: 48), or VL domain having the sequence of SEQ ID NO:21, or a sequence at least 80%, 85%, 90%, or 95% identical to SEQ ID NO:21 and the VH domain having the sequence of SEQ ID NO: 27, or a sequence at least 80%, 85%, 90%, or 95% identical to SEQ ID NO:27) or alternatively ROR1 scFv (CDR L1 (SEQ ID NO:49), CDR L2 (SEQ ID NO:50), and CDR L3 (SEQ ID NO:51), CDR H1 (SEQ ID NO:52), CDR H2 (SEQ ID NO:53), and CDR H3 (SEQ ID NO: 54), or VL domain having the sequence of SEQ ID NO:19, or a sequence at least 80%, 85%, 90%, or 95% identical to SEQ ID NO:19 and the VH domain having the sequence of SEQ ID NO: 20, or a sequence at least 80%, 85%, 90%, or 95% identical to SEQ ID NO:20), ii) a spacer domain having a hinge domain, iii) CD28 transmembrane domain, iv) CD28 costimulatory domain coupled to 4-1BB (CD137) costimulatory domain, and v) CD3Z T cell activation domain.

It is contemplated that the chimeric antigen receptor described here binds to amino acids 130-160 of ROR-1 or a fragment thereof, preferably to a peptide including a glutamic acid at a position corresponding to position 138 of ROR-1 polypeptide. Alternatively and/or additionally, the chimeric antigen receptor described herein specifically binds either the 3' or middle Ig-like region of the extracellular domain of the ROR-1 protein, preferably to 3' end of the Ig-like region of the extracellular domain of ROR-1 protein from position 1-147.

Consequently, the ROR-1 CAR disclosed herein binds to a ROR-1 expressing cells and can initiate or induce immune response against the ROR-1 expressing cells, including a cancer cell, such as leukemia cell, a lymphoma cell, a chronic lymphocytic leukemia (CLL) cell, an adult acute myeloid leukemia (AML) cell, an acute lymphoblastic leukemia (ALL) cell, a mantle cell lymphoma cell, an ovarian cancer cell, a colon cancer cell, a lung cancer cell, a skin cancer cell, a pancreatic cancer cell, a testicular cancer cell, a bladder cancer cell, a uterine cancer cell, a prostate cancer cell, or an adrenal cancer cell, wherein the recombinant protein forms part of a cell.

In embodiments, the recombinant protein provided herein, including embodiments thereof, further includes a detectable domain. A "detectable domain" as provided herein is a peptide moiety detectable by spectroscopic, photochemical, biochemical, immunochemical, chemical, or other physical means. For example, a detectable domain as provided herein may be a protein or other entity which can be made detectable, e.g., by incorporating a radiolabel or being reactive to an antibody specifically. Any appropriate method known in the art for conjugating an antibody to the label may be employed, e.g., using methods described in Hermanson, Bioconjugate Techniques 1996, Academic Press, Inc., San Diego. In the present invention, a detectable domain is used to confirm transfection of T cells.

In embodiments, the recombinant protein or chimeric antigen receptor has a binding affinity of about 500 pM to about 6 nM. In embodiments, the recombinant protein or chimeric antigen receptor has a binding affinity of about 550 pM to about 6 nM. In embodiments, the recombinant protein or chimeric antigen receptor has a binding affinity of about 600 pM to about 6 nM. In embodiments, the recombinant protein or chimeric antigen receptor has a binding affinity of about 650 pM to about 6 nM. In embodiments, the recombinant protein or chimeric antigen receptor has a binding affinity of about 700 pM to about 6 nM. In embodiments, the recombinant protein or chimeric antigen receptor has a binding affinity of about 750 pM to about 6 nM. In embodiments, the recombinant protein or chimeric antigen receptor has a binding affinity of about 800 pM to about 6 nM. In embodiments, the recombinant protein or chimeric antigen receptor has a binding affinity of about 850 pM to about 6 nM. In embodiments, the recombinant protein or chimeric antigen receptor has a binding affinity of about 900 pM to about 6 nM. In embodiments, the recombinant protein or chimeric antigen receptor has a binding affinity of about 950 pM to about 6 nM. In embodiments, the recombinant protein or chimeric antigen receptor has a binding affinity of about 1 nM to about 6 nM. In embodiments, the recombinant protein or chimeric antigen receptor has a binding affinity of about 1 nM to about 6 nM. In embodiments, the recombinant protein or chimeric antigen receptor has a binding affinity of about 1.5 nM to about 6 nM. In embodiments, the recombinant protein or chimeric antigen receptor has a binding affinity of about 2 nM to about 6 nM. In embodiments, the recombinant protein or chimeric antigen receptor has a binding affinity of about 2.5 nM to about 6 nM. In embodiments, the recombinant protein or chimeric antigen receptor has a binding affinity of about 3 nM to about 6 nM. In embodiments, the recombinant protein or chimeric antigen receptor has a binding affinity of about 3.5 nM to about 6 nM. In embodiments, the recombinant protein or chimeric antigen receptor has a binding affinity of about 4 nM to about 6 nM. In embodiments, the recombinant protein or chimeric antigen receptor has a binding affinity of about 4.5 nM to about 6 nM. In embodiments, the recombinant protein or chimeric antigen receptor has a binding affinity of about 5 nM to about 6 nM. In embodiments, the recombinant protein or chimeric antigen receptor has a binding affinity of about 5.5 nM to about 6 nM.

In embodiments, the recombinant protein or chimeric antigen receptor has a binding affinity of about 500 pM. In embodiments, the recombinant protein or chimeric antigen receptor has a binding affinity of 500 pM. In embodiments, the recombinant protein or chimeric antigen receptor has a binding affinity of about 550 pM. In embodiments, the recombinant protein or chimeric antigen receptor has a binding affinity of 550 pM. In embodiments, the recombinant protein or chimeric antigen receptor has a binding affinity of about 600 pM. In embodiments, the recombinant protein or chimeric antigen receptor has a binding affinity of 600 pM. In embodiments, the recombinant protein or chimeric antigen receptor has a binding affinity of about 650 pM. In embodiments, the recombinant protein or chimeric antigen receptor has a binding affinity of 650 pM. In embodiments, the recombinant protein or chimeric antigen receptor has a binding affinity of about 700 pM. In embodiments, the recombinant protein or chimeric antigen receptor has a binding affinity of 700 pM. In embodiments, the recombinant protein or chimeric antigen receptor has a binding affinity of about 750 pM. In embodiments, the recombinant protein or chimeric antigen receptor has a binding affinity of 750 pM. In embodiments, the recombinant protein or chimeric antigen receptor has a binding affinity of about 800 pM. In embodiments, the recombinant protein or chimeric antigen receptor has a binding affinity of 800 pM. In embodiments, the recombinant protein or chimeric antigen receptor has a binding affinity of about 850 pM. In embodiments, the recombinant protein or chimeric antigen receptor has a binding affinity of 850 pM. In embodiments, the recombinant protein or chimeric antigen receptor has a binding affinity of about 900 pM. In embodiments, the recombinant protein or chimeric antigen receptor has a binding affinity of 900 pM. In embodiments, the recombinant protein or chimeric antigen receptor has a binding affinity of about 950 pM. In embodiments, the recombinant protein or chimeric antigen receptor has a binding affinity of 950 pM. In embodiments, the recombinant protein or chimeric antigen receptor has a binding affinity of about 1 nM. In embodiments, the recombinant protein or chimeric antigen receptor has a binding affinity of about 1 nM. In embodiments, the recombinant protein or chimeric antigen receptor has a binding affinity of 1 nM. In embodiments, the recombinant protein or chimeric antigen receptor has a binding affinity of about 1.5 nM. In embodiments, the recombinant protein or chimeric antigen receptor has a binding affinity of 1.5 nM. In embodiments, the recombinant protein or chimeric antigen receptor has a binding affinity of about 2 nM. In embodiments, the recombinant protein or chimeric antigen receptor has a binding affinity of 2 nM. In embodiments, the recombinant protein or chimeric antigen receptor has a binding affinity of about 2.5 nM. In embodiments, the recombinant protein or chimeric antigen receptor has a binding affinity of 2.5 nM. In embodiments, the recombinant protein or chimeric antigen receptor has a binding affinity of about 3 nM. In embodiments, the recombinant protein or chimeric antigen receptor has a binding affinity of 3 nM. In embodiments, the recombinant protein or chimeric antigen receptor has a binding affinity of about 3.5 nM. In embodiments, the recombinant protein or chimeric antigen receptor has a binding affinity of 3.5 nM. In embodiments, the recombinant protein or chimeric antigen receptor has a binding affinity of about 4 nM. In embodiments, the recombinant protein or chimeric antigen receptor has a binding affinity of 4 nM. In embodiments, the recombinant protein or chimeric antigen receptor has a binding affinity of about 4.5 nM. In embodiments, the recombinant protein or chimeric antigen receptor has a binding affinity of 4.5 nM. In embodiments, the recombinant protein or chimeric antigen receptor has a binding affinity of about 5 nM. In embodiments, the recombinant protein or chimeric antigen receptor has a binding affinity of 5 nM. In embodiments, the recombinant protein or chimeric antigen receptor has a binding affinity of about 5.5 nM. In embodiments, the recombinant protein or chimeric antigen receptor has a binding affinity of 5.5 nM. In embodiments, the recombinant protein or chimeric antigen receptor has a binding affinity of about 6 nM. In embodiments, the recombinant protein or chimeric antigen receptor has a binding affinity of 6 nM.

In embodiments, the recombinant protein or chimeric antigen receptor binds to an ROR-1 protein with a $K_D$ of less than about 40 nM (e.g., 35, 30, 25, 20, 15, 10, 9, 8, 7, 6, 5, 4, 3, 2, 1, 0.5, 0.25, 0.1 nM). In embodiments, the recombinant protein or chimeric antigen receptor binds to an ROR-1 protein with a $K_D$ of less than 40 nM (e.g., 35, 30, 25, 20, 15, 10, 9, 8, 7, 6, 5, 4, 3, 2, 1, 0.5, 0.25, 0.1 nM). In embodiments, the recombinant protein or chimeric antigen receptor binds to an ROR-1 protein with a $K_D$ of less than about 35 nM. In embodiments, the recombinant protein or chimeric antigen receptor binds to an ROR-1 protein with a $K_D$ of less than 35 nM. In embodiments, the recombinant protein or chimeric antigen receptor binds to an ROR-1 protein with a $K_D$ of less than about 30 nM. In embodiments, the recombinant protein or chimeric antigen receptor binds to an ROR-1 protein with a $K_D$ of less than 30 nM. In embodiments, the recombinant protein or chimeric antigen receptor binds to an ROR-1 protein with a $K_D$ of less than about 25 nM. In embodiments, the recombinant protein or chimeric antigen receptor binds to an ROR-1 protein with a $K_D$ of less than 25 nM. In embodiments, the recombinant protein or chimeric antigen receptor binds to an ROR-1 protein with a $K_D$ of less than about 20 nM. In embodiments, the recombinant protein or chimeric antigen receptor binds to an ROR-1 protein with a $K_D$ of less than 20 nM. In embodiments, the recombinant protein or chimeric antigen receptor binds to an ROR-1 protein with a $K_D$ of less than about 15 nM. In embodiments, the recombinant protein or chimeric antigen receptor binds to an ROR-1 protein with a $K_D$ of less than 15 nM. In embodiments, the recombinant protein or chimeric antigen receptor binds to an ROR-1 protein with a $K_D$ of less than about 10 nM. In embodiments, the recombinant protein or chimeric antigen receptor binds to an ROR-1 protein with a $K_D$ of less than 10 nM. In embodiments, the recombinant protein or chimeric antigen receptor binds to an ROR-1 protein with a $K_D$ of less than about 9 nM. In embodiments, the recombinant protein or chimeric antigen receptor binds to an ROR-1 protein with a $K_D$ of less than 9 nM. In embodiments, the recombinant protein or chimeric antigen receptor binds to an ROR-1 protein with a $K_D$ of less than about 8 nM. In embodiments, the recombinant protein or chimeric antigen receptor binds to an ROR-1 protein with a $K_D$ of less than 8 nM. In embodiments, the recombinant protein or chimeric antigen receptor binds to an ROR-1 protein with a $K_D$ of less than about 7 nM. In embodiments, the recombinant protein or chimeric antigen receptor binds to an ROR-1 protein with a $K_D$ of less than 7 nM. In embodiments, the recombinant protein or chimeric antigen receptor binds to an ROR-1 protein with a $K_D$ of less than about 6 nM. In embodiments, the recombinant protein or chimeric antigen receptor binds to an ROR-1 protein with a $K_D$ of less than 6 nM. In embodiments, the recombinant protein or chimeric antigen receptor binds to an ROR-1 protein with a $K_D$ of less than about 5 nM. In embodiments, the recombinant protein or chimeric antigen receptor binds to an ROR-1 protein with a $K_D$ of less than 5 nM. In embodiments, the recombinant protein or chimeric antigen receptor binds to an ROR-1 protein with a $K_D$ of less than about 4 nM. In embodiments, the recombinant protein or chimeric antigen receptor binds to an ROR-1 protein with a $K_D$ of less than 4 nM. In embodiments, the recombinant protein or chimeric antigen receptor binds to an ROR-1 protein with a $K_D$ of less than about 3 nM. In embodiments, the recombinant protein or chimeric antigen receptor binds to an ROR-1 protein with a $K_D$ of less than 3 nM. In embodiments, the recombinant protein or chimeric antigen receptor binds to an ROR-1 protein with a $K_D$ of less than about 2 nM. In embodiments, the recombinant protein or chimeric antigen receptor binds to an ROR-1 protein with a $K_D$ of less than 2 nM. In embodiments, the recombinant protein or chimeric antigen receptor binds to an ROR-1 protein with a $K_D$ of less than about 1 nM. In embodiments, the recombinant protein or chimeric antigen receptor binds to an ROR-1 protein with a $K_D$ of less than 1 nM. In embodiments, the recombinant protein or chimeric antigen receptor binds to an ROR-1 protein with a $K_D$ of less than about 0.5 nM. In embodiments, the recombinant protein or chimeric antigen receptor binds to an ROR-1 protein with a $K_D$ of less than 0.5 nM. In embodiments, the recombinant protein or chimeric antigen receptor binds to an ROR-1 protein with a $K_D$ of less than about 0.25 nM. In embodiments, the recombinant protein or chimeric antigen receptor binds to an ROR-1 protein with a $K_D$ of less than 0.25 nM. In embodiments, the recombinant protein or chimeric antigen receptor binds to an ROR-1 protein with a $K_D$ of less than about 0.1 nM. In embodiments, the recombinant protein or chimeric antigen receptor binds to an ROR-1 protein with a $K_D$ of less than 0.1 nM.

It is contemplated that the chimeric antigen receptor described herein is expressed on the surface of T lymphocytes or T cells (e.g., e.g., CD8+ T cells, CD4+ T cells) by genetically engineering the T cells to express the heterologous nucleic acid sequences encoding the chimeric nucleic acid receptor. Such generated CAR-T cells specifically bind to ROR-1-expressing cells, preferably, ROR1 expressing cancer cells, to elicit an immune response against the ROR-1 expressing cancer cells. In some embodiments, the chimeric antigen receptor described herein is expressed on the surface of natural killer cells (NK cells or genetically modified or engineered NK cells). In certain embodiments, the NK cells are CD56 positive cells. CD56 positivity can be determined by for example flow cytometry analysis of a cell population and defined as cells at least 10×, 100×, or 1,000× compared to cells stained with an isotype control antibody. In certain embodiments, the NK cells are primary NK cells. In certain embodiments, the NK cells comprise an NK cell line. In certain embodiments, the NK cells are autologous to an individual being treated with a CAR expressing NK cell of this disclosure. In certain embodiments, the NK cells are heterologous to an individual being treated with a CAR expressing NK cell of this disclosure. In certain embodiments, the NK cells are allogeneic to an individual being treated with a CAR expressing NK cell of this disclosure. NK cells can be derived from any suitable source bone marrow, induced pluripotent stem cells, peripheral blood mononuclear cells, fetal or placental cells.

Further provided herein are recombinant nucleic acids encoding the recombinant protein or chimeric antigen receptor provided herein including embodiments thereof. In some embodiments, the chimeric antigen receptor is encoded by a single recombinant nucleic acid that forms part of an expression vector. Any suitable expression vector that is capable of being transfected into and expressed in an immune cells (e.g., CD8+ T cells, CD4+ T cells, CD56+ immune cells, NK cells, or genetically modified or engineered NK cells) are contemplated. Exemplary and/or preferred expression vectors may include a viral expression vector (e.g., expression vectors for adenovirus, adeno-associated viruses, alphaviruses, herpes viruses, lentiviruses, etc.). In some embodiments, an adenovirus is a replication deficient and non-immunogenic virus, which is typically accomplished by targeted deletion of selected viral proteins (e.g., E1, E2b, E3 proteins). For example, the recombinant nucleic acid can be placed in a non-viral vector (e.g., mammalian expression vector) and transfected to the T cells using any generally used transfection method. For other example, the recombinant nucleic acid in a viral vector such that the viral particle including recombinant nucleic acid infect the T cells to deliver the recombinant nucleic acid into the T cells. For still other example, where the recombinant nucleic acid is a self-replicating RNA-based vector, self-replicating RNA-based vector can be formulated with a pharmaceutically acceptable carrier (e.g., in a buffer or cell culture medium, preferably with RNAase inhibitors)) such that the self-replicating RNA-based vector can be delivered in a naked form to the cell by contacting directly to the cell membrane. In some embodiments, the self-replicating RNA-based vector can be coupled to a carrier molecule. Exemplary carrier molecules includes protein A, protein G, protein Z, albumin, refolded albumin, a nanoparticle (e.g., quantum dots, gold nanoparticles, magnetic nanoparticles, nanotubes, polymeric nanoparticles, dendrimers, etc.), or a bead (e.g., polystyrene bead, latex bead, dynabead, etc.). Preferably, the nanoparticle and/or beads have a dimension below 1 μm, preferably below 100 nm. In other embodiments, the self-replicating RNA-based vector can be coupled with a micro particle (e.g., PLG RG503 (50:50 lactide/glycolide molar ratio), where the self-replicating RNA-based vector can be absorbed to the micro particle for further delivery to the cell. In still other embodiments, the self-replicating RNA-based vector can be encapsulated in a liposome (e.g., PEG-based liposome, etc.) to protect the self-replicating RNA-based vector from RNAase digestion and deliver the RNA-based vector by fusing the liposome to the target cell membrane.

In embodiments, the recombinant nucleic acids encoding the recombinant protein or chimeric antigen receptor provided herein can be inserted into a vector having a cassette for gene editing (e.g., CRISPR-CAS expression vector). Another exemplary expression vectors may include transposon-based expression system (e.g., Sleeping Beauty system, as disclosed in Deninger et al., PLOS ONE, Jun. 1, 2015).

Pharmaceutical Compositions

The immune cells expressing chimeric antigen receptor(s) and/or the recombinant nucleic acid encoding the chimeric antigen receptor(s) may further formulated as a pharmaceutical composition, optionally with any pharmaceutically acceptable carrier (e.g., as a sterile injectable composition for immune cells expressing chimeric antigen receptor(s), a pharmaceutically acceptable salt for recombinant nucleic acid encoding the chimeric antigen receptor(s), etc.). While the dose or cell titer of the pharmaceutical composition may vary depending on the treatment protocols, treatment regimens, treatment conditions, etc., one example of the dose or cell titer of the pharmaceutical composition may include a cell titer of at least $1\times10^3$ cells/ml, preferably at least $1\times10^5$ cells/ml, more preferably at least $1\times10^6$ cells/ml, and at least 1 ml, preferably at least 5 ml, more preferably and at least 20 ml per dosage unit.

In some embodiments, the pharmaceutical composition may include a homogenous cell or plurality thereof (e.g., CD8+ T cells expressing the chimeric antigen receptor, CD4+ T cells expressing the chimeric antigen receptor NK cells expressing the chimeric antigen receptor, etc.). In other embodiments, the composition can comprise a mixture of heterogeneous cells (e.g., mixture of CD8+ T cells expressing the chimeric antigen receptor and NK cells expressing the chimeric antigen receptor, etc., in a ratio of 1:1, 1:2, 1:3, 1:4, 4:1, 3:1, 2:1, etc.). In this pharmaceutical composition, the ratio of different types of cells may vary based on the type of cancer, age, gender, or health status of the patient, size of tumor, and the cell counts of the patient. The actual amount effective for a particular application will depend, inter alia, on the condition being treated. When administered in methods to treat a disease, the recombinant proteins described herein will contain an amount of active ingredient effective to achieve the desired result, e.g., modulating the activity of a target molecule, and/or reducing, eliminating, or slowing the progression of disease symptoms. Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer and severity of such symptoms), kind of concurrent treatment, complications from the disease being treated or other health-related problems. Other therapeutic regimens or agents can be used in conjunction with the methods and compounds of the invention. Adjustment and manipulation of established dosages (e.g., frequency and duration) are well within the ability of those skilled in the art.

For any composition (e.g., recombinant protein, nucleic acid) provided herein, the therapeutically effective amount can be initially determined from cell culture assays. Target concentrations will be those concentrations of active compound(s) that are capable of achieving the methods described herein, as measured using the methods described herein or known in the art. As is well known in the art, effective amounts for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred "Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The pharmaceutical preparation is optionally in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The unit dosage form can be of a frozen dispersion.

Methods of Treatment

The CAR-T cell compositions described herein are useful for treating a cancer or a tumor in an individual. Thus, described herein is a method of treating cancer in a subject in need thereof. The method includes administering to a subject a therapeutically effective amount of a CAR-T cell provided herein including embodiments thereof, thereby treating the cancer or tumor in the subject. CAR T-cell compositions are generally administered with one or more pharmaceutically acceptable excipients, carriers, or diluents.

In certain embodiments, disclosed herein, are anti-ROR-1 CAR T-cells and anti-ROR-1 CAR-T cell compositions useful for the treatment of a cancer or tumor. Treatment refers to a method that seeks to improve or ameliorate the condition being treated. With respect to cancer, treatment includes, but is not limited to, reduction of tumor volume, reduction in growth of tumor volume, increase in progression-free survival, or overall life expectancy. In certain embodiments, treatment will effect remission of a cancer being treated. In certain embodiments, treatment encompasses use as a prophylactic or maintenance dose intended to prevent reoccurrence or progression of a previously treated cancer or tumor. It is understood by those of skill in the art that not all individuals will respond equally or at all to a treatment that is administered, nevertheless these individuals are considered to be treated.

In certain embodiments, the cancer or tumor treated using the anti ROR-1 CAR-T cells described herein is a solid cancer or tumor. In certain embodiments, the cancer or tumor is a blood cancer or tumor. In certain embodiments, the blood cancer is a leukemia or lymphoma. In certain embodiments, the leukemia or lymphoma comprises a B cell leukemia, lymphoma, chronic lymphocytic leukemia (CLL), acute myelogenous leukemia (AML), multiple myeloma, B cell lymphoblastic acute lymphoblastic leukemia (B-ALL), mantle cell lymphoma (MCL), T cell lymphoblastic acute lymphoblastic leukemia T-ALL, and combinations thereof. In certain embodiments, the solid cancer/tumor comprises ovarian cancer, colon cancer, lung cancer, breast cancer, skin cancer, pancreatic cancer, testicular cancer, bladder cancer, uterine cancer, prostate cancer, adrenal cancer, and combinations thereof. In certain embodiments, the cancer is relapsed or is refractory to at least one other treatment.

In certain embodiments, the anti-ROR-1 CAR T-cells and anti-ROR-1 CAR-T cell compositions can be administered to a subject in need thereof by any route suitable for the administration of cell-containing pharmaceutical compositions, such as, for example, subcutaneous, intraperitoneal, intravenous, intramuscular, intratumoral, or intracerebral, etc. In certain embodiments, the antibodies are administered intravenously. In certain embodiments, the antibodies are administered subcutaneously. In certain embodiments, the antibodies are administered intratumoral.

The anti-ROR-1 CAR T-cells and anti-ROR-1 CAR-T cell compositions can be administered according to a suitable dosage schedule. In certain embodiments, the CAR T-cells are administered once, with subsequent doses depending on clinical criteria. If an individual does not respond or only partially responds said patient can have an anti-ROR-1 CAR-T cell composition administered a second, third, or fourth time until the desired clinical response is observed. A dosage of CAR-T cells will generally comprise at least $1\times10^6$ cells, but no more than $5\times10^8$ cells. Cells can be administered based upon a total amount of an individual's viable PBMC that were transduced with a CAR construct. In certain embodiments, a single dosage comprises 1 million transduced PBMCs to 100 million transduced PBMCs. In certain embodiments, a single dosage comprises 1 million transduced PBMCs to 2 million transduced PBMCs, 1 million transduced PBMCs to 3 million transduced PBMCs, 1 million transduced PBMCs to 4 million transduced PBMCs, 1 million transduced PBMCs to 5 million transduced PBMCs, 1 million transduced PBMCs to 6 million transduced PBMCs, 1 million transduced PBMCs to 7 million transduced PBMCs, 1 million transduced PBMCs to 8 million transduced PBMCs, 1 million transduced PBMCs to 9 million transduced PBMCs, 1 million transduced PBMCs to 10 million transduced PBMCs, 1 million transduced PBMCs to 50 million transduced PBMCs, 1 million transduced PBMCs to 100 million transduced PBMCs, 2 million transduced PBMCs to 3 million transduced PBMCs, 2 million transduced PBMCs to 4 million transduced PBMCs, 2 million transduced PBMCs to 5 million transduced PBMCs, 2 million transduced PBMCs to 6 million transduced PBMCs, 2 million transduced PBMCs to 7 million transduced PBMCs, 2 million transduced PBMCs to 8 million transduced PBMCs, 2 million transduced PBMCs to 9 million transduced PBMCs, 2 million transduced PBMCs to 10 million transduced PBMCs, 2 million transduced PBMCs to 50 million transduced PBMCs, 2 million transduced PBMCs to 100 million transduced PBMCs, 3 million transduced PBMCs to 4 million transduced PBMCs, 3 million transduced PBMCs to 5 million transduced PBMCs, 3 million transduced PBMCs to 6 million transduced PBMCs, 3 million transduced PBMCs to 7 million transduced PBMCs, 3 million transduced PBMCs to 8 million transduced PBMCs, 3 million transduced PBMCs to 9 million transduced PBMCs, 3 million transduced PBMCs to 10 million transduced PBMCs, 3 million transduced PBMCs to 50 million transduced PBMCs, 3 million transduced PBMCs to 100 million transduced PBMCs, 4 million transduced PBMCs to 5 million transduced PBMCs, 4 million transduced PBMCs to 6 million transduced PBMCs, 4 million transduced PBMCs to 7 million transduced PBMCs, 4 million transduced PBMCs to 8 million transduced PBMCs, 4 million transduced PBMCs to 9 million transduced PBMCs, 4 million transduced PBMCs to 10 million transduced PBMCs, 4 million transduced PBMCs to 50 million transduced PBMCs, 4 million transduced PBMCs to 100 million transduced PBMCs, 5 million transduced PBMCs to 6 million transduced PBMCs, 5 million transduced PBMCs to 7 million transduced PBMCs, 5 million transduced PBMCs to 8 million transduced PBMCs, 5 million transduced PBMCs to 9 million transduced PBMCs, 5 million transduced PBMCs to 10 million transduced PBMCs, 5 million transduced PBMCs to 50 million transduced PBMCs, 5 million transduced PBMCs to 100 million transduced PBMCs, 6 million transduced PBMCs to 7 million transduced PBMCs, 6 million transduced PBMCs to 8 million transduced PBMCs, 6 million transduced PBMCs to 9 million transduced PBMCs, 6 million transduced PBMCs to 10 million transduced PBMCs, 6 million transduced PBMCs to 50 million transduced PBMCs, 6 million transduced PBMCs to 100 million transduced PBMCs, 7 million transduced PBMCs to 8 million transduced PBMCs, 7 million transduced PBMCs to 9 million transduced PBMCs, 7 million transduced PBMCs to 10 million transduced PBMCs, 7 million transduced PBMCs to 50 million transduced PBMCs, 7 million transduced PBMCs to 100 million transduced PBMCs, 8 million transduced PBMCs to 9 million transduced PBMCs, 8 million transduced PBMCs to 10 million transduced PBMCs, 8 million transduced PBMCs to 50 million transduced PBMCs, 8 million transduced PBMCs to 100 million transduced PBMCs, 9 million transduced PBMCs to 10 million transduced PBMCs, 9 million transduced PBMCs to 50 million transduced PBMCs, 9 million transduced PBMCs to 100 million transduced PBMCs, 10 million transduced PBMCs to 50 million transduced PBMCs, 10 million transduced PBMCs to 100 million transduced PBMCs, or 50 million transduced PBMCs to 100 million transduced PBMCs. In certain embodiments, a single dosage comprises 1 million transduced PBMCs, 2 million transduced PBMCs, 3 million transduced PBMCs, 4 million transduced PBMCs, 5 million transduced PBMCs, 6 million transduced PBMCs, 7 million transduced PBMCs, 8 million transduced PBMCs, 9 million transduced PBMCs, 10 million transduced PBMCs, 50 million transduced PBMCs, or 100 million transduced PBMCs. In certain embodiments, a single dosage comprises at least 1 million transduced PBMCs, 2 million transduced PBMCs, 3 million transduced PBMCs, 4 million transduced PBMCs, 5 million transduced PBMCs, 6 million transduced PBMCs, 7 million transduced PBMCs, 8 million transduced PBMCs, 9 million transduced PBMCs, 10 million transduced PBMCs, or 50 million transduced PBMCs. In certain embodiments, a single dosage comprises at most 2 million transduced PBMCs, 3 million transduced PBMCs, 4 million transduced PBMCs, 5 million transduced PBMCs, 6 million transduced PBMCs, 7 million transduced PBMCs, 8 million transduced PBMCs, 9 million transduced PBMCs, 10 million transduced PBMCs, 50 million transduced PBMCs, or 100 million transduced PBMCs.

More or less cells may be used depending on the transduction efficiency of an individual's T cells on a case by case basis. In certain embodiments, a single dosage comprises 1 million CAR-T cells to 100 million CAR-T cells. In certain embodiments, a single dosage comprises 1 million CAR-T cells to 2 million CAR-T cells, 1 million CAR-T cells to 3 million CAR-T cells, 1 million CAR-T cells to 4 million CAR-T cells, 1 million CAR-T cells to 5 million CAR-T cells, 1 million CAR-T cells to 6 million CAR-T cells, 1 million CAR-T cells to 7 million CAR-T cells, 1 million CAR-T cells to 8 million CAR-T cells, 1 million CAR-T cells to 9 million CAR-T cells, 1 million CAR-T cells to 10 million CAR-T cells, 1 million CAR-T cells to 50 million CAR-T cells, 1 million CAR-T cells to 100 million CAR-T cells, 2 million CAR-T cells to 3 million CAR-T cells, 2 million CAR-T cells to 4 million CAR-T cells, 2 million CAR-T cells to 5 million CAR-T cells, 2 million CAR-T cells to 6 million CAR-T cells, 2 million CAR-T cells to 7 million CAR-T cells, 2 million CAR-T cells to 8 million CAR-T cells, 2 million CAR-T cells to 9 million CAR-T cells, 2 million CAR-T cells to 10 million CAR-T cells, 2 million CAR-T cells to 50 million CAR-T cells, 2 million CAR-T cells to 100 million CAR-T cells, 3 million CAR-T cells to 4 million CAR-T cells, 3 million CAR-T cells to 5 million CAR-T cells, 3 million CAR-T cells to 6 million CAR-T cells, 3 million CAR-T cells to 7 million CAR-T cells, 3 million CAR-T cells to 8 million CAR-T cells, 3 million CAR-T cells to 9 million CAR-T cells, 3 million CAR-T cells to 10 million CAR-T cells, 3 million CAR-T cells to 50 million CAR-T cells, 3 million CAR-T cells to 100 million CAR-T cells, 4 million CAR-T cells to 5 million CAR-T cells, 4 million CAR-T cells to 6 million CAR-T cells, 4 million CAR-T cells to 7 million CAR-T cells, 4 million CAR-T cells to 8 million CAR-T cells, 4 million CAR-T cells to 9 million CAR-T cells, 4 million CAR-T cells to 10 million CAR-T cells, 4 million CAR-T cells to 50 million CAR-T cells, 4 million CAR-T cells to 100 million CAR-T cells, 5 million CAR-T cells to 6 million CAR-T cells, 5 million CAR-T cells to 7 million CAR-T cells, 5 million CAR-T cells to 8 million CAR-T cells, 5 million CAR-T cells to 9 million CAR-T cells, 5 million CAR-T cells to 10 million CAR-T cells, 5 million CAR-T cells to 50 million CAR-T cells, 5 million CAR-T cells to 100 million CAR-T cells, 6 million CAR-T cells to 7 million CAR-T cells, 6 million CAR-T cells to 8 million CAR-T cells, 6 million CAR-T cells to 9 million CAR-T cells, 6 million CAR-T cells to 10 million CAR-T cells, 6 million CAR-T cells to 50 million CAR-T cells, 6 million CAR-T cells to 100 million CAR-T cells, 7 million CAR-T cells to 8 million CAR-T cells, 7 million CAR-T cells to 9 million CAR-T cells, 7 million CAR-T cells to 10 million CAR-T cells, 7 million CAR-T cells to 50 million CAR-T cells, 7 million CAR-T cells to 100 million CAR-T cells, 8 million CAR-T cells to 9 million CAR-T cells, 8 million CAR-T cells to 10 million CAR-T cells, 8 million CAR-T cells to 50 million CAR-T cells, 8 million CAR-T cells to 100 million CAR-T cells, 9 million CAR-T cells to 10 million CAR-T cells, 9 million CAR-T cells to 50 million CAR-T cells, 9 million CAR-T cells to 100 million CAR-T cells, 10 million CAR-T cells to 50 million CAR-T cells, 10 million CAR-T cells to 100 million CAR-T cells, or 50 million CAR-T cells to 100 million CAR-T cells. In certain embodiments, a single dosage comprises 1 million CAR-T cells, 2 million CAR-T cells, 3 million CAR-T cells, 4 million CAR-T cells, 5 million CAR-T cells, 6 million CAR-T cells, 7 million CAR-T cells, 8 million CAR-T cells, 9 million CAR-T cells, 10 million CAR-T cells, 50 million CAR-T cells, or 100 million CAR-T cells. In certain embodiments, a single dosage comprises at least 1 million CAR-T cells, 2 million CAR-T cells, 3 million CAR-T cells, 4 million CAR-T cells, 5 million CAR-T cells, 6 million CAR-T cells, 7 million CAR-T cells, 8 million CAR-T cells, 9 million CAR-T cells, 10 million CAR-T cells, or 50 million CAR-T cells. In certain embodiments, a single dosage comprises at most 2 million CAR-T cells, 3 million CAR-T cells, 4 million CAR-T cells, 5 million CAR-T cells, 6 million CAR-T cells, 7 million CAR-T cells, 8 million CAR-T cells, 9 million CAR-T cells, 10 million CAR-T cells, 50 million CAR-T cells, or 100 million CAR-T cells.

In certain embodiments, a population of the anti-ROR-1 CAR-T cells of the current disclosure are included in a pharmaceutical composition comprising one or more pharmaceutically acceptable excipients, carriers, and diluents. In certain embodiments, the CAR-T cells of the current disclosure are administered suspended in a sterile isotonic solution. In certain embodiments, the solution comprises about 0.9% NaCl. In certain embodiments, the solution comprises about 5.0% dextrose. In certain embodiments, the solution further comprises one or more of: buffers, for example, acetate, citrate, histidine, succinate, phosphate, bicarbonate and hydroxymethylaminomethane (Tris); surfactants, for example, polysorbate 80 (Tween 80), polysorbate 20 (Tween 20), and poloxamer 188; polyol/disaccharide/polysaccharides, for example, glucose, dextrose, mannose, mannitol, sorbitol, sucrose, trehalose, and dextran 40; amino acids, for example, glycine or arginine; antioxidants, for example, ascorbic acid, methionine; or chelating agents, for example, EDTA or EGTA. The CAR-T cells when formulated, can be buffered at a certain pH, generally between about 7.0 and about 8.0. In certain embodiments, the cells are buffered at a physiological pH of about 7.4 (averaging between about 7.35 and 7.45.

Also described herein are methods of treating an individual that has developed one or more serious adverse events associated with CAR T-cell treatment comprising administering a bolus injection of cirmtuzumab. Such an administration blocks CAR T-cells from interacting with their targets and can attenuate their activity.

Also described herein are kits comprising one or more of the nucleic acids encoding the CAR-t cells described herein in a suitable container and one or more additional components selected from: instructions for use; a diluent, an excipient, a carrier, and a device for administration.

In certain embodiments, described herein is a method of preparing a cancer treatment comprising admixing one or more pharmaceutically acceptable excipients, carriers, or diluents and an antibody of the current disclosure. In certain embodiments, described herein is a method of preparing a cancer treatment for storage or shipping comprising lyophilizing one or more antibodies of the current disclosure.

EXAMPLES

The following illustrative examples are representative of embodiments of compositions and methods described herein and are not meant to be limiting in any way.

Example 1: Chimeric Antigen Receptor Modified T-Cells (Car-T) that Target ROR-1

A series of monoclonal antibodies have previously been described that target the ROR-1 antigen, this target is the subject of ongoing clinical trials in patients with CLL, MCL and breast cancer employing the anti-human ROR-1 mAb UC-961 (cirmtuzumab) combined with standard chemotherapies. The CARs constructed and tested in these examples utilize the complementarity determining regions (CDRs) and variable regions (VH/VL) of the cirmtuzumab antibody. The cirmtuzumab antibody and sequences encoding it's CDRS and VH/VL are disclosed in WO 2014/031174.

There are several unmet needs in the CAR-T space for treatment of cancer. The CAR T cells described herein solve these unmet needs.

Treatment Failures

There is an increasing number of patient relapses following CAR-T therapy, frequently due to mutations or loss of target tumor antigen (e.g., CD19), evading CAR-T cells. Using ROR-1 as a target potentially provides for fewer antigen negative relapses, as ROR-1 expression is associated with aggressive tumor phenotype, and ROR-1 mutation or antigen loss might render cancer cells less aggressive and susceptible to chemotherapy.

Safety Concerns

Persistent CAR-T safety issues include deaths potentially related to activation by normal cells expressing the target antigen ("on-target/off-tumor"). Previous studies have shown Cirmtuzumab did not bind to normal human tissues in GLP tissue cross-reactivity studies, and there are no serious adverse events related to cirmtuzumab-only reported in clinical studies.

Figure 1B:
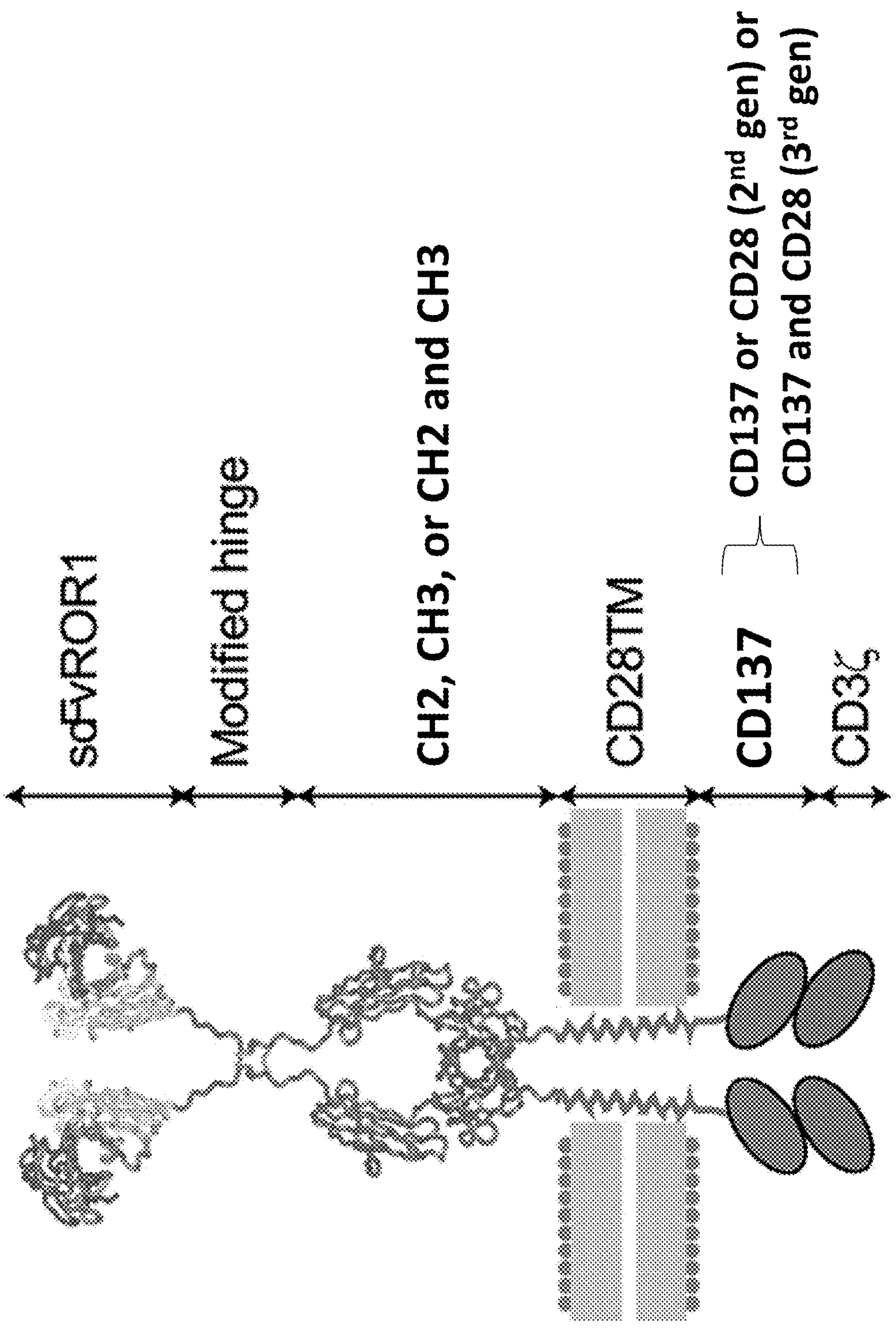
FIG. 1B illustrates alternative embodiments of CARs according to this disclosure.

An additional avenue of therapeutic intervention is to employ the antigen binding domains of these anti-human ROR-1 antibodies, including UC-961, as the targeting moieties of a CAR. FIG. 1A shows an artist's rendering of an anti-ROR-1 CAR-T cell interacting with an ROR-1 expressing cancer cell (CLL). FIG. 1B shows a schematic of different non-limiting embodiments of CARs of this disclosure. The CARs of this disclosure describe light chain CDRs of the anti-human ROR-1 mAbs 4A5 or UC-961 attached to the heavy chain CDRs of the same mAbs by specific linkers that generate high-affinity single-chain (scFv) molecules that specifically bind human ROR-1 with a sufficient affinity to activate intracellular signaling and cytotoxicity in the transduced T-lymphocytes. To attach the scFv to a transmembrane domain, a series of protein spacers generated from IgG4 have been created. These spacers allow the anti-ROR-1 scFv binding domain sufficient flexibility to optimally bind the target ROR-1 antigen.

Figure 1C:
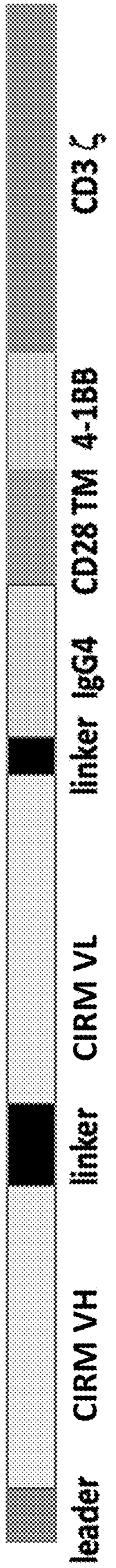
FIG. 1C illustrates a $2^{nd}$ generation CAR introduced into healthy human donor T lymphocytes by a $2^{nd}$ generation lentiviral vector. The activity of this highly active and specific CAR product is shown in FIG. 8A and FIG. 9A.
Figure 2A:
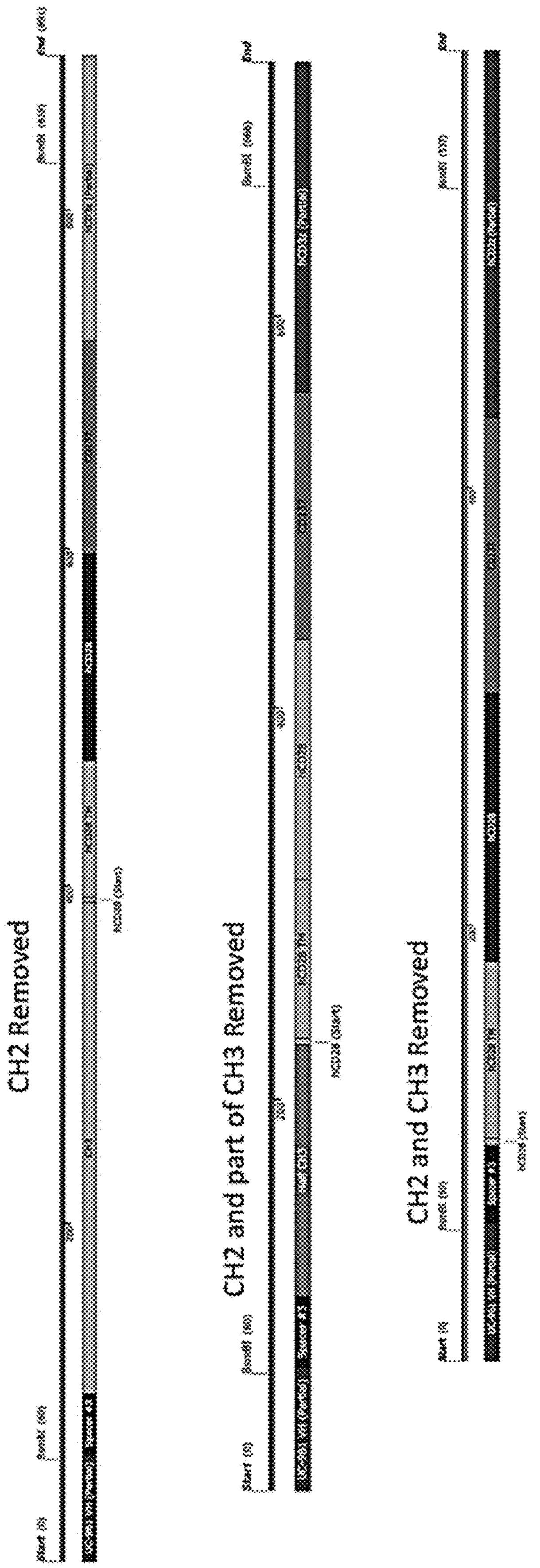
FIG. 2A and FIG. 2B illustrate vector schematics for a coding region of a CAR of this disclosure.
Figure 2B:
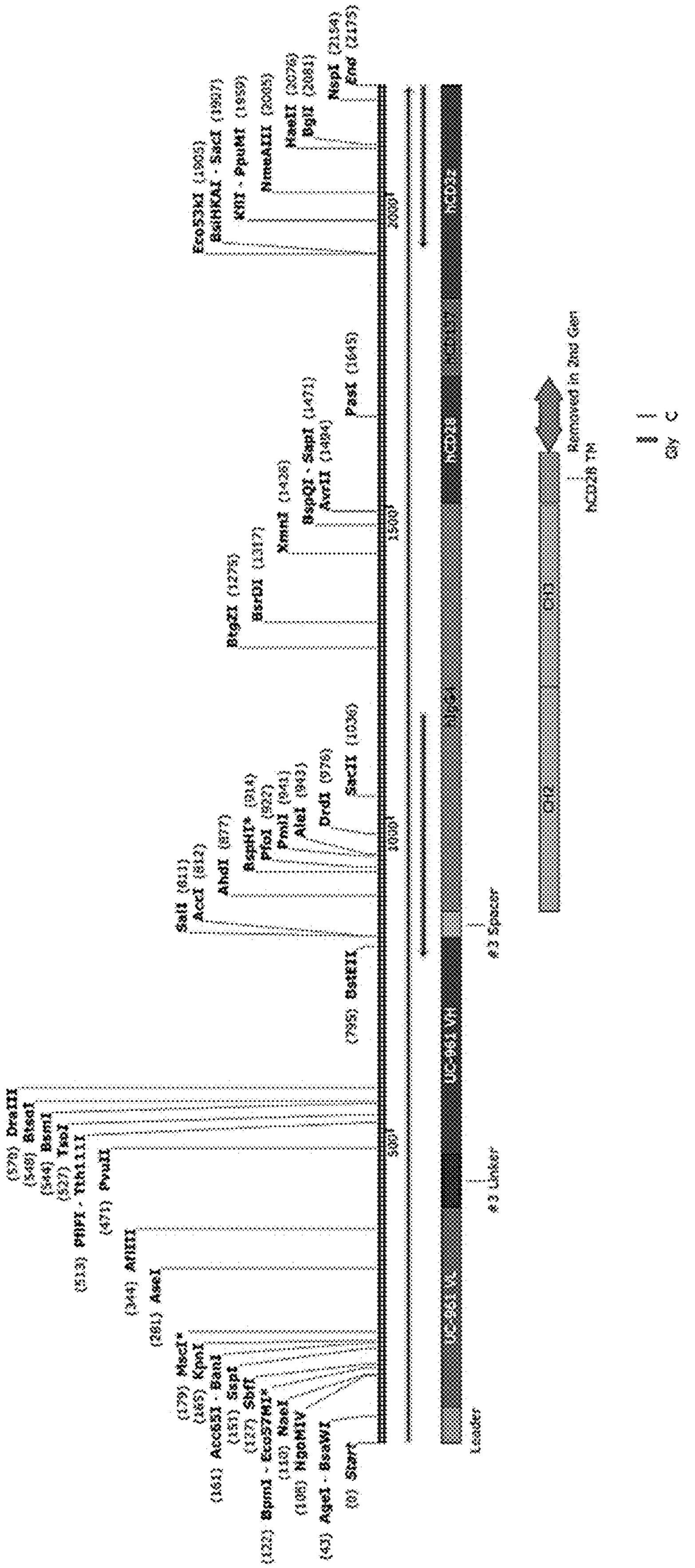

Still referring to FIG. 1B, the extracellular antigen binding domain from the CARs is bound to a CD28 transmembrane domain. This transmembrane domain is then attached to an intracellular activating domain derived from CD28 and/or CD137, which are employed singularly ($2^{nd}$_gen CAR) or in combination ($3^{rd}$ gen CAR). These activating domains are then attached to the T-cell receptor activating domain contained within the CD3 zeta chain (CD3 ζ-chain). Therefore, the anti-ROR-1 CARs (shown in FIG. 1A, 1B, 1C) are expressed as a single polypeptide that from the N-terminal end contains in order: a leader that directs the construct to the cell surface, the light chain CDR of either the 4A5 or UC-961 mAbs, a linker that attaches the light and heavy chains, the heavy chain CDR of 4A5 or UC-961 mAbs that are complimented by the corresponding light chain molecules, a spacer of defined length generated from IgG4 including the IgG4 hinge region, the CD28 transmembrane region, the intracellular activation domains of CD28 and 41-BB (CD137)-individually or in tandem attached to the T-cell ζ-chain which extends to the carboxy terminus of the molecule. FIGS. 2A and 2B show vector schematics illustrating CARS with different spacer domains.

Figure 3:
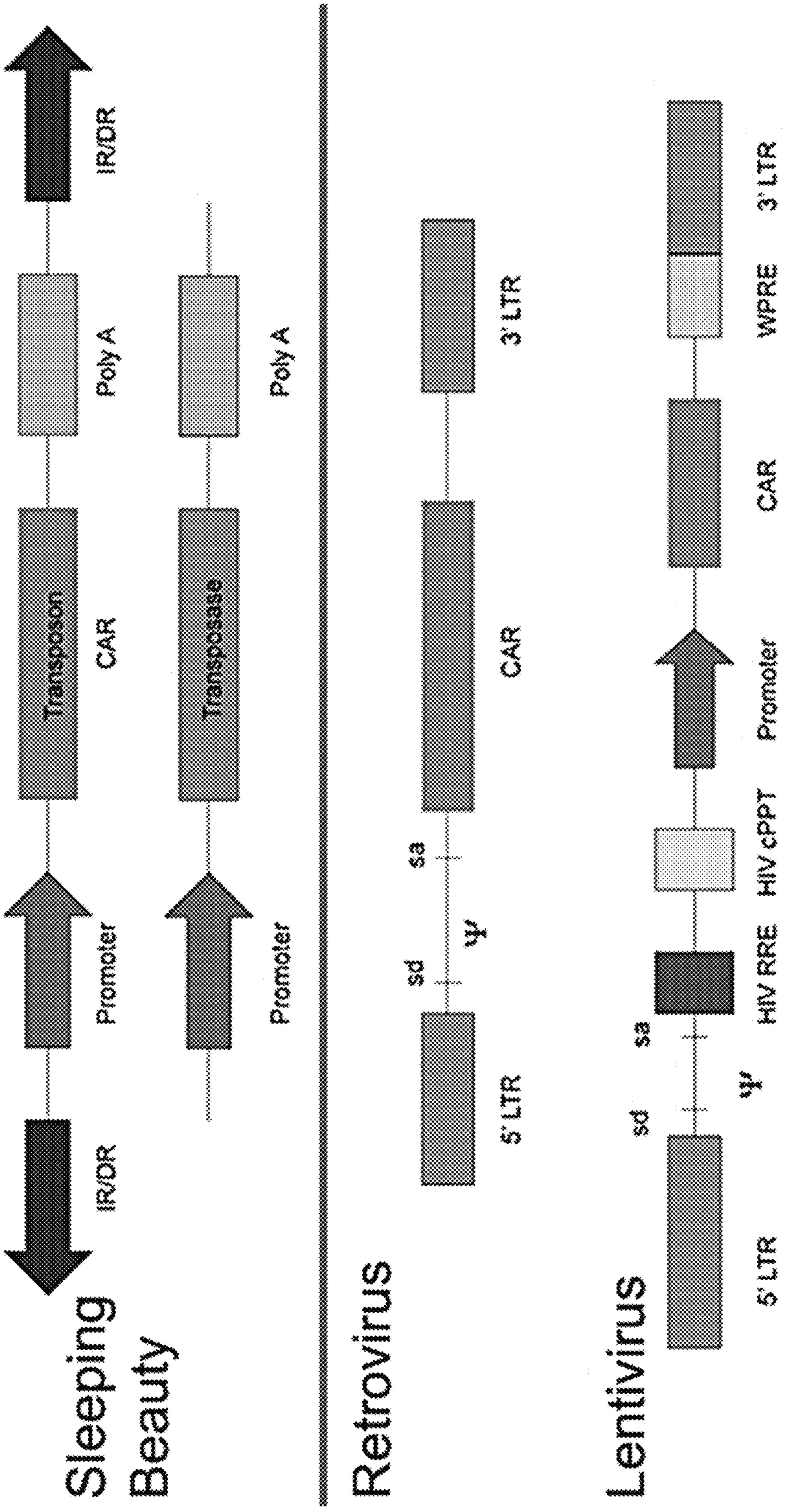
FIG. 3 illustrates schematics for lentiviral and transposon-based gene delivery vectors that can be used to transduce immune cells with the CARs of this disclosure.

The CARs described herein can be included in a transposon based or lentiviral vector, as shown in FIG. 3 and introduced into target lymphocytes employing standard transfection or transduction techniques. To maximize stable transduction and long-term expression of the CAR product, retroviral delivery systems are used including murine gamma and human lentivirus. Currently, a third generation lentiviral, four plasmid system (Addgene, Inc.) is used to render T lymphocytes transgenic for an ROR-1 expressing CAR. This third-generation system is based on the lentiviral vector system described in Naldini et al, "Efficient transfer, integration, and sustained long-term expression of the transgene in adult rat brains injected with a lentiviral vector" *Proc Natl Acad Sci USA.* 1996 Oct. 15; 93 (21): 11382-11388. This four-plasmid system comprises: plasmid 1-gag/pol; plasmid 2-rev; plasmid 3 VSV-G protein; and plasmid 4, the transfer plasmid, which comprises a nucleic acid sequence encoding an anti-ROR1 CAR, which has been inserted using the restriction sites in the poly-linker.

Figure 4A:
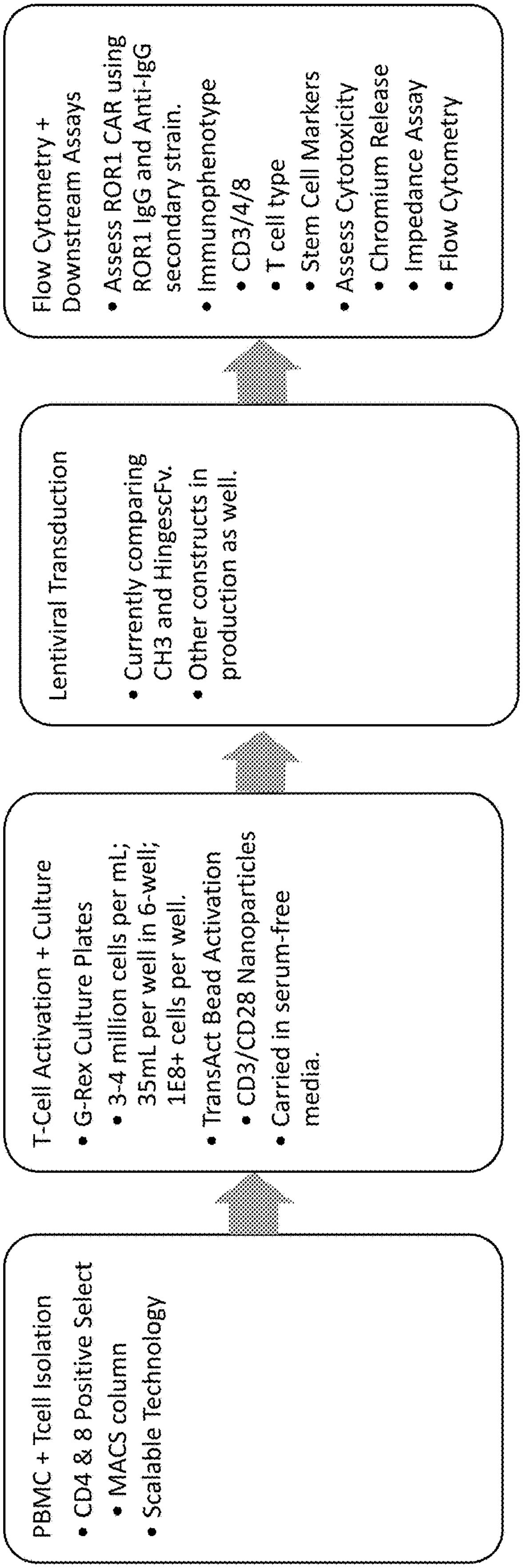
FIG. 4A and FIG. 4B illustrate two different methods of transducing immune cells with the CARs.
Figure 4B:
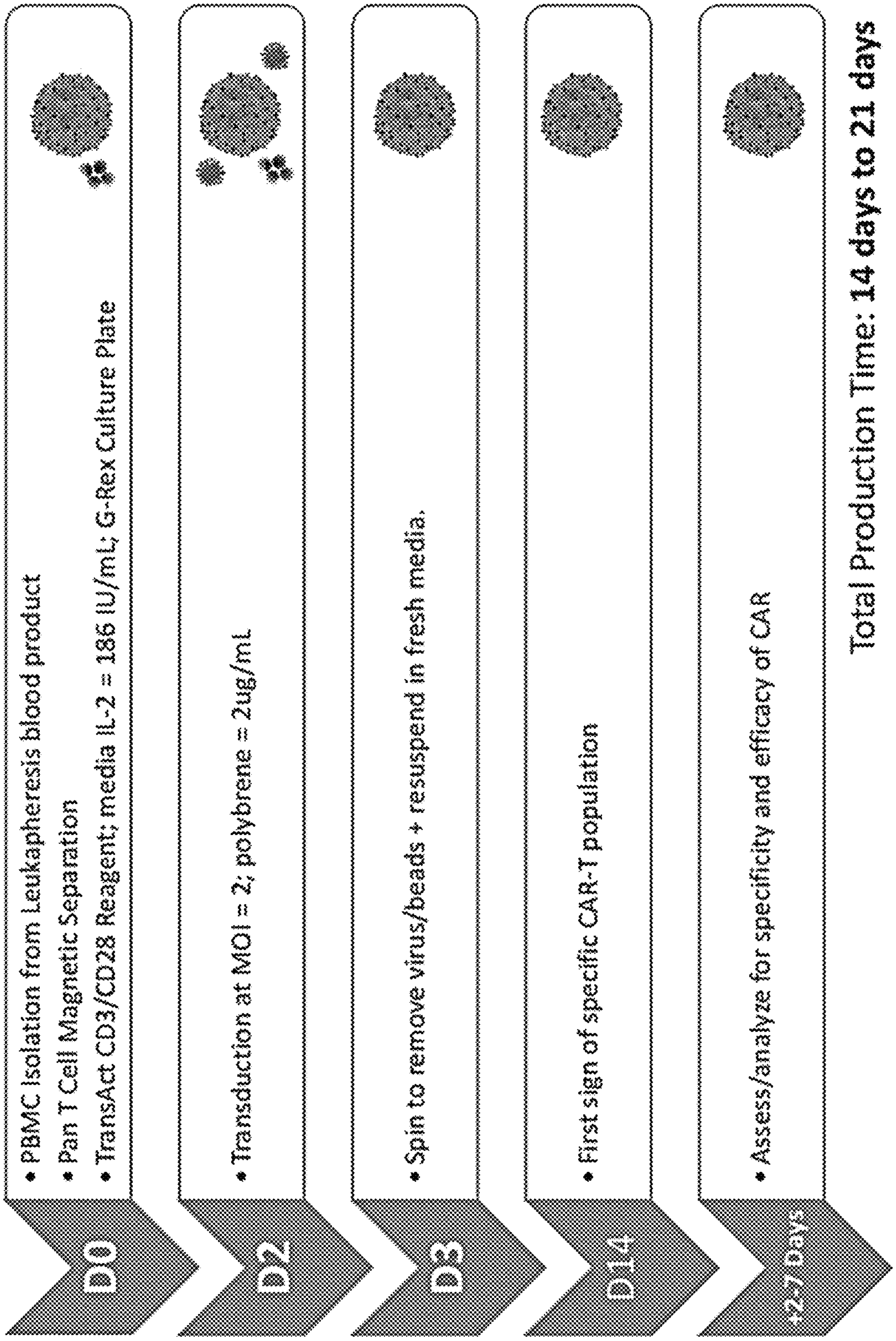

FIGS. 4A and 4B illustrate steps of making an anti-ROR-1 CAR expressing T cell. Referring to FIG. 4A, T cells are isolated from peripheral blood mononuclear cells (PBMC), followed by activation with CD3/Cd28 nanoparticles, transduction with lentivirus, and optionally, analysis steps to verify CAR expression and specificity.

Figure 5A:
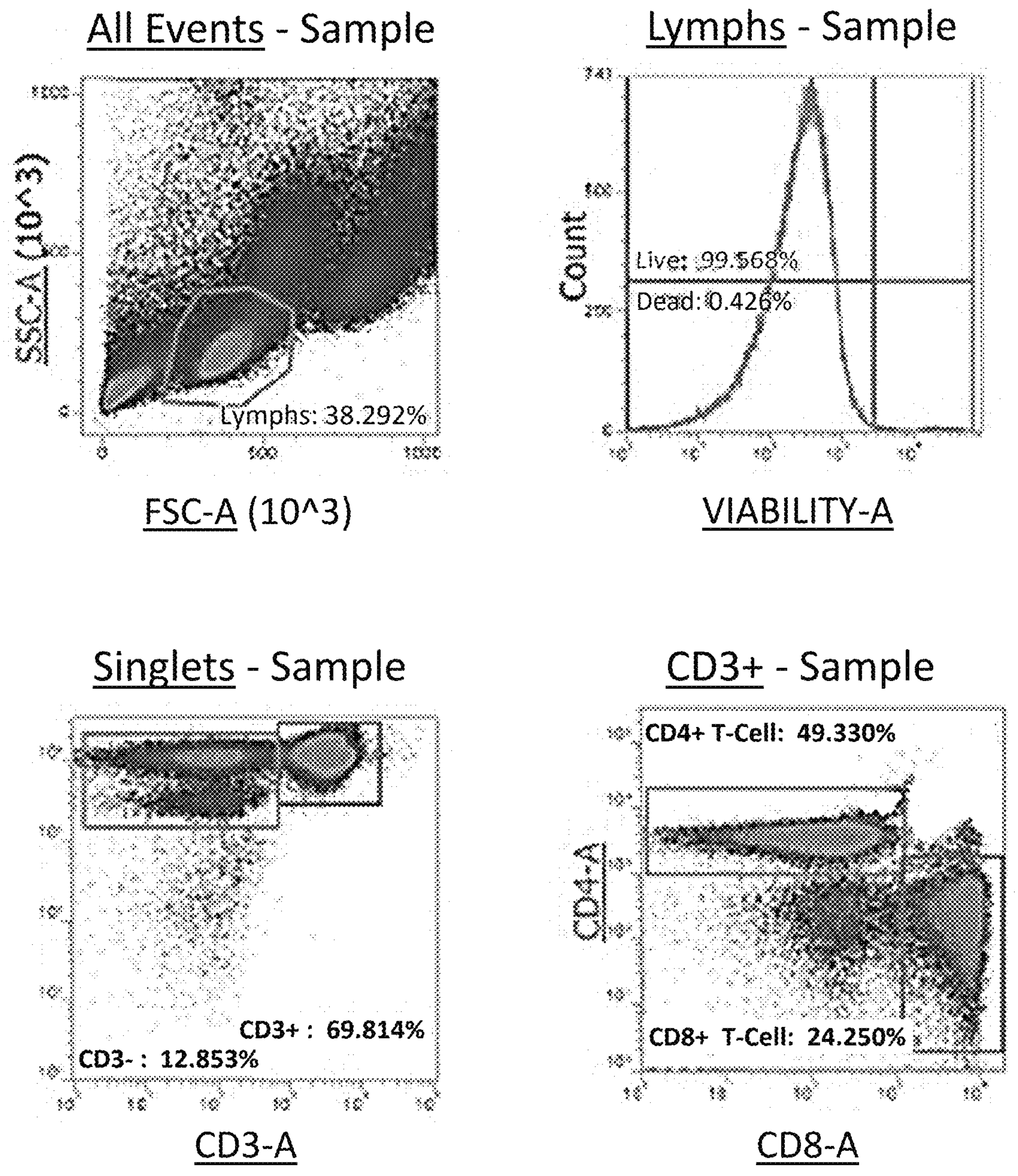
FIG. 5A and FIG. 5B show flow cytometry of total PBMC before (A) and after (B) T cell isolation.
Figure 5B:
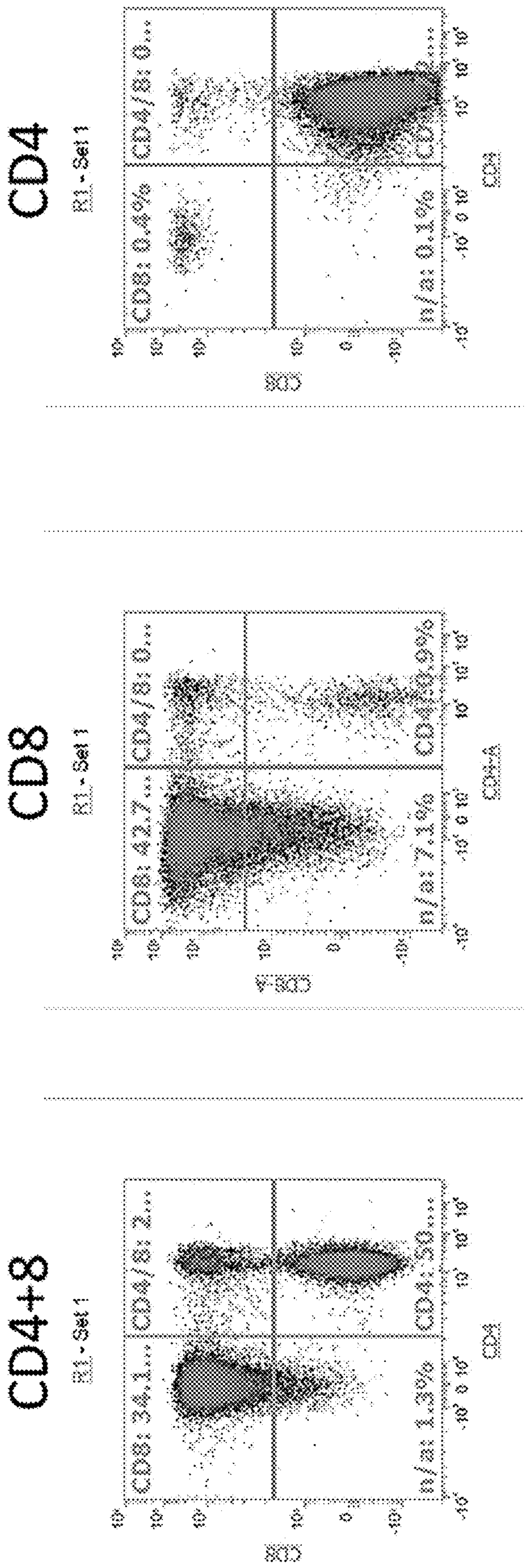
Figure 6A:
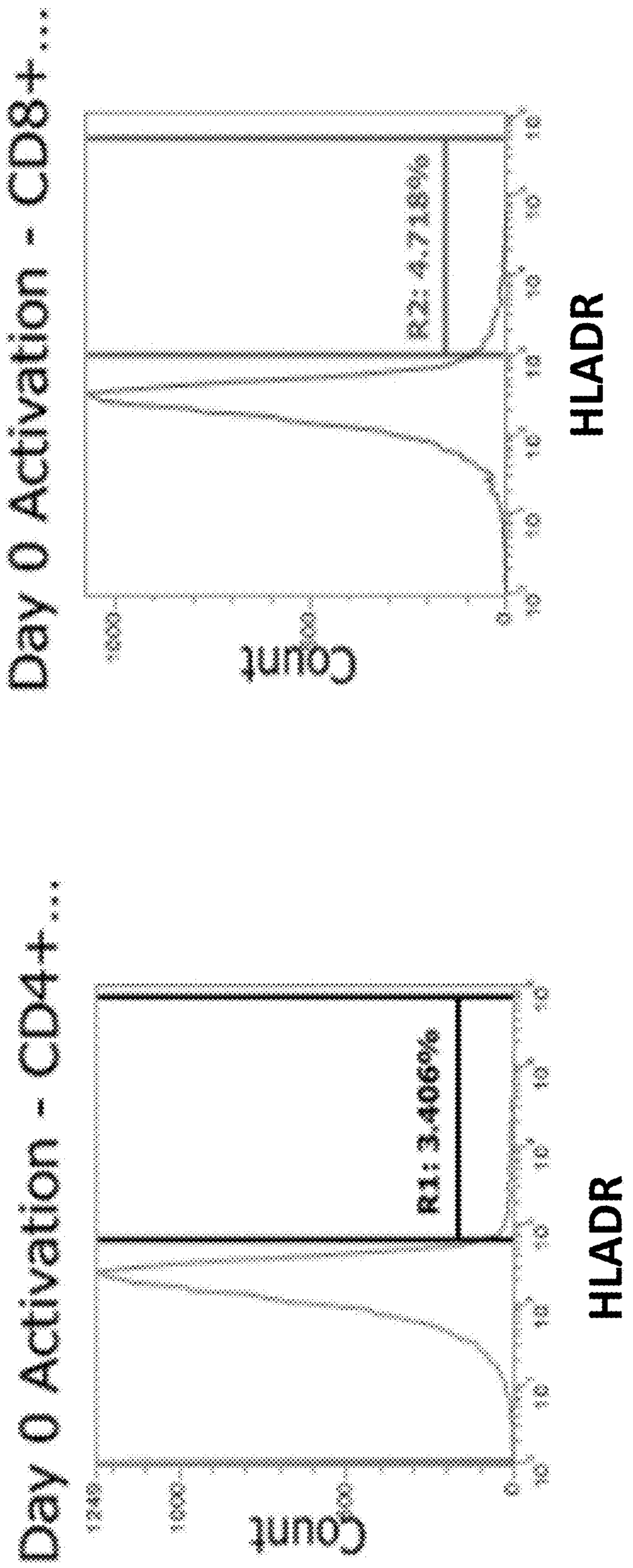
FIG. 6A shows activation profile of different T cell subsets after 3 days.
Figure 6A:
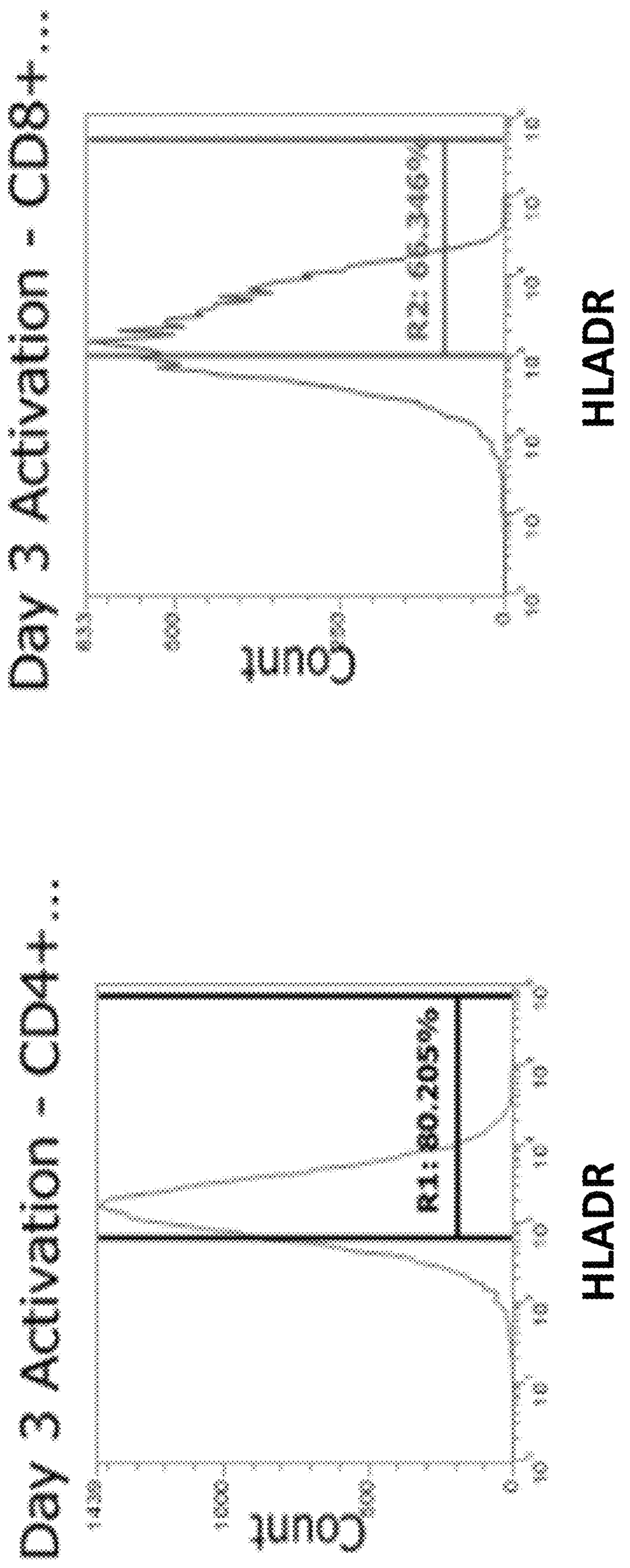
Figure 6B:
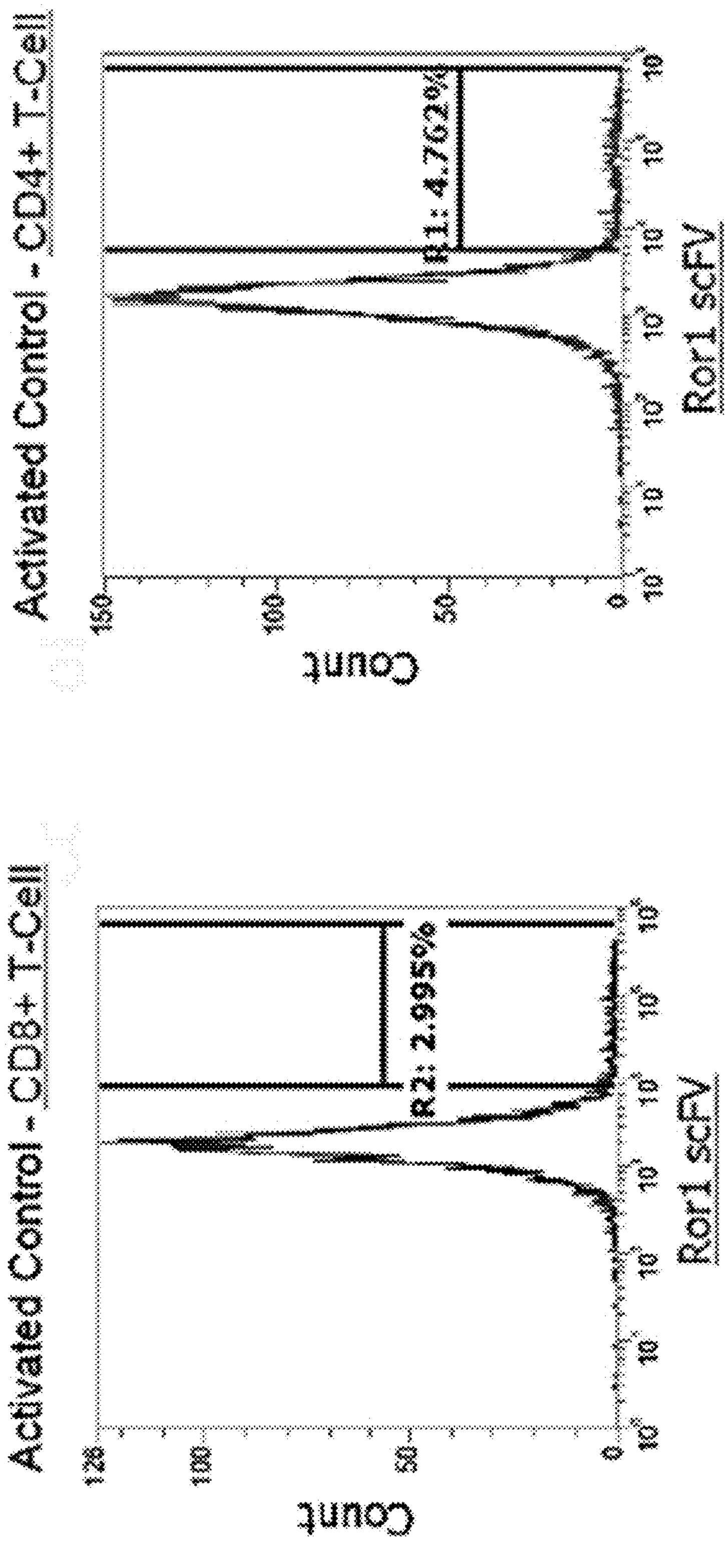
FIG. 6B shows transduction efficiency with lentivirus at an MOI of 1 or 3.
Figure 6B:
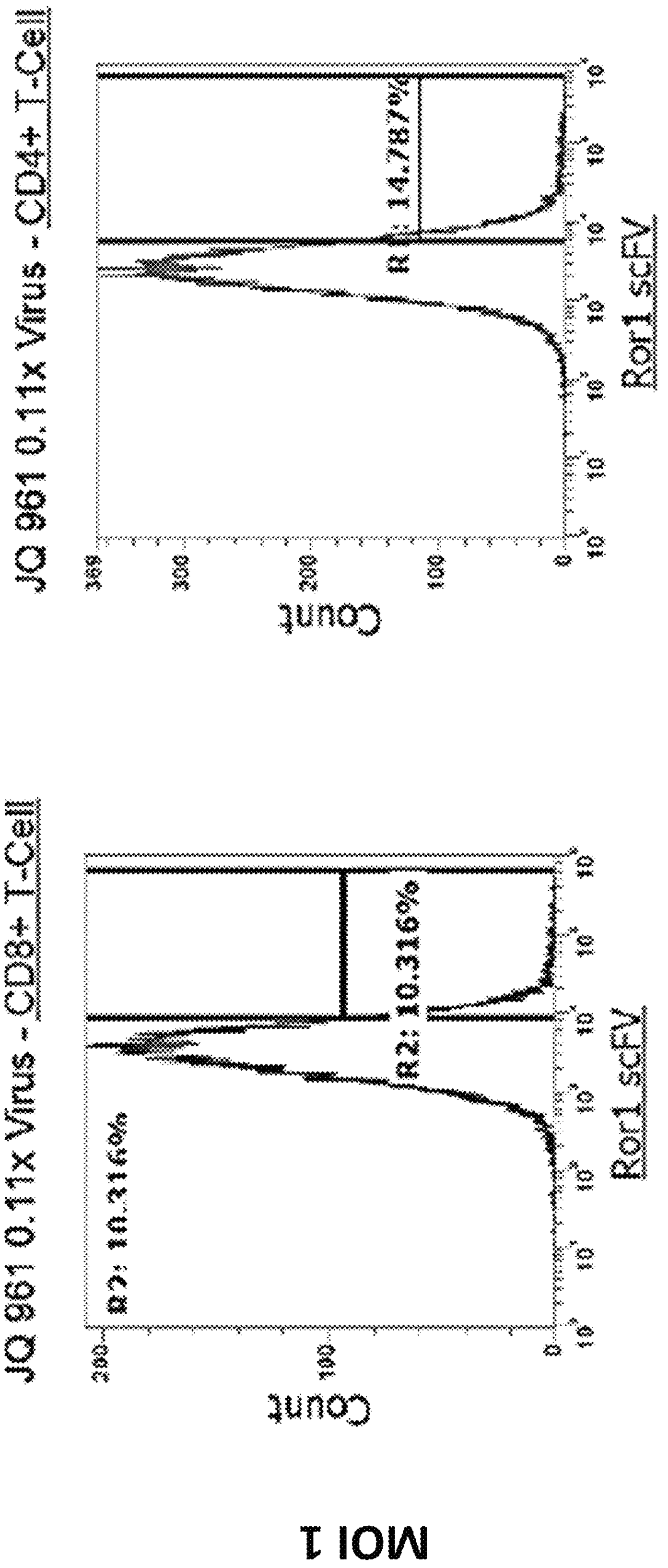
Figure 6B:
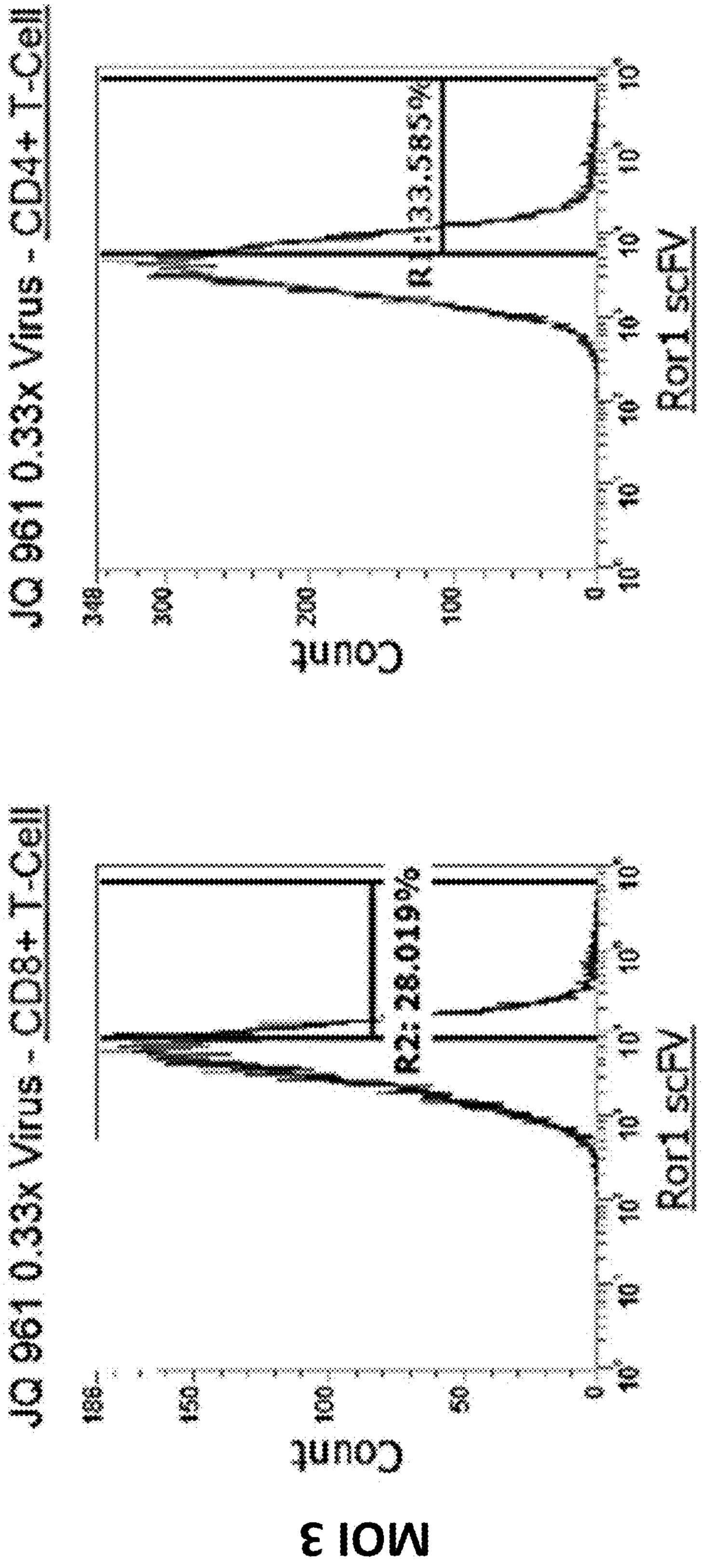
Figure 7A:
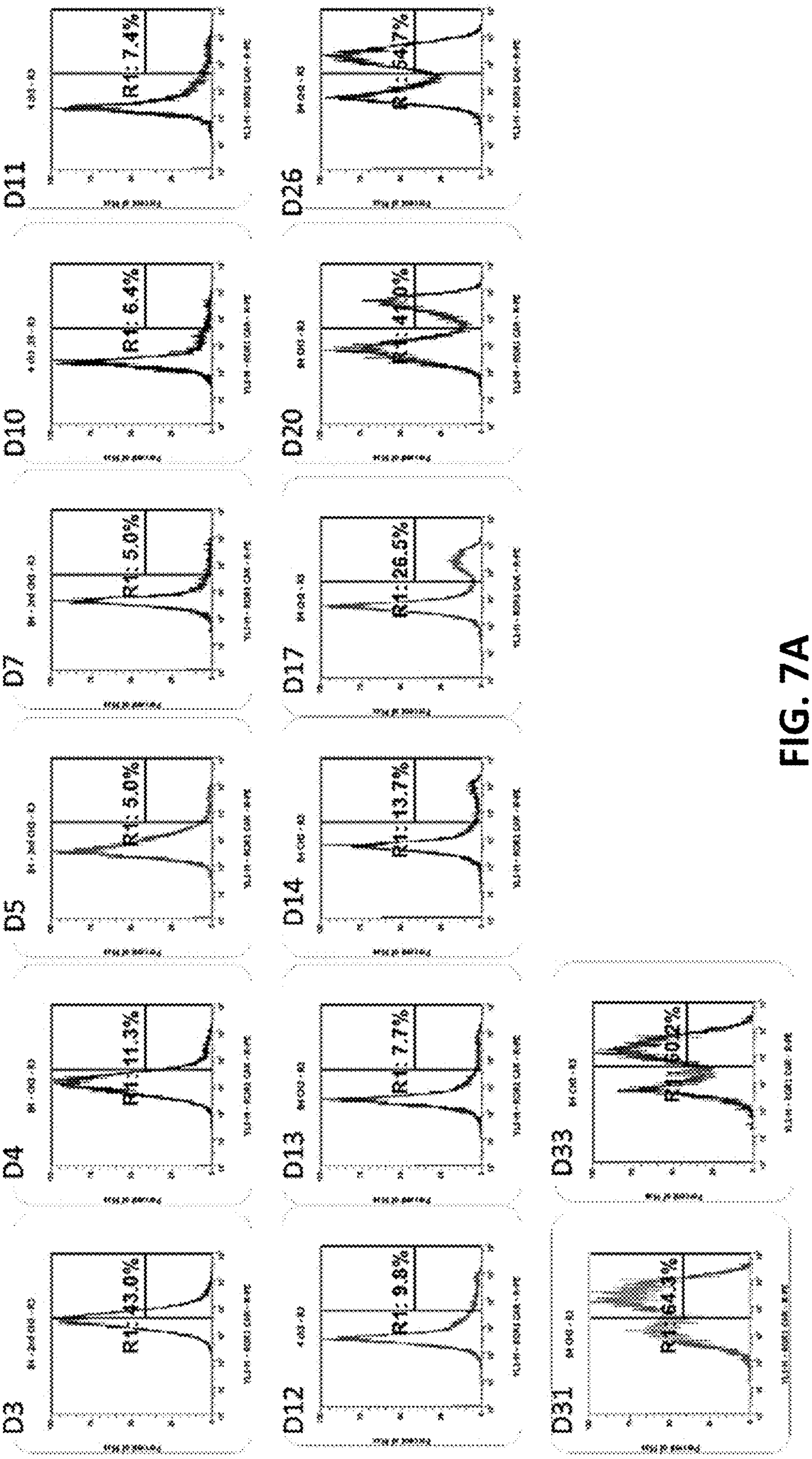
FIG. 7A and FIG. 7B show a time course of CAR cell-surface expression after transduction.
Figure 7B:
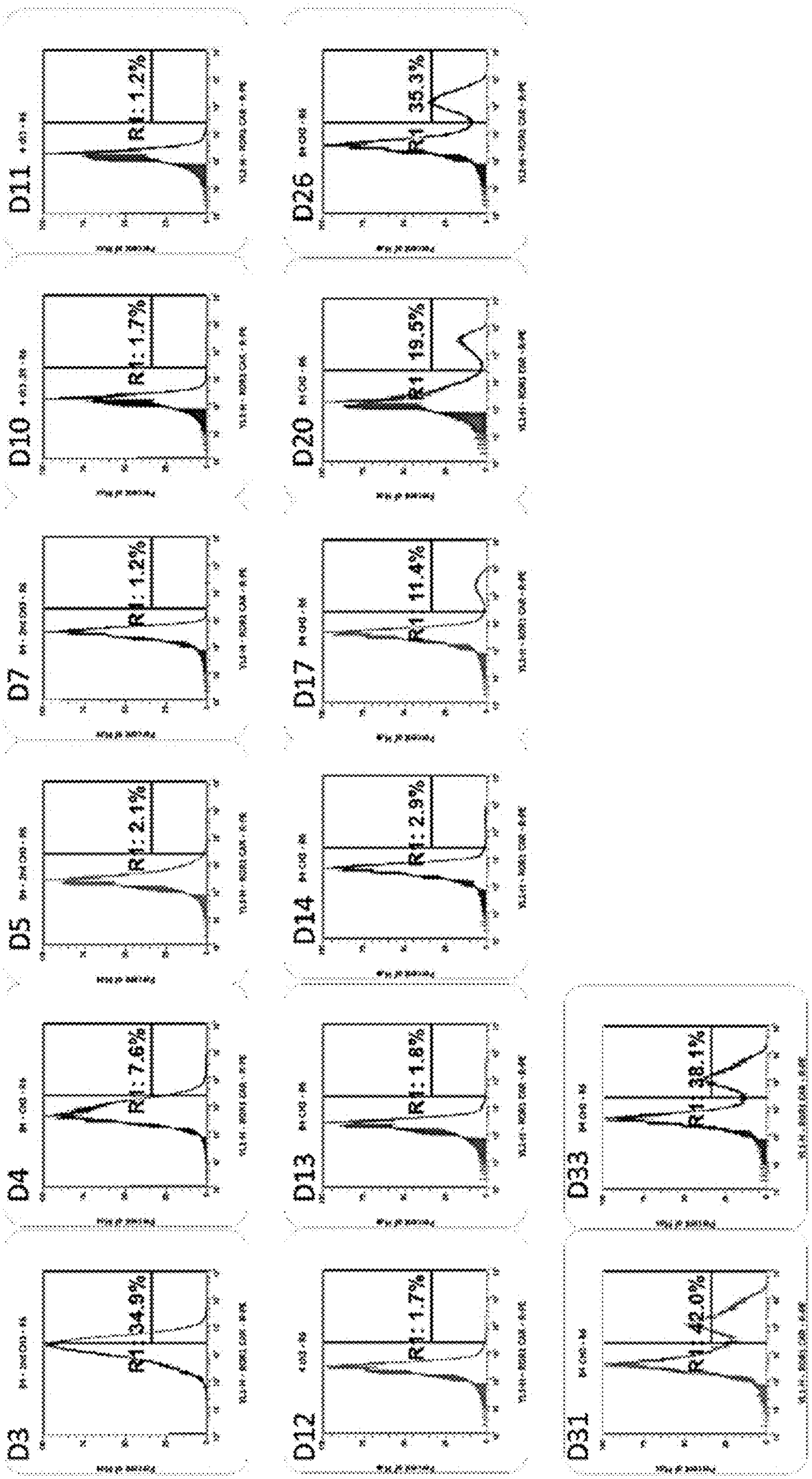

FIG. 5A shows flow cytometry analysis of whole-blood PBMC. FIG. 5B shows CD8+ and CD4+ populations after purification. FIG. 6A shows that activation by CD3/CD28 results in activation of both CD4+ (80%) and CD8+ (63%) cells, and FIG. 6B shows that lentiviral transduction results in dose dependent transduction efficiency of CD8+ T cells of 10% (MOI 1) or 28% (MOI 3); or of CD4+ T cells of 15% (MOI 1) or 34% (MOI 3). FIGS. 7A and 7B show a time course of anti-ROR-1 CAR expression after lentiviral transduction of T lymphocytes.

Example 2: In Vitro Activity of Chimeric Antigen Receptor Modified T-Cells (Car-T) that Target ROR-1

Several chimeric antigen receptors (CARs) that target the cancer associated antigen ROR-1 were created according to the above scheme and used to transduce cytotoxic T lymphocytes.

To generate an anti-human ROR1 T-cell CAR, multiple candidate $2^{nd}$ and $3^{rd}$ generation CAR constructs were generated with different signaling and spacer domains. To test these constructs, the candidate CAR-Ts were produced and expanded in a serum-free growth media supplemented with IL-2. Using this protocol, CAR-T cells from over 20 healthy donors have been generated and their activity has been examined against lymphoid cancers in vitro using chromium release and impedance assays. The $2^{nd}$ generation CARs using the 4-1BB co-stimulation domain had activity even at low effector to target (E:T) ratios, eliminated both primary B-cell leukemias and lymphomas, as well as tumor cell lines that express the ROR1 target.

Figure 8A:
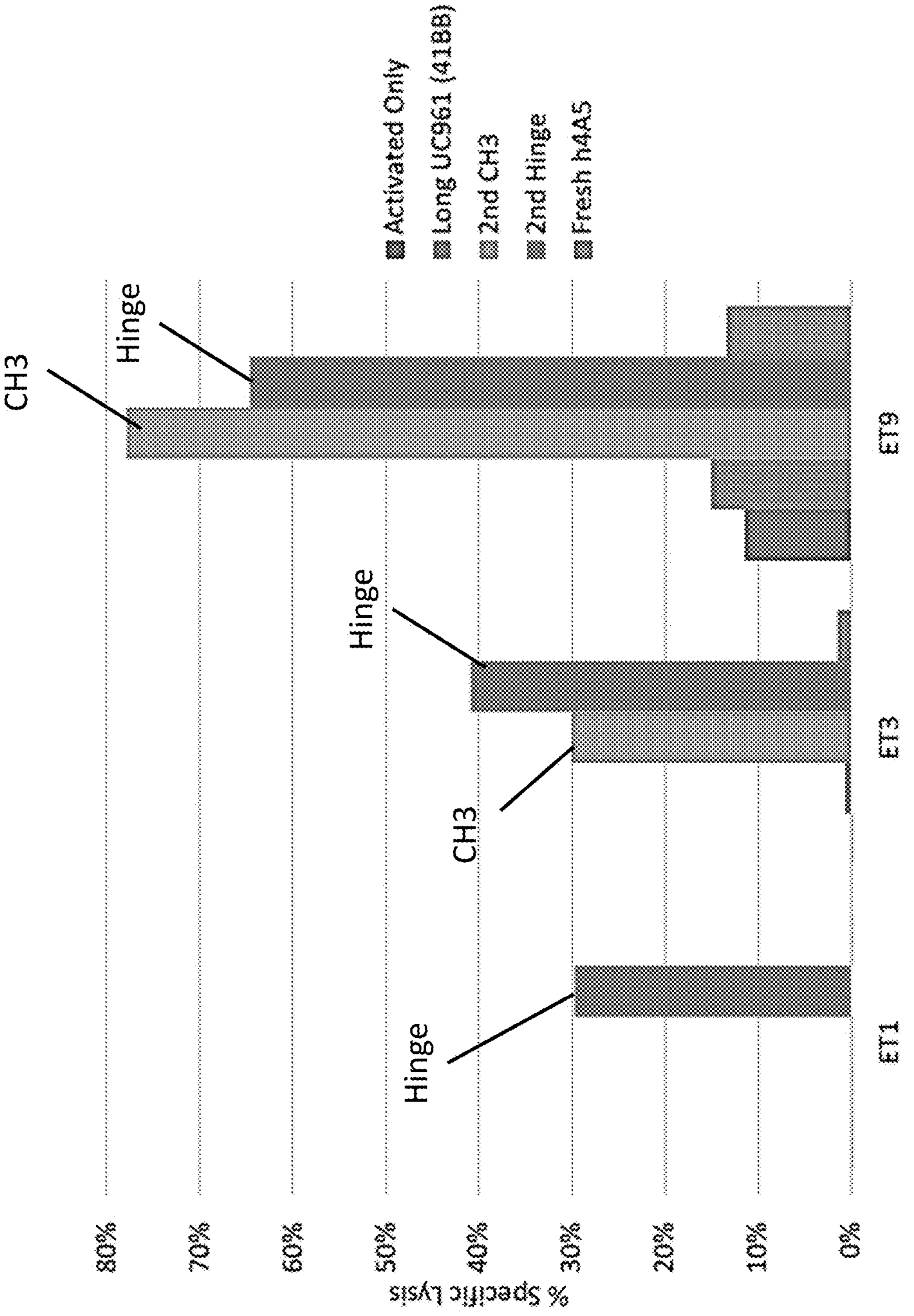
FIG. 8A and FIG. 8B show chromium release assays of $2^{nd}$ generation CARs utilizing different spacers between the scFV and the transmembrane domain of the CAR against MEC-1 cells that express ROR-1 (A), or lack ROR-1 expression (B).
Figure 8B:
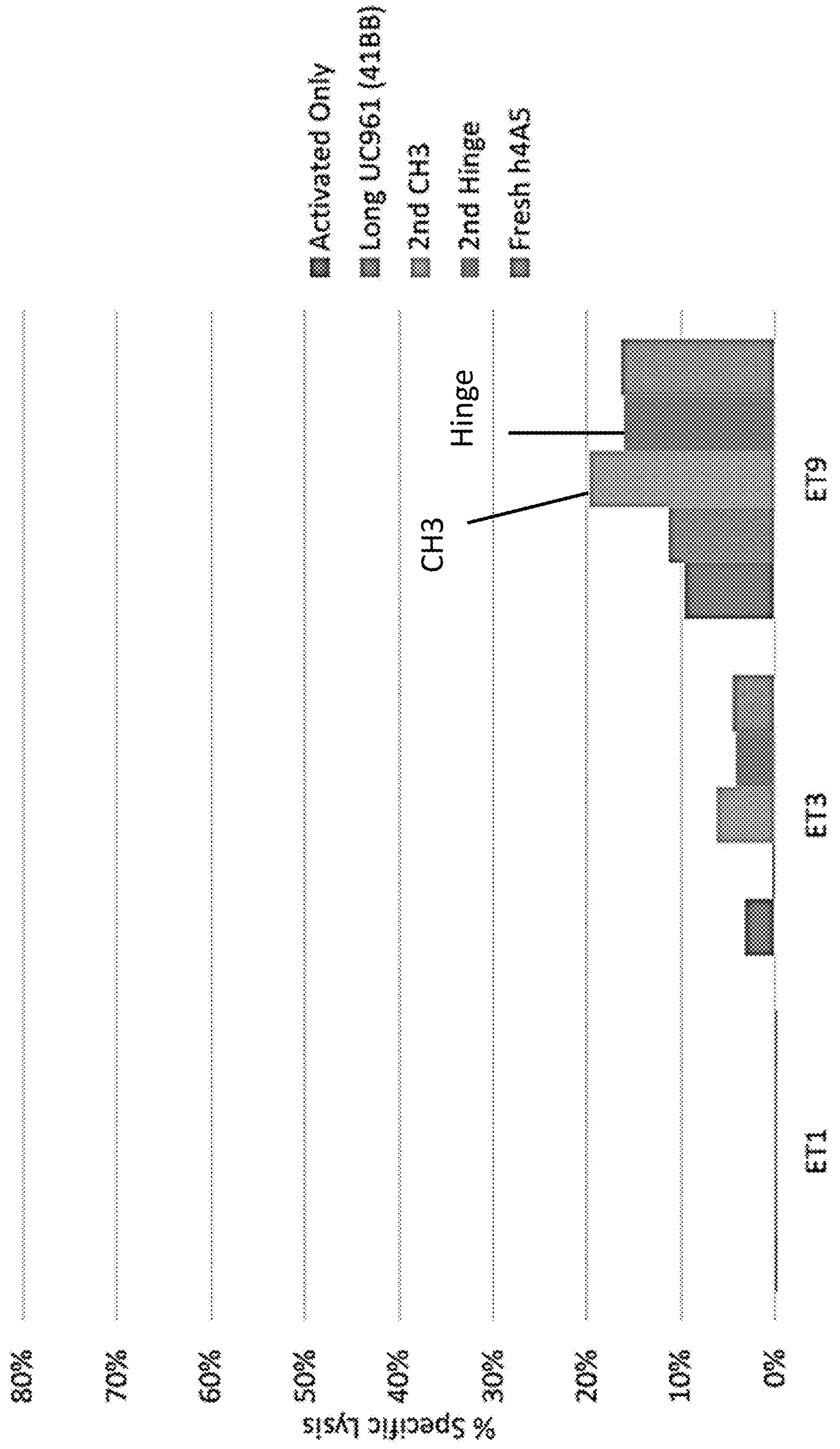

These T cell CARs demonstrated specific activity in targeting ROR-1 expressed on both hematological and solid tumor cancers. As shown in FIG. 8A, T-lymphocytes expressing anti-ROR-1 CAR are effective at killing leukemic MEC-1/ROR1 cells at different effector to target (E:T) ratios. These results were generated through the use of a 4-hour chromium release assay. In this study anti-ROR1 CARs expressing the hinge and CH3 spacers had the greatest activity. For FIG. 8A, "Activated Only" (leftmost bar; ET9) are T-cells isolated from PBMC or blood product which have undergone the identical activation and cell culture process as CAR-T-cells, but without transduction of lentiviral CAR; "Long UC961" (second bar from the left) refers to a construct utilizing the CH2CH3 spacer, comprising Spacer #3 (SEQ ID NO:29) and both the CH2 and CH3 regions of hIgG4; "CH3" (third bar from left) refers to CAR-T construct utilizing spacer CH3, comprising Spacer #3 and the CH3 region of human IgG4; and "Hinge" (fourth bar from the left) refers to a CAR-T construct utilizing Spacer #3 (Hinge) without human IgG4 CH2 and CH3 domains. FIG. 8B shows 4-hour chromium release assay with non-ROR-1 expressing MEC-1 cells. This data indicates that ROR-1 CARs are specific and kill only based on the presence of ROR-1 at the cell surface of a target cell. Bars in FIG. 8B are ordered as in FIG. 8A.

Figure 8C:
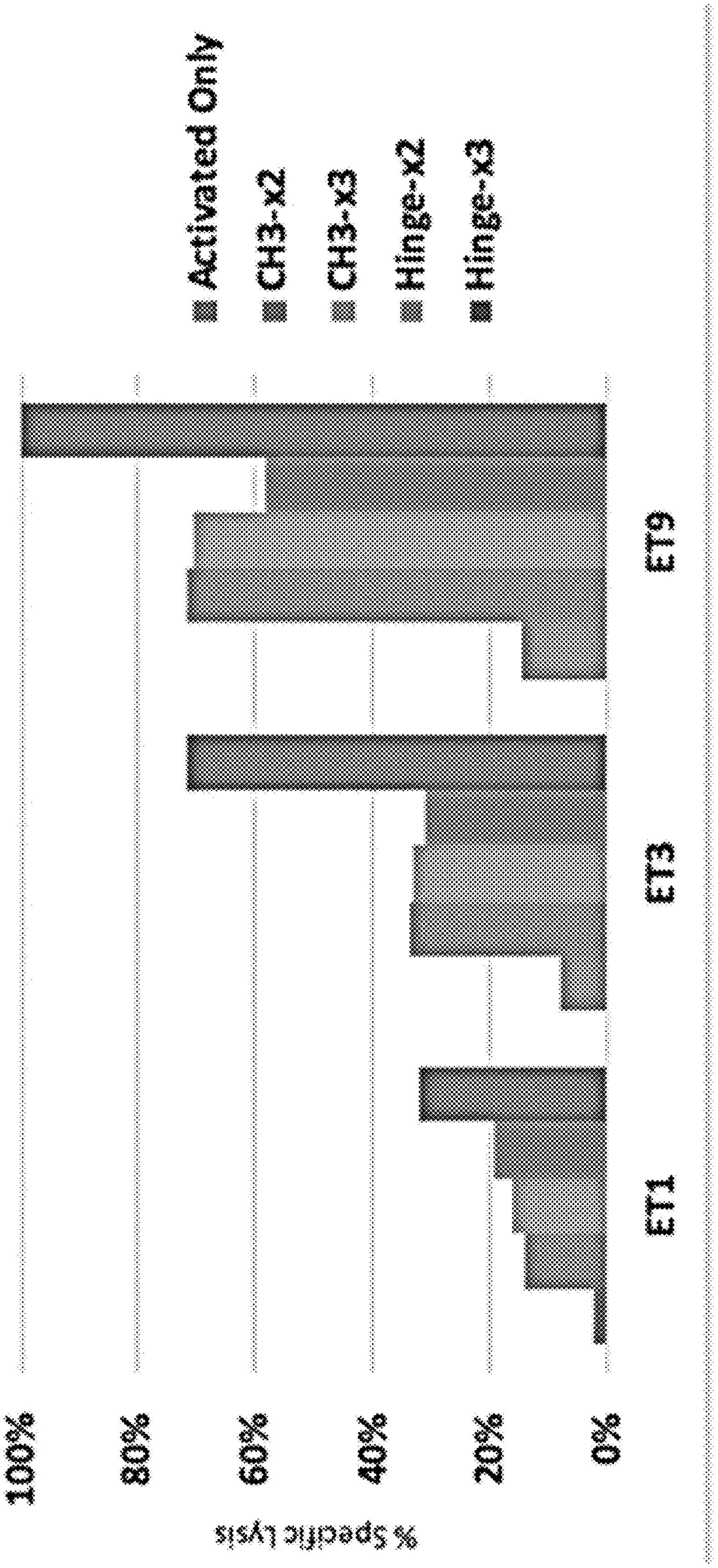
FIG. 8C and FIG. 8D shows a comparison of $2^{nd}$ and $3^{rd}$ generation CARs in a chromium release assay using MEC-1 cells that express ROR-1 (C), or lack expression of ROR-1 (D); for both 8C and 8D Left to Right: activated only; CH3 only $2^{nd}$ gen CAR; CH3 only $3^{rd}$ gen CAR; hinge only $2^{nd}$ gen CAR; hinge only $3^{rd}$ gen CAR.
Figure 8D:
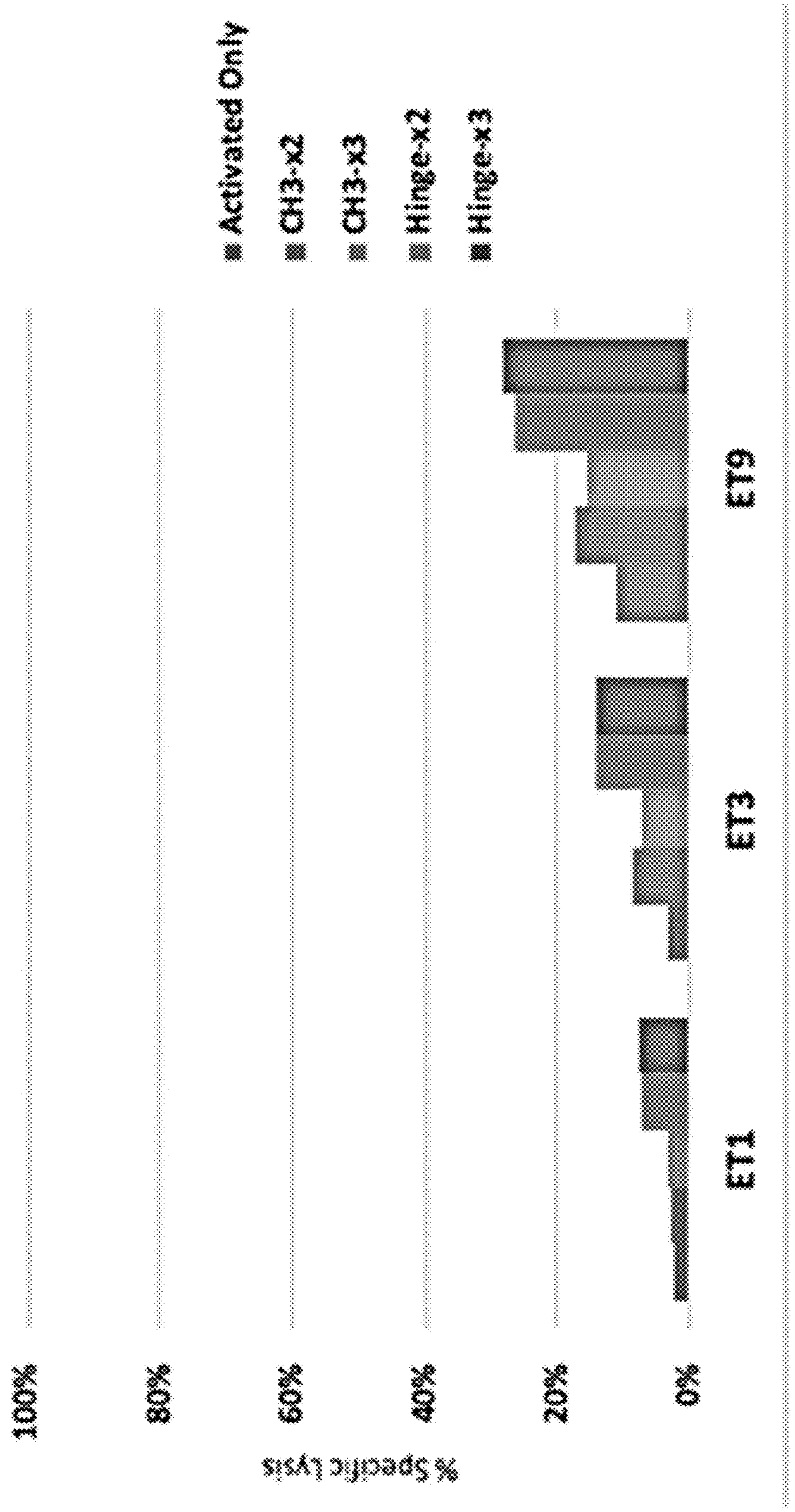
Figure 8E:
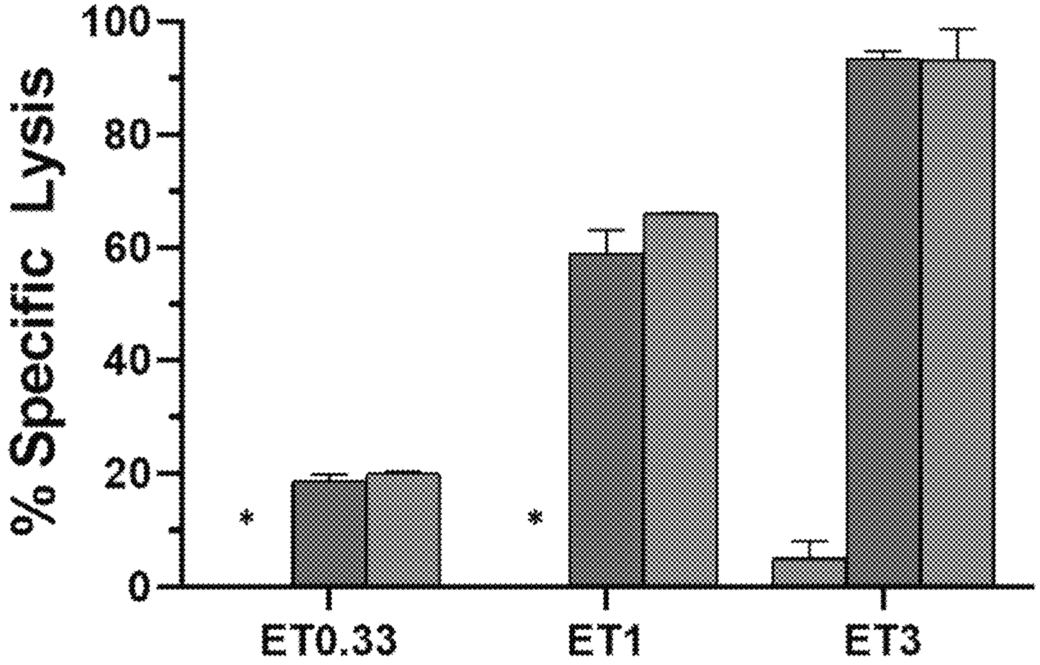
FIG. 8E shows in vitro cell killing activity of ROR1 CAR-T cells in a 4 hr chromium release assay from T cells of two healthy donors transduced with a second-generation CAR. Left-bar, Activated cells only; middle-bar, donor one; right-bar, donor two. Asterisk indicates bars not visible due to low level of killing.

FIG. 8C shows the effect on cytotoxicity of a $2^{nd}$ or $3^{rd}$ generation anti-ROR-1 CAR. FIG. 8C shows a similar experimental setup as in FIGS. 8A and 8B except comparing the hinge or CH3 as a $2^{nd}$ generation CAR (4-1BB intracellular signaling domain only) or a $3^{rd}$ generation CAR (both 4-1BB and CD28 intracellular signaling domains). There is no difference between a $2^{nd}$ and $3^{rd}$ generation CAR for constructs with the full CH3-hinge, however the $3^{rd}$ generation format showed improved killing compared to the $2^{nd}$ generation format for constructs that have hinge only and no CH3. FIG. 8D shows the absence of killing of MEC-1 cells that do not express ROR-1, indicating that these CARs are specific as well. FIG. 8E. cell killing of MEC1-ROR1 cells by CAR T from two different donors.

Figure 9A:
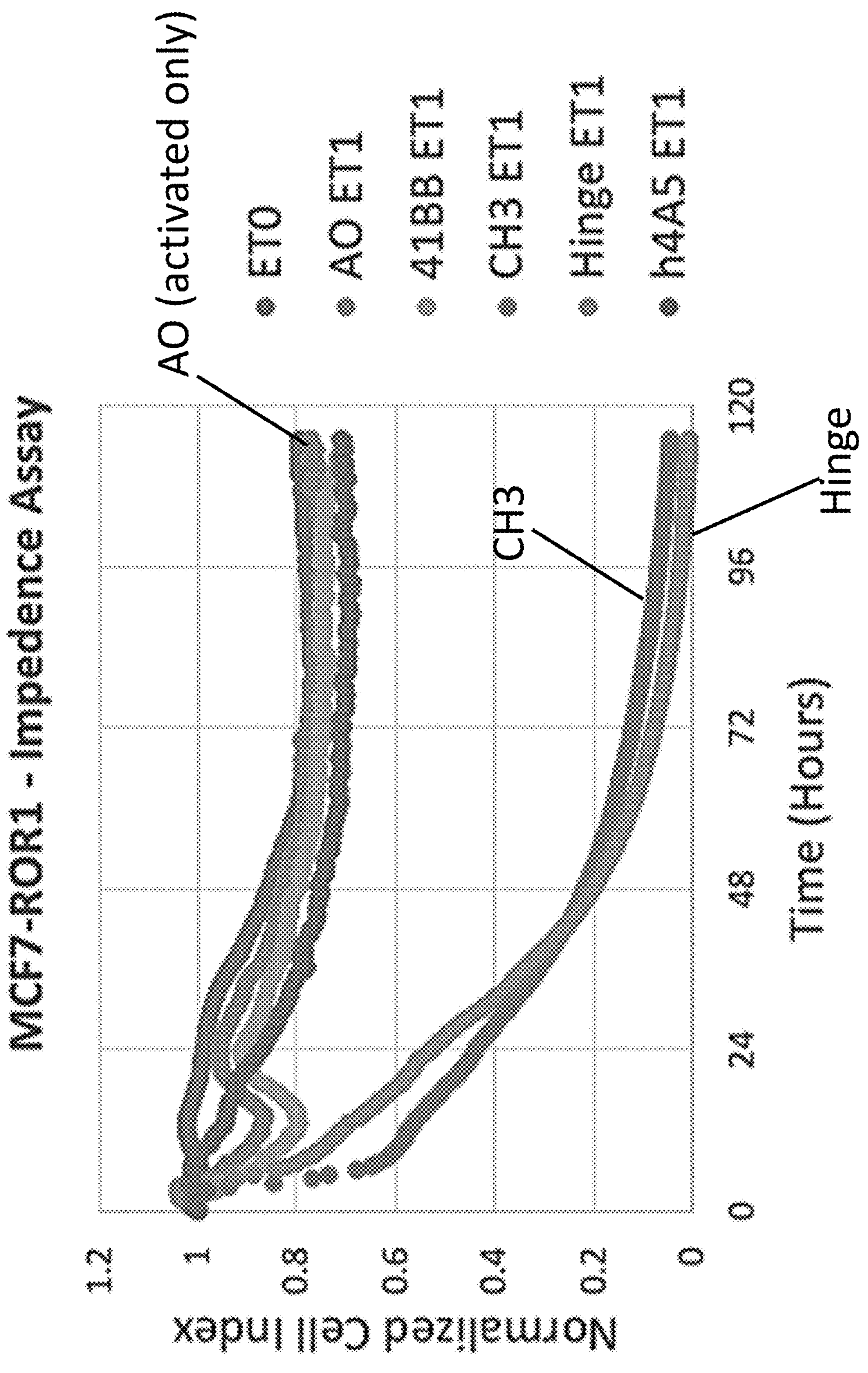
FIG. 9A and FIG. 9B show graphs of cell viability or death rate of MCF7 target cells that express ROR-1 (FIG. 9A), or lack ROR-1 expression (FIG. 9B) upon treatment with ROR1 CAR-T. Data shown is an impedance-based cytotoxicity assay.
Figure 9B:
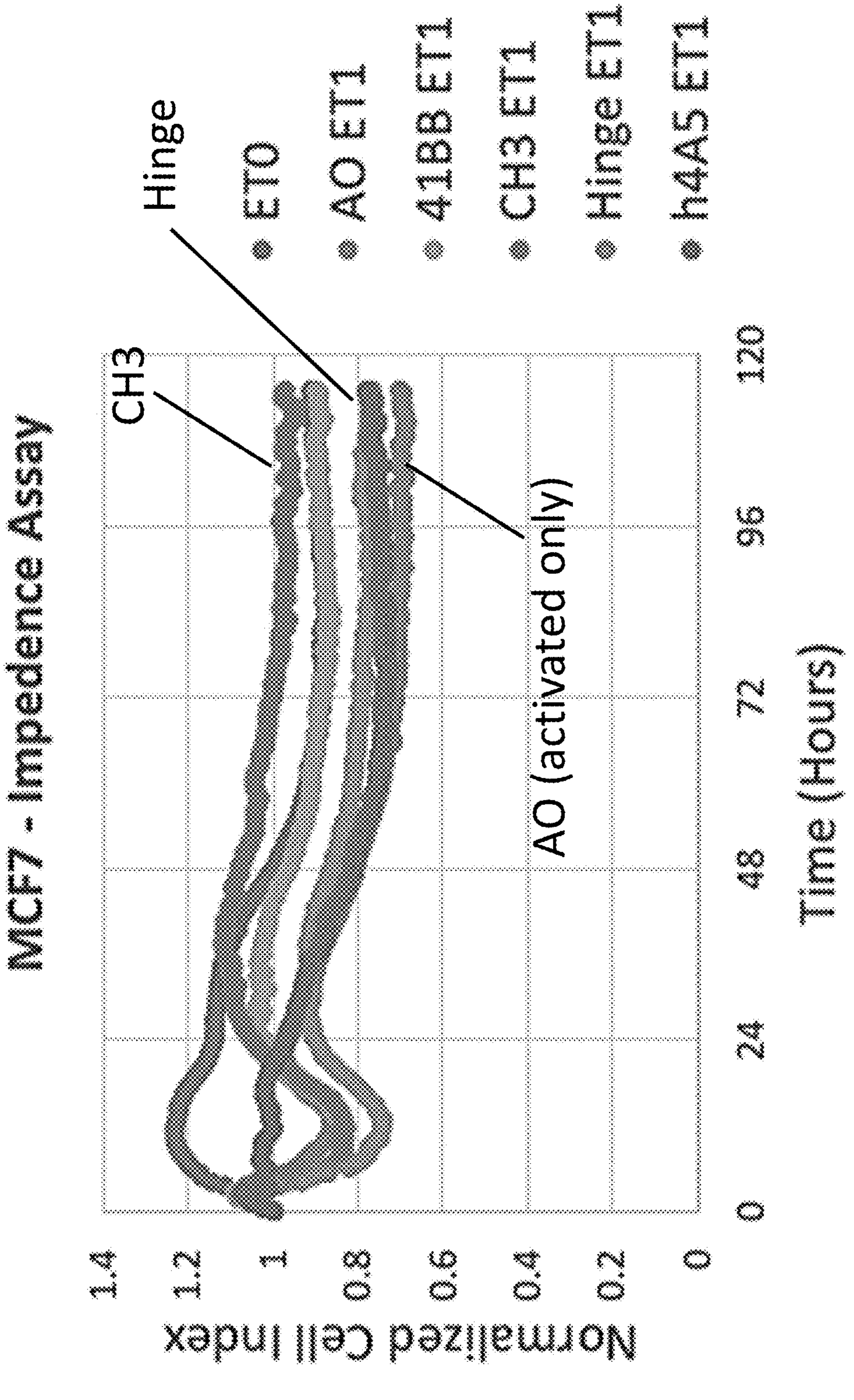
Figure 9C:
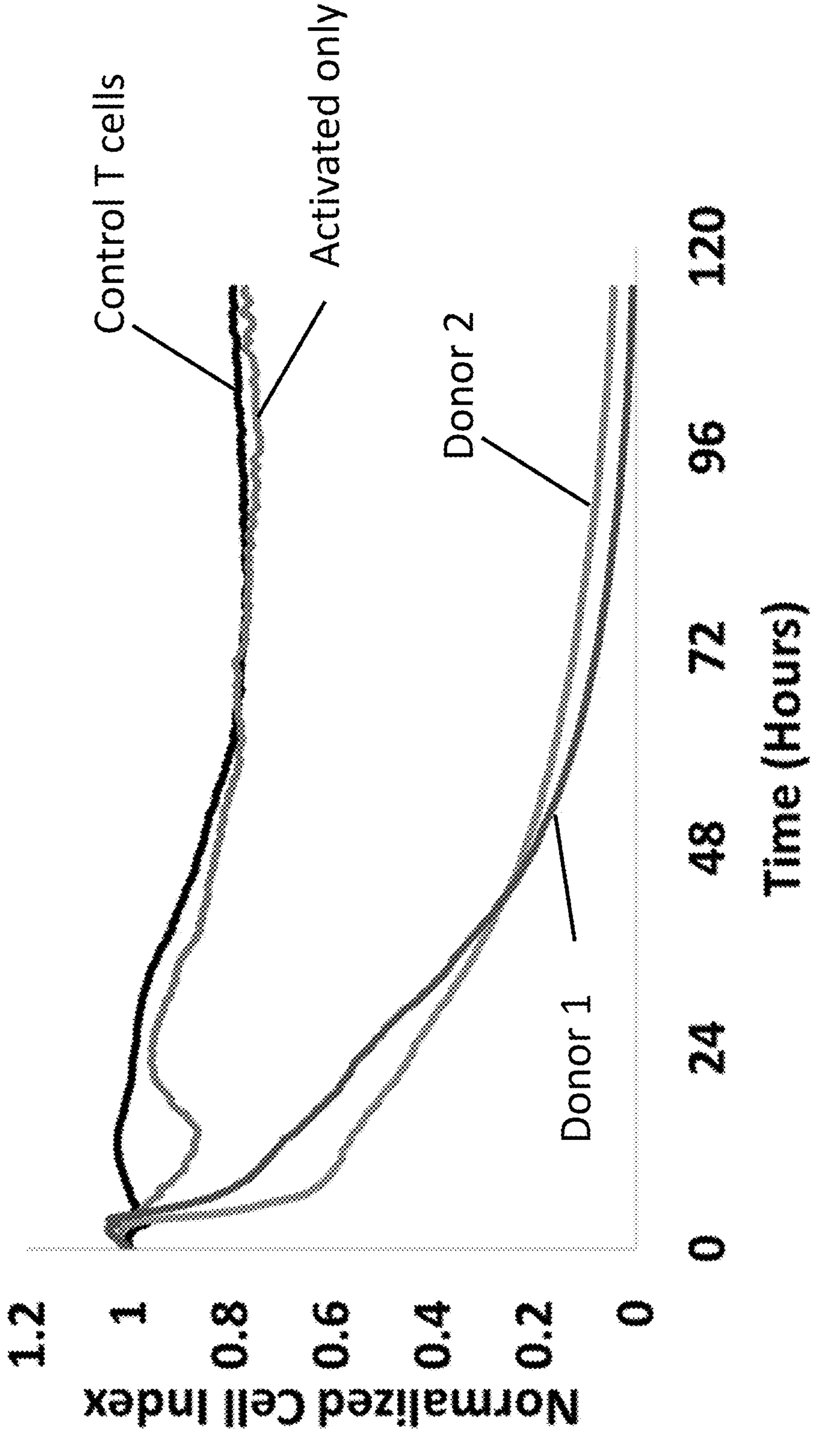
FIG. 9C shows a graph of cell death rate of MCF7 target cells that express ROR-1 by CAR-T cells generated from two different donors.

As shown in FIG. 9A anti-ROR-1 CARs kill MCF-7 ROR-1 cells. This figure shows the specific killing by anti-ROR-1 T-cell CARs with different spacer lengths, generated as described in Example 1, against MCF-7/ROR-1 breast cancer cells. These results were generated through the use of a 96-h impedance assay (ACEA). In this study anti-ROR-1 CARs that express the hinge and CH3 domains have the greatest activity against the ROR-1 positive cells. As used in FIG. 9A, "CH3" refers to a CAR-T construct utilizing Spacer CH3, containing Spacer #3 (SEQ ID NO:29) and the CH3 region of human IgG4; "Hinge" refers to CAR-T construct utilizing Spacer #3 (Hinge) without human IgG4 CH2 or CH3; "ET1" refers to an effector to target ratio of 1 to 1 for anti-ROR-1 CAR-T cells against the target cells in the cytotoxicity assay. FIG. 9B shows that the killing observed in FIG. 9A is specific as MCF-7 cells that do not express ROR-1 are not killed by anti-ROR-1 CAR-T cells. FIG. 9C shows killing from CAR T cells generated from two different healthy donors.

Figure 10:
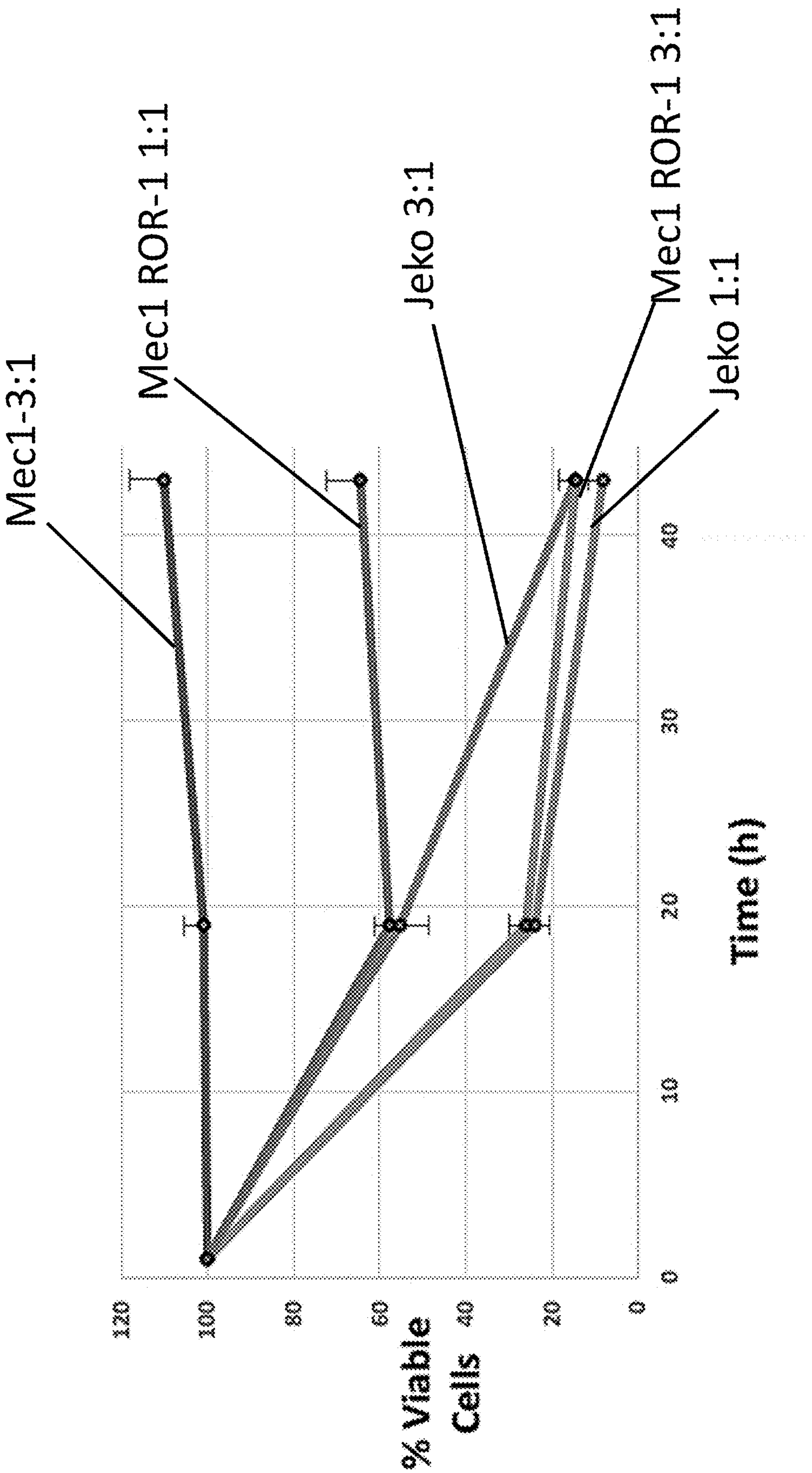
FIG. 10 shows a graph of cell viability of MEC-1 or Jeko cells upon treatment with anti-ROR-1 CAR-T cells at different effector to target ratios.

FIG. 10 illustrates that T lymphocytes expressing anti-ROR-1 CARs kill MEC1/ROR-1 cells and Jeko cells, which naturally express ROR-1, at different effector to target ratios.

Example 3: In Vivo Activity of Chimeric Antigen Receptor Modified T-Cells (Car-T) that Target ROR-1

Figure 11A:
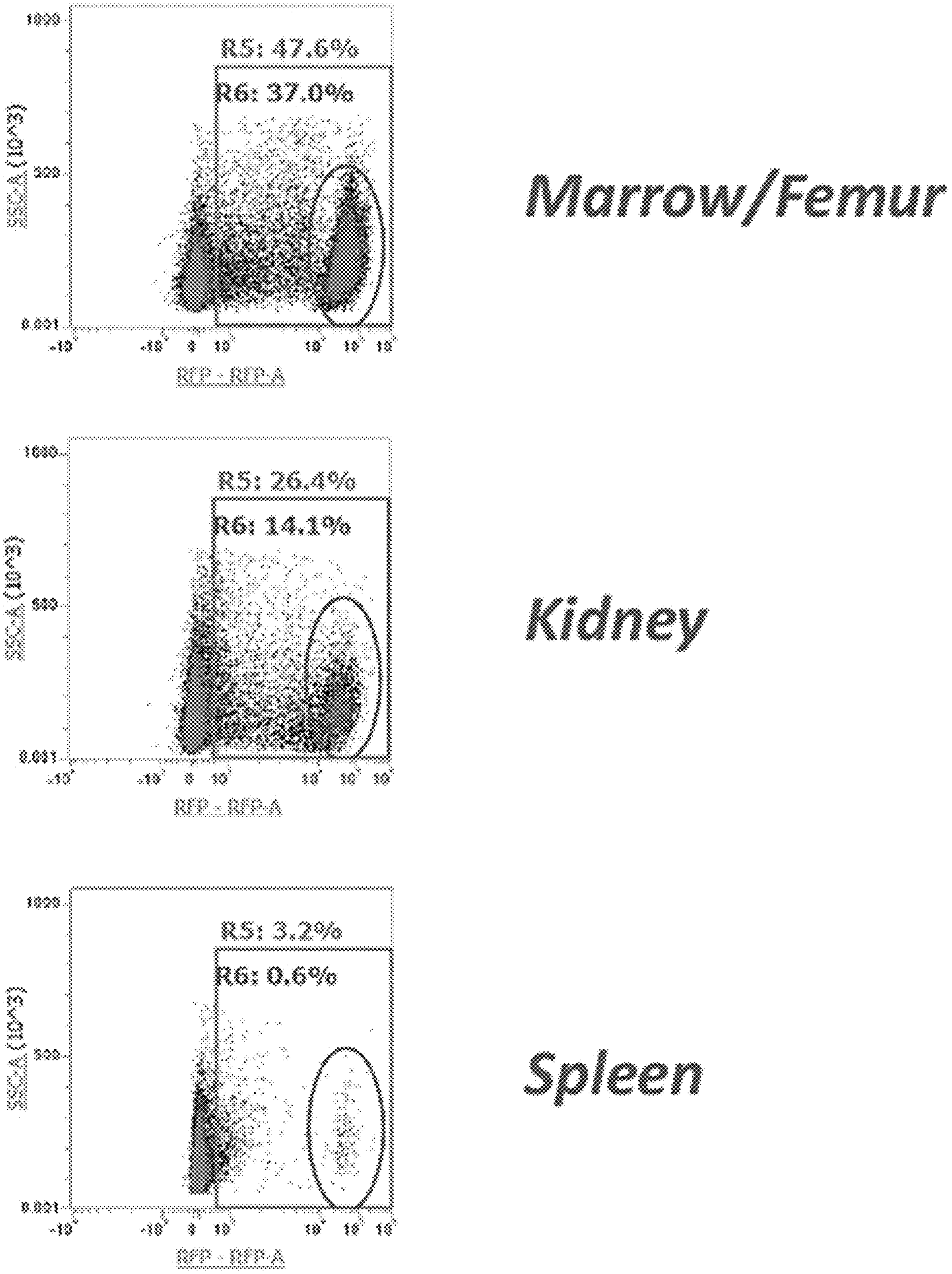
FIG. 11A shows that MEC-1/ROR-1 cells persist in bone marrow, kidney, and spleen of mice injected with $1\times10^6$ MEC-1/ROR-1-luciferase cells.
Figure 11B:
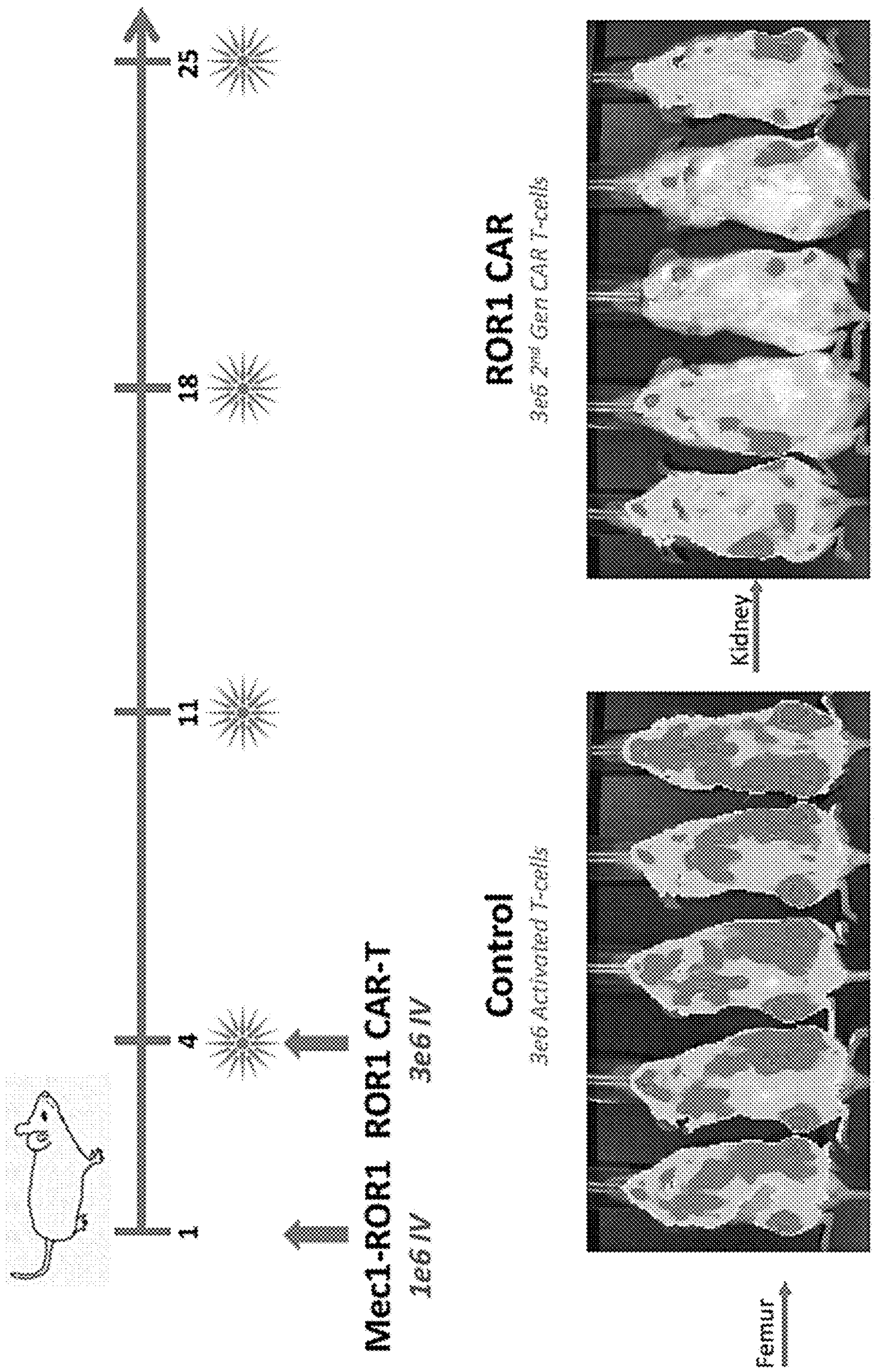
FIG. 11B illustrates a schematic of the in vivo experiments and bioluminescence in mice that were treated with $3\times10^6$ activated cells only (bottom left), or anti-ROR-1 CAR-T cells (bottom right).

To test the ROR1 T-cell CARs in vivo, luciferase/RFP bi-specific lentiviral expression vectors to modify human MEC1-ROR1 leukemia cells (Yu et al., *J Clin Invest,* 2015) were created. When injected into immune-deficient NSG mice, MEC1-ROR1 cells infiltrate the marrow (femur), kidney, spleen, and liver, generating a progressive and fatal leukemia/lymphoma. As shown in FIG. 11A, when injected into immune-deficient mice, this highly active cell-line rapidly expands into the bone marrow (femur), kidney, spleen, liver and blood with the animals succumb to the leukemia within about 3-weeks. In vivo experiments were conducted as in FIG. 11B (top), briefly, mice were injected with $1\times10^6$ ROR-1/MEC1-luciferase cells on day 1, followed by $1\times10^6$ or $3\times10^6$ anti ROR-1 CAR-T cells on day 4. Tumor growth was measured using bioluminescence of the modified MEC cells at subsequent timepoints.

Figure 12:
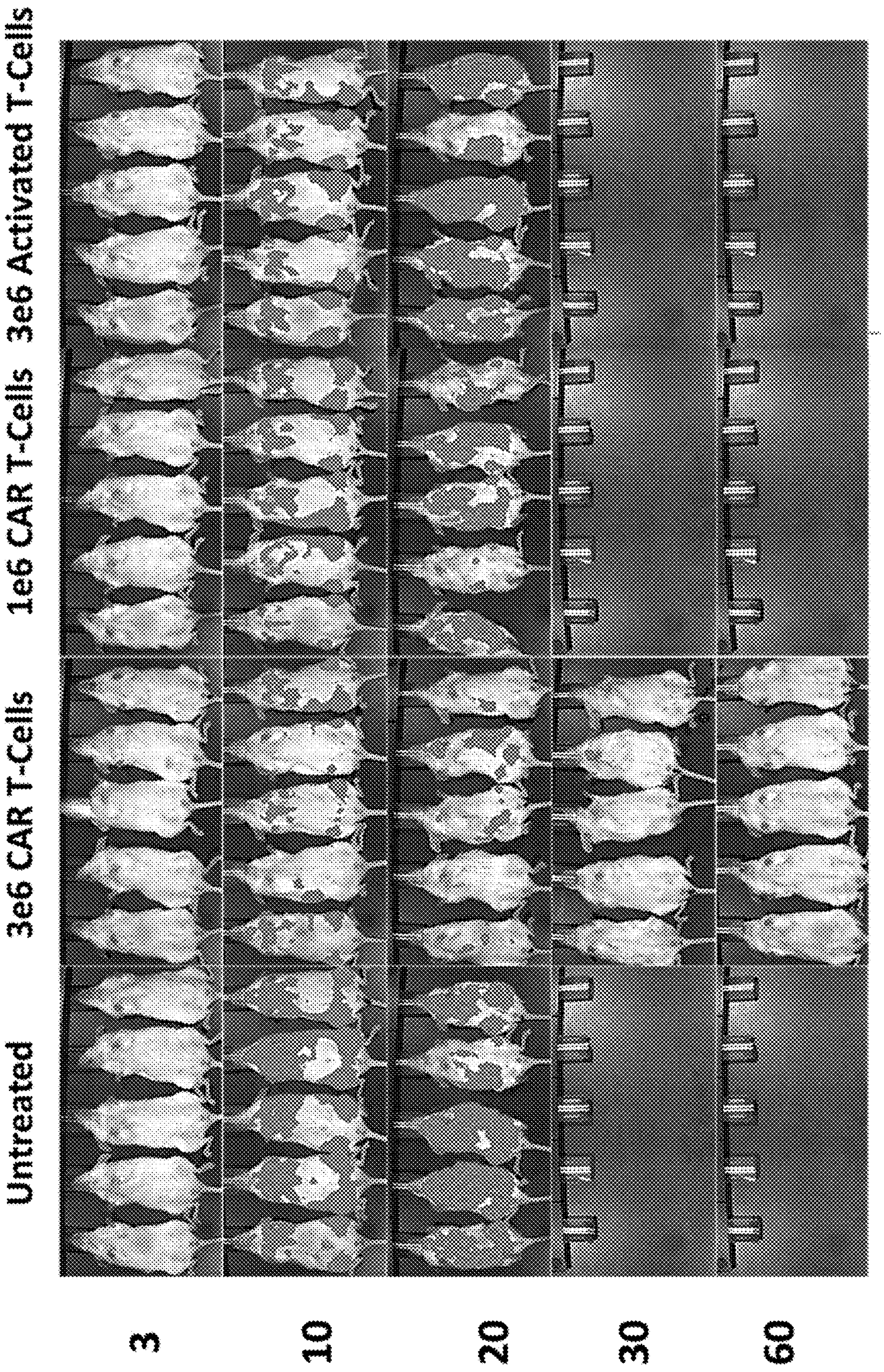
FIG. 12 shows bioluminescence imaging of mice inoculated with MEC1-ROR1 cells and with ROR-1 CAR T-cells. Animals treated with ROR-1 CAR-T cells had reduced tumor burden compared to controls. The highest dose ($3\times10^6$ CAR-Ts) cohort had only minimal amounts of disease at the end of the study.
Figure 13:
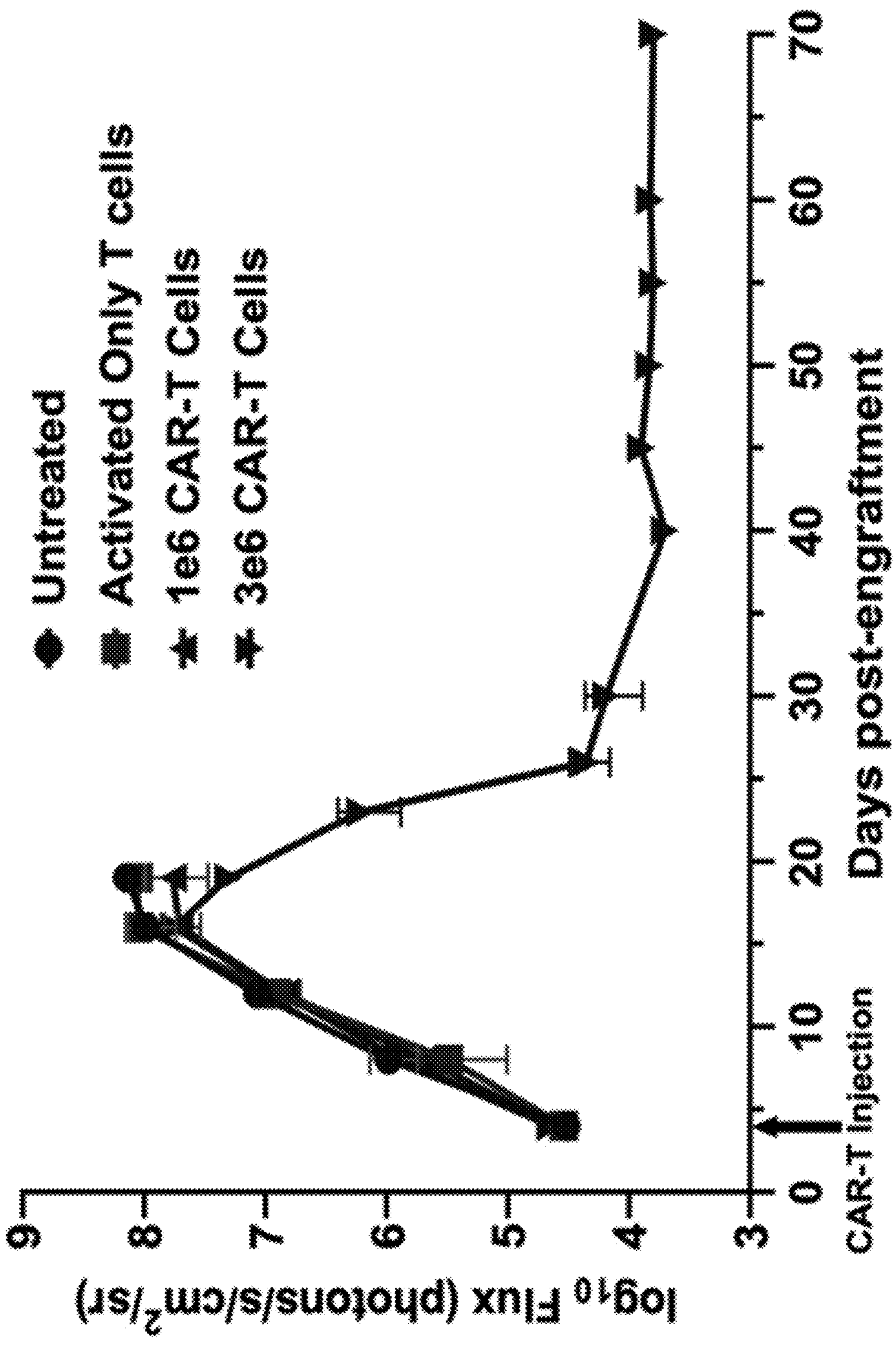
FIG. 13 shows a time course of tumor volume (photon flux) in mice untreated, treated with activated cells only, $1\times10^6$, or $3\times10^6$ anti-ROR-1 CAR T cells. Mice treated with $3\times10^6$ ROR-1 CAR-T reduced the leukemic burden to background levels by day 30 and that this minimal amount of disease was maintained for the duration of the study. Animals in the control groups (untreated, activated cells, or $1\times10^6$ dose) had to be sacrificed on day 20.
Figure 14:
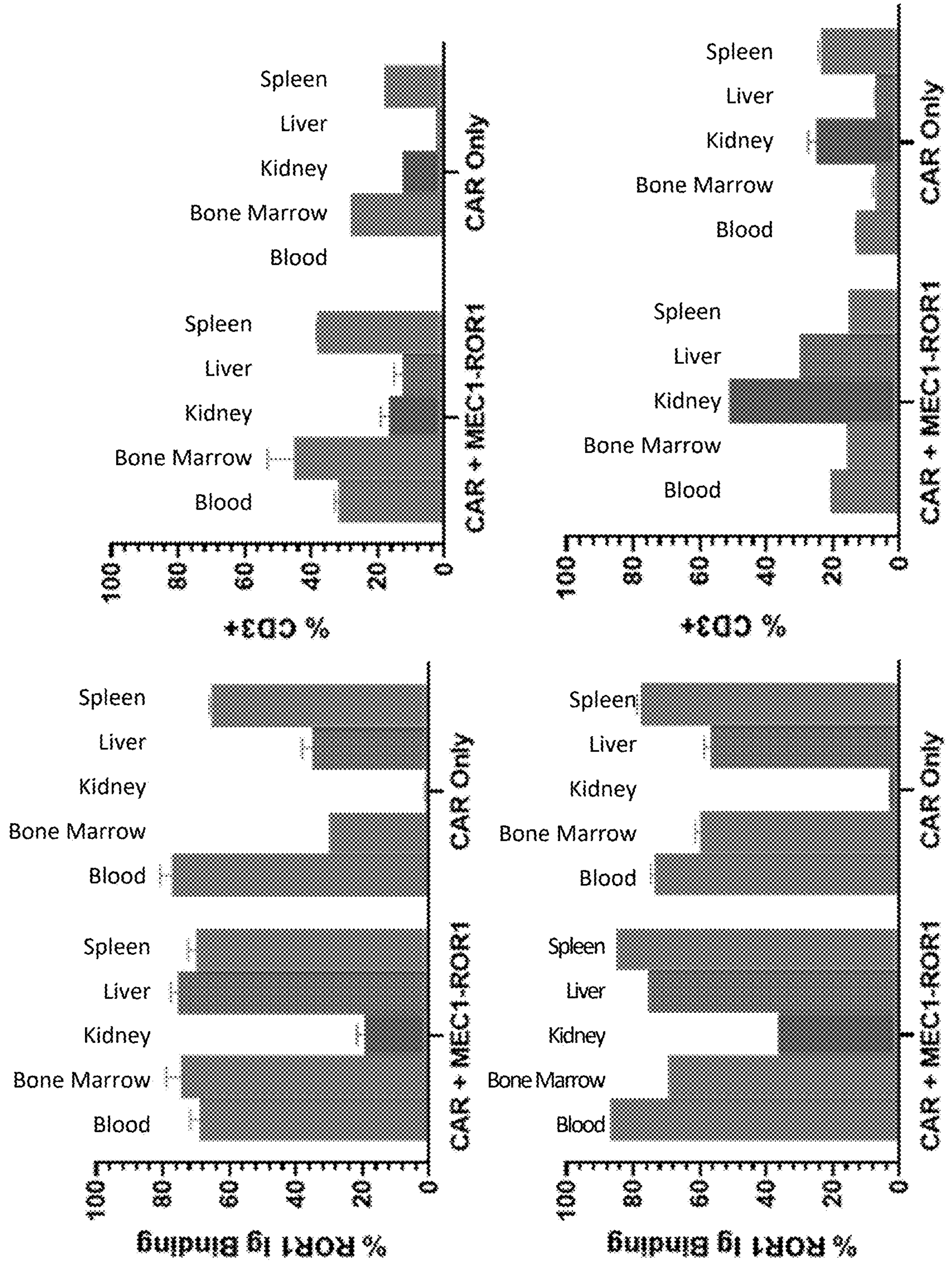
FIG. 14 shows ROR-1 CAR-T expression in mouse tissues at various times in mice. Following ROR-1 CAR-T administration, animals were sacrificed on days 11 (top), and 25 (bottom), blood and organs were collected and subjected to flow analysis for CAR expression and confirmatory ROR1 binding activity. The ROR-1 CAR-T cell number was substantially greater in mice bearing MEC-1 ROR1 cells (CAR+MEC1-ROR1) vs control (CAR only) demonstrating elevated expansion of ROR-1 CAR-T cells in animals with tumor burden. Bars represent the mean values from the five mice in each group and error bars represent the S.E of the mean.

Mice that were injected with the tumor cells responded in a dose dependent manner to $2^{nd}$ generation CAR-T cells from the in vitro studies. $3\times10^6$ anti-ROR-1 CAR T cells were able to clear luciferase expressing ROR-1/MEC cells as shown in FIGS. 12 and 13. By week 3, the rapidly expanding leukemic cells are cleared from the marrow, the remaining leukemic cells are undetectable by week 4, and animals survive greater than 90 days vs ~21 days in the absence of these CAR-T cells. FIG. 14 shows that anti-ROR1 CAR-T cells were major components of the animals' marrow and kidneys by day 11 and by day 18. Additionally, the concentration of the CAR-T cells was substantially greater in the mice that were pretreated with MEC-1 ROR1 cells (left panels) vs mock control (right panels) demonstrating the elevated expansion of the CAR-T in animals bearing leukemic cells.

To summarize the results presented here:

A single injection of $3\times10^6$ anti-ROR1 4-1BB CAR T-cells unsupported, without conditioning or cytokine supplementation regimens, expanded in the animals bearing MEC1-ROR1 xenografts and homed to the sites of MEC1-ROR1 disease activity.

By week four, the rapidly expanding leukemic cells were cleared from the major tissue reservoirs including the marrow, kidneys and spleen.

The CAR-T treated animals survived greater than 90 days vs ~21 days for those animals that received only non-transduced activated T-cells or were untreated controls.

The administered CAR T-products were highly active and detected in mouse tissues months after injection These studies have been expanded to other lymphoid tumor cell lines including the ROR-1 expressing JeKo cells.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

```
INFORMAL SEQUENCE LISTING:
UC961 VL:
(SEQ ID NO: 21)
DIVMTQTPLSLPVTPGEPASISCRASKSISKYLAWYQQKPGQAPRLLIYSG

STLQSGIPPRFSGSGYGTDFTLTINNIESEDAAYYFCQQHDESPYTFGEGT

KVEIK

Linker #3:
(SEQ ID NO: 24)
GGGGSGSTSGSGKPGSGEGSTKGGGGS
```

-continued

UC961 VH:
(SEQ ID NO: 27)
QVQLQESGPGLVKPSQTLSLTCTVSGYAFTAYNIHWVRQAPGQGLEWMGSF

DPYDGGSSYNQKFKDRLTISKDTSKNQVVLTMTNMDPVDTATYYCARGWYY

FDYWGHGTLVTVSS

Spacer #3 (or "Hinge/Short"):
(SEQ ID NO: 29)
VDESKYGPPCPPCP

Spacer CH3:
(SEQ ID NO: 41)
VDESKYGPPCPPCPLPPSQEEMTKNQVSLTCLVKGFYPSDIAVEWESNGQP

ENNYKTTPPVLDSDGSFFLYSRLTVDKSRWQEGNVFSCSVMHEALHNHYTQ

KSLSLSLGK

Spacer CH2CH3 (or "Long/Full"):
(SEQ ID NO: 42)
VDESKYGPPCPPCPAPEFLGGPSVFLFPPKPKDTLMISRTPEVTCVVVDVS

QEDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCLV

KGFYPSDIAVEWESNGQPENNYKTTPPVLDSDGSFFLYSRLTVDKSRWQEG

NVFSCSVMHEALHNHYTQKSLSLSLGK

UC961 CDR L1:
(SEQ ID NO: 43)
KSISKY

UC961 CDR L2:
(SEQ ID NO: 44)
SGS

UC961 CDR L3:
(SEQ ID NO: 45)
QQHDESPY

UC961 CDR H1:
(SEQ ID NO: 46)
GYAFTAYN

UC961 CDR H2:
(SEQ ID NO: 47)
FDPYDGGS

UC961 CDR H3:
(SEQ ID NO: 48)
GWYYFDY

4A5 CDR L1:
(SEQ ID NO: 49)
PDINSY

4A5 CDR L2:
(SEQ ID NO: 50)
RAN

4A5 CDR L3:
(SEQ ID NO: 51)
LQYDEFPYT

4A5 CDR H1:
(SEQ ID NO: 52)
GFTFSSYA

4A5 CDR H2:
(SEQ ID NO: 53)
ISRGGTT

4A5 CDR H3:
(SEQ ID NO: 54)
YDYDGYYAMDY

-continued

Full-length human ROR-1 Protein (SEQ ID NO: 55):
MHRPRRRGTRPPLLALLAALLLAARGAAAQETELSVSAELVPTSSWNISSE

LNKDSYLTLDEPMNNITTSLGQTAELHCKVSGNPPPTIRWFKNDAPVVQEP

RRLSFRSTIYGSRLRIRNLDTTDTGYFQCVATNGKEVVSSTGVLFVKFGPP

PTASPGYSDEYEEDGFCQPYRGIACARFIGNRTVYMESLHMQGEIENQITA

AFTMIGTSSHLSDKCSQFAIPSLCHYAFPYCDETSSVPKPRDLCRDECEIL

ENVLCQTEYIFARSNPMILMRLKLPNCEDLPQPESPEAANCIRIGIPMADP

INKNHKCYNSTGVDYRGTVSVTKSGRQCQPWNSQYPHTHTFTALRFPELNG

GHSYCRNPGNQKEAPWCFTLDENFKSDLCDIPACDSKDSKEKNKMEILYIL

VPSVAIPLAIALLFFFICVCRNNQKSSSAPVQRQPKHVRGQNVEMSMLNAY

KPKSKAKELPLSAVRFMEELGECAFGKIYKGHLYLPGMDHAQLVAIKTLKD

YNNPQQWMEFQQEASLMAELHHPNIVCLLGAVTQEQPVCMLFEYINQGDLH

EFLIMRSPHSDVGCSSDEDGTVKSSLDHGDFLHIAIQIAAGMEYLSSHFFV

HKDLAARNILIGEQLHVKISDLGLSREIYSADYYRVQSKSLLPIRWMPPEA

IMYGKFSSDSDIWSFGVVLWEIFSFGLQPYYGFSNQEVIEMVRKRQLLPCS

EDCPPRMYSLMTECWNEIPSRRPRFKDIHVRLRSWEGLSSIITSSTTPSGG

NATTQTTSLSASPVSNLSNPRYPNYMFPSQGITPQGQIAGFIGPPIPQNQR

FIPINGYPIPPGYAAFPAAHYQPTGPPRVIQHCPPPKSRSPSSASGSTSTG

HVTSLPSSGSNQEANIPLLPHMSIPNHPGGMGITVFGNKSQKPYKIDSKQA

SLLGDANIIIGIITESMISAEL 21 amino acid stretch of human ROR-1 including
glutamic acid at position 138 (SEQ ID NO: 56):
VATNGKEVVSSTGVLFVKFGP 15 amino acid stretch of human ROR-1 including
glutamic acid at position 138 (SEQ ID NO: 57):
EVVSSTGVLFVKFGP

P EMBODIMENTS

P Embodiment 1. A recombinant protein comprising: (i) an antibody region comprising: (a) a light chain variable domain comprising a CDR L1 as set forth in SEQ ID NO: 43, a CDR L2 as set forth in SEQ ID NO:44 and a CDR L3 as set forth in SEQ ID NO: 45; and (b) a heavy chain variable domain comprising a CDR H1 as set forth in SEQ ID NO: 46, a CDR H2 as set forth in SEQ ID NO:47, and a CDR H3 as set forth in SEQ ID NO: 48; and (ii) a transmembrane domain.

P embodiment 2. A recombinant protein comprising: (i) an antibody region comprising: (a) a light chain variable domain comprising a CDR L1 as set forth in SEQ ID NO: 49, a CDR L2 as set forth in SEQ ID NO:50 and a CDR L3 as set forth in SEQ ID NO: 51; and (b) a heavy chain variable domain comprising a CDR H1 as set forth in SEQ ID NO: 52, a CDR H2 as set forth in SEQ ID NO:53, and a CDR H3 as set forth in SEQ ID NO: 54; and (ii) a transmembrane domain.

P embodiment 3. The recombinant protein of P embodiment 1, wherein the C-terminus of said light chain variable domain is bound to the N-terminus of said heavy chain variable domain.

P embodiment 4. The recombinant protein of any one of P embodiments 1-3, wherein said light chain variable domain is covalently bound to said heavy chain variable domain through a chemical linker.

P embodiment 5. The recombinant protein of any one of P embodiments 1-4, wherein said chemical linker is a peptide linker.

P embodiment 6. The recombinant protein of P embodiment 5, wherein said peptide linker has the sequence of SEQ ID NO:24.

P embodiment 7. The recombinant protein of any one of P embodiments 1-6, wherein the C-terminus of said heavy chain variable domain is bound to the N-terminus of said transmembrane domain.

P embodiment 8. The recombinant protein of any one of P embodiments 1-7, wherein said heavy chain variable domain is covalently bound to said transmembrane domain through a spacer domain.

P embodiment 9. The recombinant protein of P embodiment 8, wherein said spacer domain comprises an antibody domain.

P embodiment 10. The recombinant protein of P embodiment 9, wherein said antibody domain comprises a hinge domain, a constant heavy chain 3 (CH3) domain, a constant heavy chain 2 (CH2) domain or any combination thereof.

P embodiment 11. The recombinant protein of P embodiment 9 or 10, wherein said antibody domain consists of a hinge domain.

P embodiment 12. The recombinant protein of P embodiment 9 or 10, wherein said antibody domain consists of a hinge domain and a constant heavy chain 3 (CH3) domain.

P embodiment 13. The recombinant protein of P embodiment 9 or 10, wherein said antibody domain consists of a hinge domain, a constant heavy chain 3 (CH3) domain and a constant heavy chain 2 (CH2) domain.

P embodiment 14. The recombinant protein of any one of P embodiments 9-13, wherein said spacer domain comprises the sequence of SEQ ID NO:29, SEQ ID NO:41 or SEQ ID NO:42.

P embodiment 15. The recombinant protein of any one of P embodiments 9-13, wherein said spacer domain has the sequence of SEQ ID NO:29, SEQ ID NO:41 or SEQ ID NO: 42.

P embodiment 16. The recombinant protein of any one of P embodiments 1-15, wherein said light chain variable domain comprises the sequence of SEQ ID NO:21.

P embodiment 17. The recombinant protein of any one of P embodiments 1-16, wherein said light chain variable domain has the sequence of SEQ ID NO:21.

P embodiment 18. The recombinant protein of any one of P embodiments 1-17, wherein said heavy chain variable domain comprises the sequence of SEQ ID NO:27.

P embodiment 19. The recombinant protein of any one of P embodiments 1-18, wherein said heavy chain variable domain has the sequence of SEQ ID NO:27.

P embodiment 20. The recombinant protein of any one of P embodiments 2-13, wherein said light chain variable domain comprises the sequence of SEQ ID NO:19.

P embodiment 21. The recombinant protein of any one of P embodiments 2-13 or 20, wherein said light chain variable domain has the sequence of SEQ ID NO: 19.

P embodiment 22. The recombinant protein of any one of P embodiments 2-13, wherein said light chain variable domain comprises the sequence of SEQ ID NO:20.

P embodiment 23. The recombinant protein of any one of P embodiments 2-13 or 22, wherein said light chain variable domain has the sequence of SEQ ID NO:20.

P embodiment 24. The recombinant protein of any one of P embodiments 2-13, wherein said heavy chain variable domain comprises the sequence of SEQ ID NO:25.

P embodiment 25. The recombinant protein of any one of P embodiments 2-13 or 24, wherein said heavy chain variable domain has the sequence of SEQ ID NO:25.

P embodiment 26. The recombinant protein of any one of P embodiments 2-13, wherein said heavy chain variable domain comprises the sequence of SEQ ID NO:26.

P embodiment 27. The recombinant protein of any one of P embodiments 2-13 or 26, wherein said heavy chain variable domain has the sequence of SEQ ID NO:26.

P embodiment 28. The recombinant protein of any one of P embodiments 1-27, wherein said transmembrane domain is a CD8α transmembrane domain, a CD28 transmembrane domain, a CD4 transmembrane domain or a CD3 transmembrane domain or any combination thereof.

P embodiment 29. The recombinant protein of any one of P embodiments 1-28, wherein said transmembrane domain is a CD28 transmembrane domain.

P embodiment 30. The recombinant protein of P embodiment 29, wherein said CD28 transmembrane domain comprises the sequence of SEQ ID NO:32.

P embodiment 31. The recombinant protein of P embodiment 29, wherein said CD28 transmembrane domain has the sequence of SEQ ID NO:32.

P embodiment 32. The recombinant protein of any one of P embodiments 1-31, further comprising one or more intracellular co-stimulatory signaling domains.

P embodiment 33. The recombinant protein of P embodiment 32, wherein said one or more intracellular co-stimulatory signaling domains are a 4-1BB intracellular co-stimulatory signaling domain, a CD28 intracellular co-stimulatory signaling domain, a ICOS intracellular co-stimulatory signaling domain, an OX-40 intracellular co-stimulatory signaling domain or any combination thereof.

P embodiment 34. The recombinant protein of P embodiment 32 or 33, comprising a 4-1BB intracellular co-stimulatory signaling domain.

P embodiment 35. The recombinant protein of P embodiment 34, wherein said 4-1BB intracellular co-stimulatory signaling domain comprises the sequence of SEQ ID NO:33.

P embodiment 36. The recombinant protein of P embodiment 34 or 35, wherein said 4-1BB intracellular co-stimulatory signaling domain has the sequence of SEQ ID NO:33.

P embodiment 37. The recombinant protein of P embodiment 32, comprising a CD28 intracellular co-stimulatory signaling domain and a 4-1BB intracellular co-stimulatory signaling domain.

P embodiment 38. The recombinant protein of any one of P embodiments 1-37, further comprising an intracellular T-cell signaling domain.

P embodiment 39. The recombinant protein of P embodiment 38, wherein said intracellular T-cell signaling domain is a CD3ζ intracellular T-cell signaling domain.

P embodiment 40. The recombinant protein of P embodiment 39, wherein said CD3ζ intracellular T-cell signaling domain comprises the sequence of SEQ ID NO:34.

P embodiment 41. The recombinant protein of P embodiment 39, wherein said CD3ζ intracellular T-cell signaling domain has the sequence of SEQ ID NO:34.

P embodiment 42. The recombinant protein of any one of P embodiments 1-41, wherein said recombinant protein binds to a cell.

P embodiment 43. The recombinant protein of P embodiment 42, wherein said cell is a cancer cell.

P embodiment 44. The recombinant protein of P embodiment 43, wherein said cancer cell is a leukemia cell, a lymphoma cell, a chronic lymphocytic leukemia (CLL) cell, an adult acute myeloid leukemia (AML) cell, an acute lymphoblastic leukemia (ALL) cell, a mantle cell lymphoma (MCL) cell, a multiple myeloma cell, an ovarian cancer cell, a colon cancer cell, a lung cancer cell, a skin cancer cell, a pancreatic cancer cell, a testicular cancer cell, a bladder cancer cell, a uterine cancer cell, a prostate cancer cell, a breast cancer cell, or an adrenal cancer cell.

P embodiment 45. The recombinant protein any one of P embodiments 1-44, wherein said recombinant protein forms part of a cell.

P embodiment 46. The recombinant protein any one of P embodiments 1-46, wherein said recombinant protein forms part of a T cell.

P embodiment 47. An isolated nucleic acid encoding a recombinant protein of any one of P embodiments 1-46.

P embodiment 48. A pharmaceutical composition comprising a therapeutically effective amount of a recombinant protein of one of P embodiments 1-46, and a pharmaceutically acceptable excipient.

P embodiment 49. A method of treating cancer in a subject in need thereof, said method comprising administering to a subject a therapeutically effective amount of a recombinant protein of one of P embodiments 1-46, thereby treating cancer in said subject.

EMBODIMENTS

Embodiment 1. A chimeric antigen receptor comprising:

- an antigen binding region, wherein said antigen binding region specifically binds ROR-1 wherein said antigen binding region comprises a light chain variable domain and a heavy chain variable domain;
- wherein said light chain variable domain comprises a CDR L1 as set forth in SEQ ID NO:43, a CDR L2 as set forth in SEQ ID NO:44 and a CDR L3 as set forth in SEQ ID NO:45; and
- said heavy chain variable domain comprises a CDR H1 as set forth in SEQ ID NO:46, a CDR H2 as set forth in SEQ ID NO:47, and a CDR H3 as set forth in SEQ ID NO:48; or wherein said light chain variable domain comprises a CDR L1 as set forth in SEQ ID NO:49, a CDR L2 as set forth in SEQ ID NO:50 and a CDR L3 as set forth in SEQ ID NO:51; and said heavy chain variable domain comprising a CDR H1 as set forth in SEQ ID NO:52, a CDR H2 as set forth in SEQ ID NO:53, and a CDR H3 as set forth in SEQ ID NO:54;
- a spacer domain, wherein said spacer domain comprises a spacer of between 10 and 240 amino acids in length;
- a transmembrane domain; and
- an intracellular domain.

Embodiment 2. The chimeric antigen receptor of embodiment 1, wherein the spacer is between 14 and 120 amino acids in length.

Embodiment 3. The chimeric antigen receptor of embodiment 1 or 2, wherein said light chain variable domain is N-terminal of said heavy chain variable domain.

Embodiment 4. The chimeric antigen receptor of embodiment 3, wherein said light chain variable domain is covalently coupled to said heavy chain variable domain through a polypeptide linker.

Embodiment 5. The chimeric antigen receptor of embodiment 4, wherein said polypeptide linker consists of the sequence of SEQ ID NO:24.

Embodiment 6. The chimeric antigen receptor of any one of embodiments 1 to 5, wherein said spacer domain comprises an antibody domain.

Embodiment 7. The chimeric antigen receptor of embodiment 6, wherein said antibody domain comprises an immunoglobulin hinge domain, an immunoglobulin constant heavy chain 3 (CH3) domain, an immunoglobulin constant heavy chain 2 (CH2) domain, or any combination thereof.

Embodiment 8. The chimeric antigen receptor of embodiment 7, wherein said antibody domain consists of said immunoglobulin hinge domain.

Embodiment 9. The chimeric antigen receptor of embodiment 7, wherein said antibody domain consists of an immunoglobulin hinge domain and said immunoglobulin constant heavy chain 3 (CH3) domain.

Embodiment 10. The chimeric antigen receptor of embodiment 7, wherein said antibody domain consists of said immunoglobulin hinge domain, said immunoglobulin constant heavy chain 3 (CH3) domain and said immunoglobulin constant heavy chain 2 (CH2) domain.

Embodiment 11. The chimeric antigen receptor of embodiment 7, wherein said spacer domain comprises the sequence of SEQ ID NO:29, SEQ ID NO:41 or SEQ ID NO:42.

Embodiment 12. The chimeric antigen receptor of embodiment 7, wherein said spacer domain consists of the sequence of SEQ ID NO:29, SEQ ID NO:41 or SEQ ID NO:42.

Embodiment 13. The chimeric antigen receptor of any one of embodiments 7 to 12, wherein said light chain variable domain comprises an amino acid sequence at least about 90%, 95%, 97%, 98%, 99%, or 100% identical to SEQ ID NO:21.

Embodiment 14. The chimeric antigen receptor of any one of embodiments 7 to 12, wherein said light chain variable domain consists of the sequence of SEQ ID NO:21.

Embodiment 15. The chimeric antigen receptor of any one of embodiments 7 to 12, wherein said heavy chain variable domain comprises an amino acid sequence at least about 90%, 95%, 97%, 98%, 99%, or 100% identical to SEQ ID NO:27.

Embodiment 16. The chimeric antigen receptor of any one of embodiments 1 to 12, wherein said heavy chain variable domain consists of the sequence of SEQ ID NO:27.

Embodiment 17. The chimeric antigen receptor of any one of embodiments 1 to 12, wherein said light chain variable domain comprises an amino acid sequence at least about 90%, 95%, 97%, 98%, 99%, or 100% identical to SEQ ID NO:19.

Embodiment 18. The chimeric antigen receptor of any one of embodiments 1 to 12, wherein said light chain variable domain consists of the sequence of SEQ ID NO:19.

Embodiment 19. The chimeric antigen receptor of any one of embodiments 1 to 12, wherein said light chain variable domain comprises an amino acid sequence at least about 90%, 95%, 97%, 98%, 99%, or 100% identical to SEQ ID NO:20.

Embodiment 20. The chimeric antigen receptor of any one of embodiments 1 to 12, wherein said light chain variable domain consists of the sequence of SEQ ID NO:20.

Embodiment 21. The chimeric antigen receptor of any one of embodiments 1 to 12, wherein said heavy chain variable domain comprises an amino acid sequence at least about 90%, 95%, 97%, 98%, 99%, or 100% identical to SEQ ID NO:25.

Embodiment 22. The chimeric antigen receptor of any one of embodiments 1 to 12, wherein said heavy chain variable domain consists of the sequence of SEQ ID NO:25.

Embodiment 23. The chimeric antigen receptor of any one of embodiments 1 to 12 wherein said heavy chain variable domain comprises an amino acid sequence at least about 90%, 95%, 97%, 98%, 99%, or 100% identical to SEQ ID NO:26.

Embodiment 24. The chimeric antigen receptor of any one of embodiments 1 to 12, wherein said heavy chain variable domain consists of the sequence of SEQ ID NO:26.

Embodiment 25. The chimeric antigen receptor of any one of embodiments 1 to 24, wherein said transmembrane domain comprises a CD8α transmembrane domain, a CD28 transmembrane domain, a CD4 transmembrane domain, a CD3ζ transmembrane domain, or any combination thereof.

Embodiment 26. The chimeric antigen receptor of embodiment 25, wherein said transmembrane domain is a CD28 transmembrane domain.

Embodiment 27. The chimeric antigen receptor of embodiment 25, wherein said CD28 transmembrane domain comprises the sequence of SEQ ID NO:32.

Embodiment 28. The chimeric antigen receptor of embodiment 25, wherein said CD28 transmembrane domain consists of the sequence of SEQ ID NO:32.

Embodiment 29. The chimeric antigen receptor of any one of embodiments 1 to 28, wherein said intracellular domain comprises, one or more intracellular co-stimulatory signaling domains, one or more intracellular T-cell signaling domains, or one or more intracellular co-stimulatory signaling domains and one or more intracellular T-cell signaling domains.

Embodiment 30. The chimeric antigen receptor of embodiment 29, wherein said one or more intracellular co-stimulatory signaling domains are a 4-1BB intracellular co-stimulatory signaling domain, a CD28 intracellular co-stimulatory signaling domain, a ICOS intracellular co-stimulatory signaling domain, an OX-40 intracellular co-stimulatory signaling domain or any combination thereof.

Embodiment 31. The chimeric antigen receptor of embodiment 29, comprising a 4-1BB intracellular co-stimulatory signaling domain.

Embodiment 32. The chimeric antigen receptor of embodiment 31, wherein said 4-1BB intracellular co-stimulatory signaling domain comprises the sequence of SEQ ID NO: 33.

Embodiment 33. The chimeric antigen receptor of embodiment 31, wherein said 4-1BB intracellular co-stimulatory signaling domain consists of the sequence of SEQ ID NO: 33.

Embodiment 34. The chimeric antigen receptor of embodiment 29 comprising a CD28 intracellular co-stimulatory signaling domain and a 4-1BB intracellular co-stimulatory signaling domain.

Embodiment 35. The chimeric antigen receptor of any one of embodiments 1 to 34, further comprising an intracellular T-cell signaling domain.

Embodiment 36. The chimeric antigen receptor of embodiment 35, wherein said intracellular T-cell signaling domain is a CD3ζ intracellular T-cell signaling domain.

Embodiment 37. The chimeric antigen receptor of embodiment 36, wherein said CD3ζ intracellular T-cell signaling domain comprises the sequence of SEQ ID NO:34.

Embodiment 38. The chimeric antigen receptor of embodiment 36, wherein said CD3ζ intracellular T-cell signaling domain consists of the sequence of SEQ ID NO:34.

Embodiment 39. The chimeric antigen receptor of any one of embodiments 1 to 38, wherein said chimeric antigen receptor binds to a cell expressing ROR-1.

Embodiment 40. A nucleic acid encoding the chimeric antigen receptor of any one of embodiments 1 to 39.

Embodiment 41. The nucleic acid of embodiment 40, wherein the nucleic acid is a viral vector, Embodiment 42. The nucleic acid of embodiment 41, wherein the nucleic acid vector is a lentiviral vector.

Embodiment 43. A cell comprising the nucleic acid of any one of embodiments 40 to 42.

Embodiment 44. A cell expressing the chimeric antigen receptor of any one of embodiments 1 to 39.

Embodiment 45. The cell of embodiment 43 or 44, wherein the cell is a T lymphocyte.

Embodiment 46. The cell of embodiment 45, wherein said T lymphocyte is a CD8 positive T lymphocyte.

Embodiment 47. The cell of embodiment 43 or 44, wherein the cell is a natural killer cell.

Embodiment 48. A pharmaceutical composition comprising a therapeutically effective amount of a population of cells of any one of embodiments 43 to 47 and a pharmaceutically acceptable diluent, carrier, or excipient.

Embodiment 49. The pharmaceutical composition of embodiment 48, formulated for intravenous injection.

Embodiment 50. A method of treating cancer in an individual in need thereof, said method comprising administering to said individual the pharmaceutical composition of embodiment 48 or 49.

Embodiment 51. The method of embodiment 50, wherein the cancer comprises a leukemia, a lymphoma, chronic lymphocytic leukemia (CLL), adult acute myeloid leukemia (AML), acute lymphoblastic leukemia (ALL), ovarian cancer, colon cancer, lung cancer, skin cancer, pancreatic cancer, testicular cancer, bladder cancer, uterine cancer, prostate cancer, or adrenal cancer.

Embodiment 52. The method of embodiment 50 or 51, wherein the method further comprises administering cirmtuzumab to the individual.

Embodiment 53. The method of embodiment 52, wherein said cirmtuzumab and said pharmaceutical composition of embodiment 48 or 49 are administered separately.

Embodiment 54. The pharmaceutical composition of embodiment 48 or 49 for use in a method of treating cancer in an individual.

Embodiment 55. The pharmaceutical composition for the use of embodiment 54, wherein the cancer comprises a leukemia, a lymphoma, chronic lymphocytic leukemia (CLL), adult acute myeloid leukemia (AML), acute lymphoblastic leukemia (ALL), ovarian cancer, colon cancer, lung cancer, skin cancer, pancreatic cancer, testicular cancer, bladder cancer, uterine cancer, prostate cancer, or adrenal cancer.

Embodiment 56. A chimeric antigen receptor comprising:

an antigen binding region, wherein said antigen binding region specifically binds ROR-1 wherein said antigen binding region comprises a light chain variable domain and a heavy chain variable domain;

wherein said light chain variable domain comprises a CDR L1 as set forth in SEQ ID NO:43, a CDR L2 as set forth in SEQ ID NO:44 and a CDR L3 as set forth in SEQ ID NO:45; and said heavy chain variable domain comprises a CDR H1 as set forth in SEQ ID NO:46, a CDR H2 as set forth in SEQ ID NO:47, and a CDR H3 as set forth in SEQ ID NO:48; or wherein said light chain variable domain comprises a CDR L1 as set forth in SEQ ID NO:49, a CDR L2 as set forth in SEQ ID NO:50 and a CDR L3 as set forth in SEQ ID NO:51; and said heavy chain variable domain comprising a CDR H1 as set forth in SEQ ID NO:52, a CDR H2 as set forth in SEQ ID NO:53, and a CDR H3 as set forth in SEQ ID NO:54;

a transmembrane domain; and an intracellular domain, wherein said intracellular domain comprises an intracellular T cell signaling domain and an intracellular co-stimulatory domain selected from, 4-1BB, ICOS, OX-40, and combinations thereof.

Embodiment 57. The chimeric antigen receptor of embodiment 56, comprising a spacer a spacer domain, wherein said spacer domain comprises a spacer of between 10 and 200 amino acids in length Embodiment 58. The chimeric antigen receptor of embodiment 57, wherein the spacer is between 14 and 120 amino acids in length.

Embodiment 59. The chimeric antigen receptor of any one of embodiments 56 or 58, wherein said light chain variable domain is N-terminal of said heavy chain variable domain.

Embodiment 60. The chimeric antigen receptor of embodiment 59, wherein said light chain variable domain is covalently coupled to said heavy chain variable domain through a polypeptide linker.

Embodiment 61. The chimeric antigen receptor of embodiment 60, wherein said polypeptide linker consists of the sequence of SEQ ID NO:24.

Embodiment 62. The chimeric antigen receptor of any one of embodiments 56 to 61, wherein said spacer domain comprises an antibody domain.

Embodiment 63. The chimeric antigen receptor of embodiment 62, wherein said antibody domain comprises an immunoglobulin hinge domain, an immunoglobulin constant heavy chain 3 (CH3) domain, an immunoglobulin constant heavy chain 2 (CH2) domain, or any combination thereof.

Embodiment 64. The chimeric antigen receptor of embodiment 63, wherein said antibody domain consists of said immunoglobulin hinge domain.

Embodiment 65. The chimeric antigen receptor of embodiment 63, wherein said antibody domain consists of an immunoglobulin hinge domain and said immunoglobulin constant heavy chain 3 (CH3) domain.

Embodiment 66. The chimeric antigen receptor of embodiment 63, wherein said antibody domain consists of said immunoglobulin hinge domain, said immunoglobulin constant heavy chain 3 (CH3) domain and said immunoglobulin constant heavy chain 2 (CH2) domain.

Embodiment 67. The chimeric antigen receptor of embodiment 63, wherein said spacer domain comprises the sequence of SEQ ID NO:29, SEQ ID NO:41 or SEQ ID NO:42.

Embodiment 68. The chimeric antigen receptor of embodiment 63, wherein said spacer domain consists of the sequence of SEQ ID NO:29, SEQ ID NO:41 or SEQ ID NO:42.

Embodiment 69. The chimeric antigen receptor of any one of embodiments 56 to 68, wherein said light chain variable domain comprises an amino acid sequence at least about 90%, 95%, 97%, 98%, 99%, or 100% identical to SEQ ID NO:21.

Embodiment 70. The chimeric antigen receptor of any one of embodiments 56 to 68, wherein said light chain variable domain consists of the sequence of SEQ ID NO:21.

Embodiment 71. The chimeric antigen receptor of any one of embodiments 56 to 68, wherein said heavy chain variable domain comprises an amino acid sequence at least about 90%, 95%, 97%, 98%, 99%, or 100% identical to SEQ ID NO:27.

Embodiment 72. The chimeric antigen receptor of any one of embodiments 56 to 68, wherein said heavy chain variable domain consists of the sequence of SEQ ID NO:27.

Embodiment 73. The chimeric antigen receptor of any one of embodiments 56 to 68, wherein said light chain variable domain comprises an amino acid sequence at least about 90%, 95%, 97%, 98%, 99%, or 100% identical to SEQ ID NO:19.

Embodiment 74. The chimeric antigen receptor of any one of embodiments 56 to 68, wherein said light chain variable domain consists of the sequence of SEQ ID NO:19.

Embodiment 75. The chimeric antigen receptor of any one of embodiments 56 to 68, wherein said light chain variable domain comprises an amino acid sequence at least about 90%, 95%, 97%, 98%, 99%, or 100% identical to SEQ ID NO:20.

Embodiment 76. The chimeric antigen receptor of any one of embodiments 56 to 68, wherein said light chain variable domain consists of the sequence of SEQ ID NO:20.

Embodiment 77. The chimeric antigen receptor of any one of embodiments 56 to 68, wherein said heavy chain variable domain comprises an amino acid sequence at least about 90%, 95%, 97%, 98%, 99%, or 100% identical to SEQ ID NO:25.

Embodiment 78. The chimeric antigen receptor of any one of embodiments 56 to 68, wherein said heavy chain variable domain consists of the sequence of SEQ ID NO:25.

Embodiment 79. The chimeric antigen receptor of any one of embodiments 56 to 68 wherein said heavy chain variable domain comprises an amino acid sequence at least about 90%, 95%, 97%, 98%, 99%, or 100% identical to SEQ ID NO:26.

Embodiment 80. The chimeric antigen receptor of any one of embodiments 56 to 68, wherein said heavy chain variable domain consists of the sequence of SEQ ID NO:26.

Embodiment 81. The chimeric antigen receptor of any one of embodiments 56 to 80, wherein said transmembrane domain comprises a CD8α transmembrane domain, a CD28 transmembrane domain, a CD4 transmembrane domain, a CD3ζ transmembrane domain, or any combination thereof.

Embodiment 82. The chimeric antigen receptor of embodiment 81, wherein said transmembrane domain is a CD28 transmembrane domain.

Embodiment 83. The chimeric antigen receptor of embodiment 82, wherein said CD28 transmembrane domain comprises the sequence of SEQ ID NO:32.

Embodiment 84. The chimeric antigen receptor of embodiment 82, wherein said CD28 transmembrane domain consists of the sequence of SEQ ID NO:32.

Embodiment 85. The chimeric antigen receptor of any one of embodiments 56 to 84, wherein said intracellular domain comprises 4-1BB intracellular co-stimulatory signaling domain.

Embodiment 86. The chimeric antigen receptor of embodiment 85, wherein said 4-1BB intracellular co-stimulatory signaling domain comprises the sequence of SEQ ID NO: 33.

Embodiment 87. The chimeric antigen receptor of embodiment 85, wherein said 4-1BB intracellular co-stimulatory signaling domain consists of the sequence of SEQ ID NO: 33.

Embodiment 88. The chimeric antigen receptor of any one of embodiments 56 to 87, comprising a CD28 intracellular co-stimulatory signaling domain and a 4-1BB intracellular co-stimulatory signaling domain.

Embodiment 89. The chimeric antigen receptor of any one of embodiments 56 to 88, wherein said intracellular T-cell signaling domain is a CD3ζ intracellular T-cell signaling domain.

Embodiment 90. The chimeric antigen receptor of embodiment 89, wherein said CD3ζ intracellular T-cell signaling domain comprises the sequence of SEQ ID NO:34.

Embodiment 91. The chimeric antigen receptor of embodiment 89, wherein said CD3 intracellular T-cell signaling domain consists of the sequence of SEQ ID NO:34.

Embodiment 92. The chimeric antigen receptor of any one of embodiments 56 to 91 wherein said chimeric antigen receptor binds to a cell expressing ROR-1.

Embodiment 93. A nucleic acid encoding the chimeric antigen receptor of any one of embodiments 56 to 92.

Embodiment 94. The nucleic acid of embodiment 93, wherein the nucleic acid is a viral vector.

Embodiment 95. The nucleic acid of embodiment 94, wherein the viral vector is a lentiviral vector.

Embodiment 96. A cell comprising the nucleic acid of any one of embodiments 93 to 95.

Embodiment 97. A cell expressing the chimeric antigen receptor of any one of embodiments 56 to 92.

Embodiment 98. The cell of embodiment 96 or 97, wherein the cell is a T lymphocyte.

Embodiment 99. The cell of embodiment 98, wherein said T lymphocyte is a CD8 positive T lymphocyte.

Embodiment 100. The cell of embodiment 96 or 97, wherein the cell is a natural killer cell.

Embodiment 101. A pharmaceutical composition comprising a therapeutically effective amount of a population of cells of any one of embodiments 96 to 100, and a pharmaceutically acceptable diluent, carrier, or excipient.

Embodiment 102. The pharmaceutical composition of embodiment 101, formulated for intravenous injection.

Embodiment 103. A method of treating cancer in an individual in need thereof, said method comprising administering to said individual the pharmaceutical composition of embodiment Embodiment 104. The method of embodiment 103, wherein the cancer comprises a leukemia, a lymphoma, chronic lymphocytic leukemia (CLL), adult acute myeloid leukemia (AML), acute lymphoblastic leukemia (ALL), ovarian cancer, colon cancer, lung cancer, skin cancer, pancreatic cancer, testicular cancer, bladder cancer, uterine cancer, prostate cancer, or adrenal cancer.

Embodiment 105. The method of embodiment 103 or 104, wherein the method further comprises administering cirmtuzumab to the individual.

Embodiment 106. The method of embodiment 105, wherein said cirmtuzumab and said pharmaceutical composition of embodiment 101 or 102 are administered separately.

Embodiment 107. The pharmaceutical composition of embodiment 101 or 102 for use in a method of treating cancer in an individual.

Embodiment 108. The pharmaceutical composition for the use of embodiment 107, wherein the cancer comprises a leukemia, a lymphoma, chronic lymphocytic leukemia (CLL), adult acute myeloid leukemia (AML), acute lymphoblastic leukemia (ALL), ovarian cancer, colon cancer, lung cancer, skin cancer, pancreatic cancer, testicular cancer, bladder cancer, uterine cancer, prostate cancer, or adrenal cancer.

What is claimed is:

1. A chimeric antigen receptor comprising:

i. an antigen binding region, wherein the antigen binding region specifically binds ROR-1 and wherein the antigen binding region comprises a light chain variable domain and a heavy chain variable domain;

(a) wherein the light chain variable domain comprises a CDR L1 as set forth in SEQ ID NO:43, a CDR L2 as set forth in SEQ ID NO:44 and a CDR L3 as set forth in SEQ ID NO:45; and the heavy chain variable domain comprises a CDR H1 as set forth in SEQ ID NO:46, a CDR H2 as set forth in SEQ ID NO:47, and a CDR H3 as set forth in SEQ ID NO:48; or (b) wherein the light chain variable domain comprises a CDR L1 as set forth in SEQ ID NO:49, a CDR L2 as set forth in SEQ ID NO:50 and a CDR L3 as set forth in SEQ ID NO:51; and the heavy chain variable domain comprising a CDR H1 as set forth in SEQ ID NO:52, a CDR H2 as set forth in SEQ ID NO:53, and a CDR H3 as set forth in SEQ ID NO: 54;

ii. a spacer domain, wherein the spacer domain comprises an amino acid sequence of SEQ ID NO:29 or SEQ ID NO: 41;

iii. a transmembrane domain; and iv. an intracellular domain wherein the chimeric antigen receptor binds to a cell expressing ROR-1.

2. The chimeric antigen receptor of claim 1, wherein the spacer domain comprises an antibody domain.

3. The chimeric antigen receptor of claim 2, wherein the antibody domain comprises an immunoglobulin hinge domain, an immunoglobulin constant heavy chain 3 (CH3) domain, an immunoglobulin constant heavy chain 2 (CH2) domain, or a combination thereof.

4. The chimeric antigen receptor of claim 3, wherein the light chain variable domain comprises an amino acid sequence at least about 90%, 95%, 97%, 98%, 99%, or 100% identical to SEQ ID NO:21.

5. The chimeric antigen receptor of claim 3, wherein the heavy chain variable domain comprises an amino acid sequence at least about 90%, 95%, 97%, 98%, 99%, or 100% identical to SEQ ID NO:27.

6. The chimeric antigen receptor of claim 1, wherein the transmembrane domain comprises a CD8α transmembrane domain, a CD28 transmembrane domain, a CD4 transmembrane domain, a CD3ζ transmembrane domain, an amino acid sequence of SEQ ID NO:32, or any combination thereof.

7. The chimeric antigen receptor of claim 1, wherein the intracellular domain comprises an intracellular co-stimulatory signaling domain, an intracellular T-cell signaling domain, or a combination thereof.

8. The chimeric antigen receptor of claim 7, wherein the intracellular co-stimulatory signaling domain is a 4-1BB intracellular co-stimulatory signaling domain, a CD28 intracellular co-stimulatory signaling domain, a ICOS intracellular co-stimulatory signaling domain, an OX-40 intracellular co-stimulatory signaling domain, an amino acid sequence of SEQ ID NO:33, a CD28 intracellular co-stimulatory signaling domain and a 4-IBB intracellular co-stimulatory signaling domain, or any combination thereof.

9. The chimeric antigen receptor of claim 7, wherein the intracellular costimulatory signaling domain further comprises an intracellular T-cell signaling domain, an intracellular T-cell signaling domain wherein the intracellular T-cell signaling domain is a CD3ζ.

10. A nucleic acid encoding the chimeric antigen receptor of claim 1.

11. The nucleic acid of claim 10, wherein the nucleic acid is a viral vector.

12. The nucleic acid of claim 11, wherein the viral vector is a lentiviral vector.

13. A cell expressing the chimeric antigen receptor of claim 1.

14. The cell of claim 13, wherein the cell is a T lymphocyte.

15. The cell of claim 14, wherein the T lymphocyte is a CD4+ T lymphocyte or a CD8+ T lymphocyte.

16. The cell of claim 13, wherein the cell is a natural killer cell.

17. A pharmaceutical composition comprising a therapeutically effective amount of the cell of claim 13 and a pharmaceutically acceptable diluent, carrier, or excipient.

18. A method of treating cancer in an individual in need thereof, the method comprising administering to the individual the cell of claim 13.

19. The method of claim 18, wherein the cancer comprises a leukemia, a lymphoma, chronic lymphocytic leukemia, adult acute myeloid leukemia, acute lymphoblastic leukemia, a mantle cell lymphoma, ovarian cancer, colon cancer, lung cancer, skin cancer, pancreatic cancer, testicular cancer, bladder cancer, uterine cancer, prostate cancer, or adrenal cancer.

20. The method of claim 18, wherein the cancer is a CD19-negative cancer or has reduced CD19 expression as a result of a prior treatment that targets CD19.

21. The method of claim 18, wherein the individual has previously been treated with a therapeutic that targets CD19.

* * * * *

SEQUENCE LISTING

```
<160> NUMBER OF SEQ ID NOS: 57

<210> SEQ ID NO 1
<211> LENGTH: 57
<212> TYPE: DNA
<213> ORGANISM: Artificial Sequence
<220> FEATURE:
<223> OTHER INFORMATION: Synthetic construct

<400> SEQUENCE: 1

atgggatggt catgtatcat cctttttcta gtagcaactg caaccggtgt acattcc        57


<210> SEQ ID NO 2
<211> LENGTH: 321
<212> TYPE: DNA
<213> ORGANISM: Artificial Sequence
<220> FEATURE:
<223> OTHER INFORMATION: Synthetic construct

<400> SEQUENCE: 2

gacatcaaga tgacccagtc tccatcttcc atgtatgcat ctctaggaga gagagtcact      60

atcacttgca aggcgagtcc ggacattaat agctatttaa gctggttcca gcagaaacca     120

gggaaatctc ctaagaccct gatctatcgt gcaaacagat tggttgatgg ggtcccatca     180

aggttcagtg gcggtggatc tgggcaagat tattctctca ccatcaacag cctggagtat     240

gaagatatgg gaatttatta ttgtctacag tatgatgaat ttccgtacac gttcggaggg     300

gggaccaagc tggaaatgaa a                                               321


<210> SEQ ID NO 3
```

<211> LENGTH: 321
<212> TYPE: DNA
<213> ORGANISM: Artificial Sequence
<220> FEATURE:
<223> OTHER INFORMATION: Synthetic construct

<400> SEQUENCE: 3
gacatccaga tgacccagtc tccatcctcc ctgtctgcat ctgtaggaga cagagtcacc 60
atcacttgca aggcgagtcc ggacattaat agctatttaa gctggtttca gcagaggcca 120
ggccaatctc caaggcgcct aatttatcgt gcaaacagat tggttgatgg ggtcccagac 180
aggttcagtg gcagtgggtc aggcactgat ttcacactga aaatcagcag ggtggaggct 240
gaggatgttg gagtttatta ctgtctacag tatgatgaat ttccgtacac gttcggccaa 300
gggaccaagg tggaaatcaa a 321

<210> SEQ ID NO 4
<211> LENGTH: 321
<212> TYPE: DNA
<213> ORGANISM: Artificial Sequence
<220> FEATURE:
<223> OTHER INFORMATION: Synthetic construct

<400> SEQUENCE: 4
gatattgtga tgacccagac tccactctcc ctgcccgtca cccctggaga gccggcctcc 60
atctcctgca gggcaagtaa gagcattagc aaatatttag cctggtacca gcagaaacct 120
ggccaggctc ccaggctcct catctattct ggatccactt tgcaatctgg gatcccacct 180
cgattcagtg gcagcgggta tggaacagat tttaccctca caattaataa catagaatct 240
gaggatgctg catattactt ctgtcaacag catgatgaat ccccgtacac gttcggcgag 300
gggaccaagg tggaaatcaa a 321

<210> SEQ ID NO 5
<211> LENGTH: 54
<212> TYPE: DNA
<213> ORGANISM: Artificial Sequence
<220> FEATURE:
<223> OTHER INFORMATION: Synthetic construct

<400> SEQUENCE: 5
ggctccacct ctggatccgg caagcccgga tctggcgagg gatccaccaa gggc 54

<210> SEQ ID NO 6
<211> LENGTH: 54
<212> TYPE: DNA
<213> ORGANISM: Artificial Sequence
<220> FEATURE:
<223> OTHER INFORMATION: Synthetic construct

<400> SEQUENCE: 6
ggctccacct ctggatccgg caagcccgga tctggcgagg gatccaccaa gggc 54

<210> SEQ ID NO 7
<211> LENGTH: 84
<212> TYPE: DNA
<213> ORGANISM: Artificial Sequence
<220> FEATURE:
<223> OTHER INFORMATION: Synthetic construct

<400> SEQUENCE: 7
ggtggtggtg gtagcggctc cacctctgga tccggcaagc ccggatctgg cgagggatcc 60
accaagggcg gaggaggagg aagt 84

<210> SEQ ID NO 8
<211> LENGTH: 357
<212> TYPE: DNA
<213> ORGANISM: Artificial Sequence
<220> FEATURE:
<223> OTHER INFORMATION: Synthetic construct

<400> SEQUENCE: 8
gaagtgaaac tagtggagtc tgggggaggc ttagtgaagc ctggagggtc cctgaaactc 60
tcctgtgcag cctctggatt cactttcagt agctatgcca tgtcttgggt tcgccagatt 120
ccagagaaga ggctggagtg ggtcgcatcc attagtcgtg gtggtaccac ctactatcca 180
gacagtgtga agggccgatt caccatctcc agagataatg tcaggaacat cctgtacctg 240
caaatgagca gtctgaggtc tgaggacacg gccatgtatt actgtggaag atatgattac 300
gacgggtact atgcaatgga ctactggggt caaggaacct cagtcaccgt ctcctca 357

<210> SEQ ID NO 9
<211> LENGTH: 357
<212> TYPE: DNA
<213> ORGANISM: Artificial Sequence
<220> FEATURE:
<223> OTHER INFORMATION: Synthetic construct

<400> SEQUENCE: 9
gaagtgcagc tggtgcagtc tggagcagag gtgaaaaagc ccggggagtc tctgaggatc 60
tcctgtaagg gttctggatt cactttcagt agctatgcca tgtcttggat caggcagtcc 120
ccatcgagag gccttgagtg gctgggttcc attagtcgtg gtggtaccac ctactatcca 180
gacagtgtga agggcagatt caccatctcc agagacaacg ccaagaactc actgtatctg 240
caaatgaaca gcctgagagc cgaggacacg gctgtgtatt actgtggaag atatgattac 300
gacgggtact atgcaatgga ctactggggc cagggaacgc tggtcaccgt cagctca 357

<210> SEQ ID NO 10
<211> LENGTH: 348
<212> TYPE: DNA
<213> ORGANISM: Artificial Sequence
<220> FEATURE:
<223> OTHER INFORMATION: Synthetic construct

<400> SEQUENCE: 10
caggtgcagc tgcaggagtc gggcccagga ctggtgaagc cttcacagac cctgtccctc 60
acctgcactg tctctggtta tgcattcact gcctacaaca tacactgggt gcgacaggcc 120
cctggacaag ggcttgagtg gatgggttct tttgatcctt acgatggtgg tagtagttac 180
aaccagaagt tcaaggacag actcaccatc tccaaggaca cctccaaaaa ccaggtggtc 240
cttacaatga ccaacatgga ccctgtggac acagccacgt attactgtgc aagagggtgg 300
tactactttg actactgggg ccacggaacc ctggtcaccg tctcctca 348

<210> SEQ ID NO 11
<211> LENGTH: 42
<212> TYPE: DNA
<213> ORGANISM: Artificial Sequence
<220> FEATURE:
<223> OTHER INFORMATION: Synthetic construct

<400> SEQUENCE: 11
gtcgacgagt ccaaatatgg tcccccatgc ccaccatgcc ca 42

<210> SEQ ID NO 12
<211> LENGTH: 399
<212> TYPE: DNA
<213> ORGANISM: Artificial Sequence
<220> FEATURE:
<223> OTHER INFORMATION: Synthetic construct

<400> SEQUENCE: 12
ggcaaggagt acaagtgcaa ggtctccaac aaaggcctcc cgtcctccat cgagaaaacc 60
atctccaaag ccaaagggca gccccgagag ccacaggtgt acaccctgcc cccatcccag 120
gaggagatga ccaagaacca ggtcagcctg acctgcctgg tcaaaggctt ctaccccagc 180
gacatcgccg tggagtggga gagcaatggg cagccggaga acaactacaa gaccacgcct 240
cccgtgctgg actccgacgg ctccttcttc ctctacagca ggctaaccgt ggacaagagc 300
aggtggcagg aggggaatgt cttctcatgc tccgtgatgc atgaggctct gcacaaccac 360
tacacacaga agagcctctc cctgtcccta ggtaaaatg 399

<210> SEQ ID NO 13
<211> LENGTH: 654
<212> TYPE: DNA
<213> ORGANISM: Artificial Sequence
<220> FEATURE:
<223> OTHER INFORMATION: Synthetic construct

<400> SEQUENCE: 13
gcacctgagt tcctgggggg accatcagtc ttcctgttcc ccccaaaacc caaggacact 60
ctcatgatct cccggacccc tgaggtcacg tgcgtggtgg tggacgtgag ccaggaagac 120
cccgaggtcc agttcaactg gtacgtggat ggcgtggagg tgcataatgc caagacaaag 180
ccgcgggagg agcagttcaa cagcacgtac cgtgtggtca gcgtcctcac cgtcctgcac 240
caggactggc tgaacggcaa ggagtacaag tgcaaggtct ccaacaaagg cctcccgtcc 300
tccatcgaga aaaccatctc caaagccaaa gggcagcccc gagagccaca ggtgtacacc 360
ctgcccccat cccaggagga gatgaccaag aaccaggtca gcctgacctg cctggtcaaa 420
ggcttctacc ccagcgacat cgccgtggag tgggagagca atgggcagcc ggagaacaac 480
tacaagacca cgcctcccgt gctggactcc gacggctcct tcttcctcta cagcaggcta 540
accgtggaca agagcaggtg gcaggagggg aatgtcttct catgctccgt gatgcatgag 600
gctctgcaca accactacac acagaagagc ctctccctgt ccctaggtaa aatg 654

<210> SEQ ID NO 14
<211> LENGTH: 204
<212> TYPE: DNA
<213> ORGANISM: Artificial Sequence
<220> FEATURE:
<223> OTHER INFORMATION: Synthetic construct

<400> SEQUENCE: 14
ttttgggtgc tggtggtggt tggtggagtc ctggcttgct atagcttgct agtaacagtg 60
gcctttatta ttttctgggt gaggagtaag aggagcaggg gcggacacag tgactacatg 120
aacatgactc cccgccgccc tgggcccacc cgcaagcatt accagcccta tgccccacca 180
cgcgacttcg cagcctatcg ctcc 204

<210> SEQ ID NO 15
<211> LENGTH: 126
<212> TYPE: DNA
<213> ORGANISM: Artificial Sequence
<220> FEATURE:
<223> OTHER INFORMATION: Synthetic construct

<400> SEQUENCE: 15
aaacggggca gaaagaaact cctgtatata ttcaaacaac catttatgag accagtacaa 60
actactcaag aggaagatgg ctgtagctgc cgatttccag aagaagaaga aggaggatgt 120
gaactg 126

<210> SEQ ID NO 16
<211> LENGTH: 339
<212> TYPE: DNA
<213> ORGANISM: Artificial Sequence
<220> FEATURE:
<223> OTHER INFORMATION: Synthetic construct

<400> SEQUENCE: 16
agagtgaagt tcagcaggag cgcagacgcc cccgcgtacc agcagggcca gaaccagctc 60
tataacgagc tcaatctagg acgaagagag gagtacgatg ttttggacaa gagacgtggc 120
cgggaccctg agatgggggg aaagccgaga aggaagaacc ctcaggaagg cctgtacaat 180
gaactgcaga aagataagat ggcggaggcc tacagtgaga ttgggatgaa aggcgagcgc 240
cggaggggca aggggcacga tggcctttac cagggtctca gtacagccac caaggacacc 300
tacgacgccc ttcacatgca ggccctgccc cctcgctga 339

<210> SEQ ID NO 17
<211> LENGTH: 7489
<212> TYPE: DNA
<213> ORGANISM: Artificial Sequence
<220> FEATURE:
<223> OTHER INFORMATION: Synthetic construct

<400> SEQUENCE: 17
gtccgaaatc aacctctgga ttacaaaatt tgtgaaagat tgactggtat tcttaactat 60
gttgctcctt ttacgctatg tggatacgct gctttaatgc ctttgtatca tgctattgct 120
tcccgtatgg ctttcatttt ctcctccttg tataaatcct ggttgctgtc tctttatgag 180
gagttgtggc ccgttgtcag gcaacgtggc gtggtgtgca ctgtgtttgc tgacgcaacc 240
cccactggtt ggggcattgc caccacctgt cagctccttt ccgggacttt cgctttcccc 300
ctccctattg ccacggcgga actcatcgcc gcctgccttg cccgctgctg gacaggggct 360
cggctgttgg gcactgacaa ttccgtggtg ttgtcgggga agctgacgtc ctttccatgg 420
ctgctcgcct gtgttgccac ctggattctg cgcgggacgt ccttctgcta cgtcccttcg 480
gccctcaatc cagcggacct tccttcccgc ggcctgctgc cggctctgcg gcctcttccg 540
cgtcttcgcc ttcgccctca gacgagtcgg atctcccttt gggccgcctc cccgcctgga 600
attcgagctc ggtaccttta agaccaatga cttacaaggc agctgtagat cttagccact 660
ttttaaaaga aaagggggga ctggaagggc taattcactc ccaacgaaga caagatctgc 720
tttttgcttg tactgggtct ctctggttag accagatctg agcctgggag ctctctggct 780
aactagggaa cccactgctt aagcctcaat aaagcttgcc ttgagtgctt caagtagtgt 840
gtgcccgtct gttgtgtgac tctggtaact agagatccct cagacccttt tagtcagtgt 900
ggaaaatctc tagcagtagt agttcatgtc atcttattat tcagtattta taacttgcaa 960
agaaatgaat atcagagagt gagaggaact tgtttattgc agcttataat ggttacaaat 1020
aaagcaatag catcacaaat ttcacaaata aagcattttt ttcactgcat tctagttgtg 1080

```
gtttgtccaa actcatcaat gtatcttatc atgtctggct ctagctatcc cgcccctaac   1140
tccgcccatc ccgcccctaa ctccgcccag ttccgcccat tctccgcccc atggctgact   1200
aatttttttt atttatgcag aggccgaggc cgcctcggcc tctgagctat tccagaagta   1260
gtgaggaggc ttttttggag gcctagggac gtacccaatt cgccctatag tgagtcgtat   1320
tacgcgcgct cactggccgt cgttttacaa cgtcgtgact gggaaaaccc tggcgttacc   1380
caacttaatc gccttgcagc acatccccct ttcgccagct ggcgtaatag cgaagaggcc   1440
cgcaccgatc gcccttccca acagttgcgc agcctgaatg gcgaatggga cgcgccctgt   1500
agcggcgcat taagcgcggc gggtgtggtg gttacgcgca gcgtgaccgc tacacttgcc   1560
agcgccctag cgcccgctcc tttcgctttc ttcccttcct ttctcgccac gttcgccggc   1620
tttccccgtc aagctctaaa tcgggggctc cctttagggt tccgatttag tgctttacgg   1680
cacctcgacc ccaaaaaact tgattagggt gatggttcac gtagtgggcc atcgccctga   1740
tagacggttt ttcgcccttt gacgttggag tccacgttct ttaatagtgg actcttgttc   1800
caaactggaa caacactcaa ccctatctcg gtctattctt ttgatttata agggattttg   1860
ccgatttcgg cctattggtt aaaaaatgag ctgatttaac aaaaatttaa cgcgaatttt   1920
aacaaaatat taacgcttac aatttaggtg gcacttttcg gggaaatgtg cgcggaaccc   1980
ctatttgttt atttttctaa atacattcaa atatgtatcc gctcatgaga caataaccct   2040
gataaatgct tcaataatat tgaaaaagga agagtatgag tattcaacat ttccgtgtcg   2100
cccttattcc cttttttgcg gcattttgcc ttcctgtttt tgctcaccca gaaacgctgg   2160
tgaaagtaaa agatgctgaa gatcagttgg gtgcacgagt gggttacatc gaactggatc   2220
tcaacagcgg taagatcctt gagagttttc gccccgaaga acgttttcca atgatgagca   2280
cttttaaagt tctgctatgt ggcgcggtat tatcccgtat tgacgccggg caagagcaac   2340
tcggtcgccg catacactat tctcagaatg acttggttga gtactcacca gtcacagaaa   2400
agcatcttac ggatggcatg acagtaagag aattatgcag tgctgccata accatgagtg   2460
ataacactgc ggccaactta cttctgacaa cgatcggagg accgaaggag ctaaccgctt   2520
ttttgcacaa catgggggat catgtaactc gccttgatcg ttgggaaccg gagctgaatg   2580
aagccatacc aaacgacgag cgtgacacca cgatgcctgt agcaatggca acaacgttgc   2640
gcaaactatt aactggcgaa ctacttactc tagcttcccg gcaacaatta atagactgga   2700
tggaggcgga taaagttgca ggaccacttc tgcgctcggc ccttccggct ggctggttta   2760
ttgctgataa atctggagcc ggtgagcgtg ggtctcgcgg tatcattgca gcactggggc   2820
cagatggtaa gccctcccgt atcgtagtta tctacacgac ggggagtcag gcaactatgg   2880
atgaacgaaa tagacagatc gctgagatag gtgcctcact gattaagcat tggtaactgt   2940
cagaccaagt ttactcatat atactttaga ttgatttaaa acttcatttt taatttaaaa   3000
ggatctaggt gaagatcctt tttgataatc tcatgaccaa aatcccttaa cgtgagtttt   3060
cgttccactg agcgtcagac cccgtagaaa agatcaaagg atcttcttga gatccttttt   3120
ttctgcgcgt aatctgctgc ttgcaaacaa aaaaaccacc gctaccagcg gtggtttgtt   3180
tgccggatca agagctacca actctttttc cgaaggtaac tggcttcagc agagcgcaga   3240
taccaaatac tgttcttcta gtgtagccgt agttaggcca ccacttcaag aactctgtag   3300
caccgcctac atacctcgct ctgctaatcc tgttaccagt ggctgctgcc agtggcgata   3360
agtcgtgtct taccgggttg gactcaagac gatagttacc ggataaggcg cagcggtcgg   3420
gctgaacggg gggttcgtgc acacagccca gcttggagcg aacgacctac accgaactga   3480
```

gatacctaca gcgtgagcta tgagaaagcg ccacgcttcc cgaagggaga aaggcggaca 3540
ggtatccggt aagcggcagg gtcggaacag gagagcgcac gagggagctt ccagggggaa 3600
acgcctggta tctttatagt cctgtcgggt ttcgccacct ctgacttgag cgtcgatttt 3660
tgtgatgctc gtcagggggg cggagcctat ggaaaaacgc cagcaacgcg gcctttttac 3720
ggttcctggc cttttgctgg ccttttgctc acatgttctt tcctgcgtta tcccctgatt 3780
ctgtggataa ccgtattacc gcctttgagt gagctgatac cgctcgccgc agccgaacga 3840
ccgagcgcag cgagtcagtg agcgaggaag cggaagagcg cccaatacgc aaaccgcctc 3900
tccccgcgcg ttggccgatt cattaatgca gctggcacga caggtttccc gactggaaag 3960
cgggcagtga gcgcaacgca attaatgtga gttagctcac tcattaggca ccccaggctt 4020
tacactttat gcttccggct cgtatgttgt gtggaattgt gagcggataa caatttcaca 4080
caggaaacag ctatgaccat gattacgcca agcgcgcaat taaccctcac taaagggaac 4140
aaaagctgga gctgcaagct taatgtagtc ttatgcaata ctcttgtagt cttgcaacat 4200
ggtaacgatg agttagcaac atgccttaca aggagagaaa aagcaccgtg catgccgatt 4260
ggtggaagta aggtggtacg atcgtgcctt attaggaagg caacagacgg gtctgacatg 4320
gattggacga accactgaat tgccgcattg cagagatatt gtatttaagt gcctagctcg 4380
atacataaac gggtctctct ggttagacca gatctgagcc tgggagctct ctggctaact 4440
agggaaccca ctgcttaagc ctcaataaag cttgccttga gtgcttcaag tagtgtgtgc 4500
ccgtctgttg tgtgactctg gtaactagag atccctcaga cccttttagt cagtgtggaa 4560
aatctctagc agtggcgccc gaacagggac ttgaaagcga aagggaaacc agaggagctc 4620
tctcgacgca ggactcggct tgctgaagcg cgcacggcaa gaggcgaggg gcggcgactg 4680
gtgagtacgc caaaaatttt gactagcgga ggctagaagg agagagatgg gtgcgagagc 4740
gtcagtatta agcgggggag aattagatcg cgatgggaaa aaattcggtt aaggccaggg 4800
ggaaagaaaa aatataaatt aaaacatata gtatgggcaa gcagggagct agaacgattc 4860
gcagttaatc ctggcctgtt agaaacatca gaaggctgta gacaaatact gggacagcta 4920
caaccatccc ttcagacagg atcagaagaa cttagatcat tatataatac agtagcaacc 4980
ctctattgtg tgcatcaaag gatagagata aaagacacca aggaagcttt agacaagata 5040
gaggaagagc aaaacaaaag taagaccacc gcacagcaag cggccgctga tcttcagacc 5100
tggaggagga gatatgaggg acaattggag aagtgaatta tataaatata aagtagtaaa 5160
aattgaacca ttaggagtag cacccaccaa ggcaaagaga agagtggtgc agagagaaaa 5220
aagagcagtg ggaataggag ctttgttcct tgggttcttg ggagcagcag gaagcactat 5280
gggcgcagcg tcaatgacgc tgacggtaca ggccagacaa ttattgtctg gtatagtgca 5340
gcagcagaac aatttgctga gggctattga ggcgcaacag catctgttgc aactcacagt 5400
ctggggcatc aagcagctcc aggcaagaat cctggctgtg gaaagatacc taaaggatca 5460
acagctcctg gggatttggg gttgctctgg aaaactcatt tgcaccactg ctgtgccttg 5520
gaatgctagt tggagtaata aatctctgga acagatttgg aatcacacga cctggatgga 5580
gtgggacaga gaaattaaca attacacaag cttaatacac tccttaattg aagaatcgca 5640
aaaccagcaa gaaaagaatg aacaagaatt attggaatta gataaatggg caagtttgtg 5700
gaattggttt aacataacaa attggctgtg gtatataaaa ttattcataa tgatagtagg 5760
aggcttggta ggtttaagaa tagtttttgc tgtactttct atagtgaata gagttaggca 5820
gggatattca ccattatcgt ttcagaccca cctcccaacc ccgaggggac ccgacaggcc 5880
cgaaggaata gaagaagaag gtggagagag agacagagac agatccattc gattagtgaa 5940
cggatctcga cggtatcggt taacttttaa aagaaaaggg gggattgggg ggtacagtgc 6000
aggggaaaga atagtagaca taatagcaac agacatacaa actaaagaat tacaaaaaca 6060
aattacaaaa ttcaaaattt tatcgatgcc tccccgtcac cacccccccc aacccgcccc 6120
gaccggagct gagagtaatt catacaaaag gactcgcccc tgccttgggg aatcccaggg 6180
accgtcgtta aactcccact aacgtagaac ccagagatcg ctgcgttccc gccccctcac 6240
ccgcccgctc tcgtcatcac tgaggtggag aagagcatgc gtgaggctcc ggtgcccgtc 6300
agtgggcaga gcgcacatcg cccacagtcc ccgagaagtt ggggggaggg gtcggcaatt 6360
gaaccggtgc ctagagaagg tggcgcgggg taaactggga aagtgatgtc gtgtactggc 6420
tccgcctttt tcccgagggt gggggagaac cgtatataag tgcagtagtc gccgtgaacg 6480
ttctttttcg caacgggttt gccgccagaa cacaggtaag tgccgtgtgt ggttcccgcg 6540
ggcctggcct ctttacgggt tatggccctt gcgtgccttg aattacttcc acgcccctgg 6600
ctgcagtacg tgattcttga tcccgagctt cgggttggaa gtgggtggga gagttcgagg 6660
ccttgcgctt aaggagcccc ttcgcctcgt gcttgagttg aggcctggcc tgggcgctgg 6720
ggccgccgcg tgcgaatctg gtggcacctt cgcgcctgtc tcgctgcttt cgataagtct 6780
ctagccattt aaaatttttg atgatatcct gcgacgcttt ttttctggca agatagtctt 6840
gtaaatgcgg gccaagatct gcacactggt atttcggttt ttggggccgc gggcggcgac 6900
ggggcccgtg cgtcccagcg cacatgttcg gcgaggcggg gcctgcgagc gcggccaccg 6960
agaatcggac gggggtagtc tcaagctggc cggcctgctc tggtgcctgg cctcgcgccg 7020
ccgtgtatcg ccccgccctg ggcggcaagg ctggcccggt cggcaccagt tgcgtgagcg 7080
gaaagatggc cgcttcccgg ccctgctgca gggagctcaa aatggaggac gcggcgctcg 7140
ggagagcggg cgggtgagtc acccacacaa aggaaaaggg cctttccgtc ctcagccgtc 7200
gcttcatgtg actccacgga gtaccgggcg ccgtccaggc acctcgatta gttctcgagc 7260
ttttggagta cgtcgtcttt aggttggggg gaggggtttt atgcgatgga gtttccccac 7320
actgagtggg tggagactga agttaggcca gcttggcact tgatgtaatt ctccttggaa 7380
tttgcccttt ttgagtttgg atcttggttc attctcaagc ctcagacagt ggttcaaagt 7440 tttttcttc catttcaggt gtcgtgaaaa ctacccctct agagccacc 7489

<210> SEQ ID NO 18
<211> LENGTH: 19
<212> TYPE: PRT
<213> ORGANISM: Artificial Sequence
<220> FEATURE:
<223> OTHER INFORMATION: Synthetic construct

<400> SEQUENCE: 18

Met Gly Trp Ser Cys Ile Ile Leu Phe Leu Val Ala Thr Ala Thr Gly
1 5 10 15

Val His Ser

<210> SEQ ID NO 19
<211> LENGTH: 107
<212> TYPE: PRT
<213> ORGANISM: Artificial Sequence
<220> FEATURE:
<223> OTHER INFORMATION: Synthetic construct

<400> SEQUENCE: 19

```
Asp Ile Lys Met Thr Gln Ser Pro Ser Ser Met Tyr Ala Ser Leu Gly
1               5                   10                  15

Glu Arg Val Thr Ile Thr Cys Lys Ala Ser Pro Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Gly Gly Ser Gly Gln Asp Tyr Ser Leu Thr Ile Asn Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Met Lys
            100                 105
```

<210> SEQ ID NO 20
<211> LENGTH: 107
<212> TYPE: PRT
<213> ORGANISM: Artificial Sequence
<220> FEATURE:
<223> OTHER INFORMATION: Synthetic construct

<400> SEQUENCE: 20

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Pro Asp Ile Asn Ser Tyr
            20                  25                  30

Leu Ser Trp Phe Gln Gln Arg Pro Gly Gln Ser Pro Arg Arg Leu Ile
        35                  40                  45

Tyr Arg Ala Asn Arg Leu Val Asp Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Leu Gln Tyr Asp Glu Phe Pro Tyr
                85                  90                  95

Thr Phe Gly Gln Gly Thr Lys Val Glu Ile Lys
            100                 105
```

<210> SEQ ID NO 21
<211> LENGTH: 107
<212> TYPE: PRT
<213> ORGANISM: Artificial Sequence
<220> FEATURE:
<223> OTHER INFORMATION: Synthetic construct

<400> SEQUENCE: 21

```
Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Ser Ile Ser Lys Tyr
            20                  25                  30

Leu Ala Trp Tyr Gln Gln Lys Pro Gly Gln Ala Pro Arg Leu Leu Ile
        35                  40                  45

Tyr Ser Gly Ser Thr Leu Gln Ser Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80
```

```
Glu Asp Ala Ala Tyr Tyr Phe Cys Gln Gln His Asp Glu Ser Pro Tyr
                85                  90                  95

Thr Phe Gly Glu Gly Thr Lys Val Glu Ile Lys
            100                 105


<210> SEQ ID NO 22
<211> LENGTH: 18
<212> TYPE: PRT
<213> ORGANISM: Artificial Sequence
<220> FEATURE:
<223> OTHER INFORMATION: Synthetic construct

<400> SEQUENCE: 22

Gly Ser Thr Ser Gly Ser Gly Lys Pro Gly Ser Gly Glu Gly Ser Thr
1               5                   10                  15

Lys Gly


<210> SEQ ID NO 23
<211> LENGTH: 18
<212> TYPE: PRT
<213> ORGANISM: Artificial Sequence
<220> FEATURE:
<223> OTHER INFORMATION: Synthetic construct

<400> SEQUENCE: 23

Gly Ser Thr Ser Gly Ser Gly Lys Pro Gly Ser Gly Glu Gly Ser Thr
1               5                   10                  15

Lys Gly


<210> SEQ ID NO 24
<211> LENGTH: 28
<212> TYPE: PRT
<213> ORGANISM: Artificial Sequence
<220> FEATURE:
<223> OTHER INFORMATION: Synthetic construct

<400> SEQUENCE: 24

Gly Gly Gly Gly Ser Gly Ser Thr Ser Gly Ser Gly Lys Pro Gly Ser
1               5                   10                  15

Gly Glu Gly Ser Thr Lys Gly Gly Gly Gly Gly Ser
            20                  25


<210> SEQ ID NO 25
<211> LENGTH: 119
<212> TYPE: PRT
<213> ORGANISM: Artificial Sequence
<220> FEATURE:
<223> OTHER INFORMATION: Synthetic construct

<400> SEQUENCE: 25

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Glu Ser Ser Tyr
            20                  25                  30

Ala Met Ser Trp Val Arg Gln Ile Pro Glu Lys Arg Leu Glu Trp Val
        35                  40                  45

Ala Ser Ile Ser Arg Gly Gly Thr Thr Tyr Tyr Pro Asp Ser Val Lys
    50                  55                  60

Gly Arg Phe Thr Ile Ser Arg Asp Asn Val Arg Asn Ile Leu Tyr Leu
65                  70                  75                  80

Gln Met Ser Ser Leu Arg Ser Glu Asp Thr Ala Met Tyr Tyr Cys Gly
                85                  90                  95
```

```
Arg Tyr Asp Tyr Asp Gly Tyr Tyr Ala Met Asp Tyr Trp Gly Gln Gly
            100                 105                 110

Thr Ser Val Thr Val Ser Ser
        115


<210> SEQ ID NO 26
<211> LENGTH: 119
<212> TYPE: PRT
<213> ORGANISM: Artificial Sequence
<220> FEATURE:
<223> OTHER INFORMATION: Synthetic construct

<400> SEQUENCE: 26

Glu Val Gln Leu Val Gln Ser Gly Ala Glu Val Lys Lys Pro Gly Glu
1               5                   10                  15

Ser Leu Arg Ile Ser Cys Lys Gly Ser Gly Phe Thr Phe Ser Ser Tyr
            20                  25                  30

Ala Met Ser Trp Ile Arg Gln Ser Pro Ser Arg Gly Leu Glu Trp Leu
        35                  40                  45

Gly Ser Ile Ser Arg Gly Gly Thr Thr Tyr Tyr Pro Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115


<210> SEQ ID NO 27
<211> LENGTH: 116
<212> TYPE: PRT
<213> ORGANISM: Artificial Sequence
<220> FEATURE:
<223> OTHER INFORMATION: Synthetic construct

<400> SEQUENCE: 27

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Thr Ala Tyr
            20                  25                  30

Asn Ile His Trp Val Arg Gln Ala Pro Gly Gln Gly Leu Glu Trp Met
        35                  40                  45

Gly Ser Phe Asp Pro Tyr Asp Gly Gly Ser Ser Tyr Asn Gln Lys Phe
    50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Trp Tyr Tyr Phe Asp Tyr Trp Gly His Gly Thr Leu Val
            100                 105                 110

Thr Val Ser Ser
        115


<210> SEQ ID NO 28
<211> LENGTH: 12
<212> TYPE: PRT
```

<213> ORGANISM: Artificial Sequence
<220> FEATURE:
<223> OTHER INFORMATION: Synthetic construct

<400> SEQUENCE: 28

```
Glu Ser Lys Tyr Gly Pro Pro Cys Pro Pro Cys Pro
1               5                   10
```

<210> SEQ ID NO 29
<211> LENGTH: 14
<212> TYPE: PRT
<213> ORGANISM: Artificial Sequence
<220> FEATURE:
<223> OTHER INFORMATION: Synthetic construct

<400> SEQUENCE: 29

```
Val Asp Glu Ser Lys Tyr Gly Pro Pro Cys Pro Pro Cys Pro
1               5                   10
```

<210> SEQ ID NO 30
<211> LENGTH: 14
<212> TYPE: PRT
<213> ORGANISM: Artificial Sequence
<220> FEATURE:
<223> OTHER INFORMATION: Synthetic construct

<400> SEQUENCE: 30

```
Val Asp Glu Ser Lys Tyr Gly Pro Pro Cys Pro Pro Cys Pro
1               5                   10
```

<210> SEQ ID NO 31
<211> LENGTH: 218
<212> TYPE: PRT
<213> ORGANISM: Artificial Sequence
<220> FEATURE:
<223> OTHER INFORMATION: Synthetic construct

<400> SEQUENCE: 31

```
Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
```

```
            180                 185                 190

Phe Ser Cys Ser Val Met His Glu Ala Leu His Asn His Tyr Thr Gln
        195                 200                 205

Lys Ser Leu Ser Leu Ser Leu Gly Lys Met
    210                 215


<210> SEQ ID NO 32
<211> LENGTH: 68
<212> TYPE: PRT
<213> ORGANISM: Artificial Sequence
<220> FEATURE:
<223> OTHER INFORMATION: Synthetic construct

<400> SEQUENCE: 32

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Gly Gly His Ser Asp Tyr Met Asn Met Thr Pro Arg Arg Pro Gly
        35                  40                  45

Pro Thr Arg Lys His Tyr Gln Pro Tyr Ala Pro Pro Arg Asp Phe Ala
    50                  55                  60

Ala Tyr Arg Ser
65


<210> SEQ ID NO 33
<211> LENGTH: 42
<212> TYPE: PRT
<213> ORGANISM: Artificial Sequence
<220> FEATURE:
<223> OTHER INFORMATION: Synthetic construct

<400> SEQUENCE: 33

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 34
<211> LENGTH: 112
<212> TYPE: PRT
<213> ORGANISM: Homo sapiens

<400> SEQUENCE: 34

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
```

100 105 110

<210> SEQ ID NO 35
<211> LENGTH: 2148
<212> TYPE: DNA
<213> ORGANISM: Artificial Sequence
<220> FEATURE:
<223> OTHER INFORMATION: Synthetic construct

<400> SEQUENCE: 35
atgggatggt catgtatcat cctttttcta gtagcaactg caaccggtgt acattccgac 60
atcaagatga cccagtctcc atcttccatg tatgcatctc taggagagag agtcactatc 120
acttgcaagg cgagtccgga cattaatagc tatttaagct ggttccagca gaaaccaggg 180
aaatctccta agaccctgat ctatcgtgca aacagattgg ttgatggggt cccatcaagg 240
ttcagtggcg gtggatctgg gcaagattat tctctcacca tcaacagcct ggagtatgaa 300
gatatgggaa tttattattg tctacagtat gatgaatttc cgtacacgtt cggagggggg 360
accaagctgg aaatgaaagg ctccacctct ggatccggca agcccggatc tggcgaggga 420
tccaccaagg gcgaagtgaa actagtggag tctgggggag gcttagtgaa gcctggaggg 480
tccctgaaac tctcctgtgc agcctctgga ttcactttca gtagctatgc catgtcttgg 540
gttcgccaga ttccagagaa gaggctggag tgggtcgcat ccattagtcg tggtggtacc 600
acctactatc cagacagtgt gaagggccga ttcaccatct ccagagataa tgtcaggaac 660
atcctgtacc tgcaaatgag cagtctgagg tctgaggaca cggccatgta ttactgtgga 720
agatatgatt acgacgggta ctatgcaatg gactactggg gtcaaggaac ctcagtcacc 780
gtctcctcag agtccaaata tggtccccca tgcccaccat gcccagcacc tgagttcctg 840
gggggaccat cagtcttcct gttcccccca aaacccaagg acactctcat gatctcccgg 900
acccctgagg tcacgtgcgt ggtggtggac gtgagccagg aagaccccga ggtccagttc 960
aactggtacg tggatggcgt ggaggtgcat aatgccaaga caaagccgcg ggaggagcag 1020
ttcaacagca cgtaccgtgt ggtcagcgtc ctcaccgtcc tgcaccagga ctggctgaac 1080
ggcaaggagt acaagtgcaa ggtctccaac aaaggcctcc cgtcctccat cgagaaaacc 1140
atctccaaag ccaaagggca gccccgagag ccacaggtgt acaccctgcc cccatcccag 1200
gaggagatga ccaagaacca ggtcagcctg acctgcctgg tcaaaggctt ctaccccagc 1260
gacatcgccg tggagtggga gagcaatggg cagccggaga acaactacaa gaccacgcct 1320
cccgtgctgg actccgacgg ctccttcttc ctctacagca ggctaaccgt ggacaagagc 1380
aggtggcagg aggggaatgt cttctcatgc tccgtgatgc atgaggctct gcacaaccac 1440
tacacacaga agagcctctc cctgtcccta ggtaaaatgt tttgggtgct ggtggtggtt 1500
ggtggagtcc tggcttgcta tagcttgcta gtaacagtgg cctttattat tttctgggtg 1560
aggagtaaga ggagcagggg cggacacagt gactacatga acatgactcc ccgccgccct 1620
gggcccaccc gcaagcatta ccagccctat gccccaccac gcgacttcgc agcctatcgc 1680
tccaaacggg gcagaaagaa actcctgtat atattcaaac aaccatttat gagaccagta 1740
caaactactc aagaggaaga tggctgtagc tgccgatttc cagaagaaga agaaggagga 1800
tgtgaactga gagtgaagtt cagcaggagc gcagacgccc ccgcgtacca gcagggccag 1860
aaccagctct ataacgagct caatctagga cgaagagagg agtacgatgt tttggacaag 1920
agacgtggcc gggaccctga gatgggggga aagccgagaa ggaagaaccc tcaggaaggc 1980
ctgtacaatg aactgcagaa agataagatg gcggaggcct acagtgagat tgggatgaaa 2040
ggcgagcgcc ggaggggcaa ggggcacgat ggcctttacc agggtctcag tacagccacc 2100
aaggacacct acgacgccct tcacatgcag gccctgcccc ctcgctga 2148

<210> SEQ ID NO 36
<211> LENGTH: 2154
<212> TYPE: DNA
<213> ORGANISM: Artificial Sequence
<220> FEATURE:
<223> OTHER INFORMATION: Synthetic construct

<400> SEQUENCE: 36
atgggatggt catgtatcat cctttttcta gtagcaactg caaccggtgt acattccgac 60
atccagatga cccagtctcc atcctccctg tctgcatctg taggagacag agtcaccatc 120
acttgcaagg cgagtccgga cattaatagc tatttaagct ggtttcagca gaggccaggc 180
caatctccaa ggcgcctaat ttatcgtgca aacagattgg ttgatggggt cccagacagg 240
ttcagtggca gtgggtcagg cactgatttc acactgaaaa tcagcagggt ggaggctgag 300
gatgttggag tttattactg tctacagtat gatgaatttc cgtacacgtt cggccaaggg 360
accaaggtgg aaatcaaagg ctccacctct ggatccggca agcccggatc tggcgaggga 420
tccaccaagg gcgaagtgca gctggtgcag tctggagcag aggtgaaaaa gcccggggag 480
tctctgagga tctcctgtaa gggttctgga ttcactttca gtagctatgc catgtcttgg 540
atcaggcagt ccccatcgag aggccttgag tggctgggtt ccattagtcg tggtggtacc 600
acctactatc cagacagtgt gaagggcaga ttcaccatct ccagagacaa cgccaagaac 660
tcactgtatc tgcaaatgaa cagcctgaga gccgaggaca cggctgtgta ttactgtgga 720
agatatgatt acgacgggta ctatgcaatg gactactggg gccagggaac gctggtcacc 780
gtcagctcag tcgacgagtc caaatatggt cccccatgcc caccatgccc agcacctgag 840
ttcctggggg gaccatcagt cttcctgttc cccccaaaac ccaaggacac tctcatgatc 900
tcccggaccc ctgaggtcac gtgcgtggtg gtggacgtga gccaggaaga ccccgaggtc 960
cagttcaact ggtacgtgga tggcgtggag gtgcataatg ccaagacaaa gccgcgggag 1020
gagcagttca acagcacgta ccgtgtggtc agcgtcctca ccgtcctgca ccaggactgg 1080
ctgaacggca aggagtacaa gtgcaaggtc tccaacaaag gcctcccgtc ctccatcgag 1140
aaaaccatct ccaaagccaa agggcagccc cgagagccac aggtgtacac cctgccccca 1200
tcccaggagg agatgaccaa gaaccaggtc agcctgacct gcctggtcaa aggcttctac 1260
cccagcgaca tcgccgtgga gtgggagagc aatgggcagc cggagaacaa ctacaagacc 1320
acgcctcccg tgctggactc cgacggctcc ttcttcctct acagcaggct aaccgtggac 1380
aagagcaggt ggcaggaggg gaatgtcttc tcatgctccg tgatgcatga ggctctgcac 1440
aaccactaca cacagaagag cctctccctg tccctaggta aaatgttttg ggtgctggtg 1500
gtggttggtg gagtcctggc ttgctatagc ttgctagtaa cagtggcctt tattattttc 1560
tgggtgagga gtaagaggag caggggcgga cacagtgact acatgaacat gactccccgc 1620
cgccctgggc ccacccgcaa gcattaccag ccctatgccc caccacgcga cttcgcagcc 1680
tatcgctcca aacggggcag aaagaaactc ctgtatatat tcaaacaacc atttatgaga 1740
ccagtacaaa ctactcaaga ggaagatggc tgtagctgcc gatttccaga agaagaagaa 1800
ggaggatgtg aactgagagt gaagttcagc aggagcgcag acgcccccgc gtaccagcag 1860
ggccagaacc agctctataa cgagctcaat ctaggacgaa gagaggagta cgatgttttg 1920
gacaagagac gtggccggga ccctgagatg gggggaaagc cgagaaggaa gaaccctcag 1980
gaaggcctgt acaatgaact gcagaaagat aagatggcgg aggcctacag tgagattggg 2040
atgaaaggcg agcgccggag gggcaagggg cacgatggcc tttaccaggg tctcagtaca 2100
gccaccaagg acacctacga cgcccttcac atgcaggccc tgccccctcg ctga 2154

<210> SEQ ID NO 37
<211> LENGTH: 2175
<212> TYPE: DNA
<213> ORGANISM: Artificial Sequence
<220> FEATURE:
<223> OTHER INFORMATION: Synthetic construct

<400> SEQUENCE: 37
atgggatggt catgtatcat cctttttcta gtagcaactg caaccggtgt acattccgat 60
attgtgatga cccagactcc actctccctg cccgtcaccc ctggagagcc ggcctccatc 120
tcctgcaggg caagtaagag cattagcaaa tatttagcct ggtaccagca gaaacctggc 180
caggctccca ggctcctcat ctattctgga tccactttgc aatctgggat cccacctcga 240
ttcagtggca gcgggtatgg aacagatttt accctcacaa ttaataacat agaatctgag 300
gatgctgcat attacttctg tcaacagcat gatgaatccc cgtacacgtt cggcgagggg 360
accaaggtgg aaatcaaagg tggtggtggt agcggctcca cctctggatc cggcaagccc 420
ggatctggcg agggatccac caagggcgga ggaggaggaa gtcaggtgca gctgcaggag 480
tcgggcccag gactggtgaa gccttcacag accctgtccc tcacctgcac tgtctctggt 540
tatgcattca ctgcctacaa catacactgg gtgcgacagg cccctggaca agggcttgag 600
tggatgggtt cttttgatcc ttacgatggt ggtagtagtt acaaccagaa gttcaaggac 660
agactcacca tctccaagga cacctccaaa aaccaggtgg tccttacaat gaccaacatg 720
gaccctgtgg acacagccac gtattactgt gcaagagggt ggtactactt tgactactgg 780
ggccacggaa ccctggtcac cgtctcctca gtcgacgagt ccaaatatgg tcccccatgc 840
ccaccatgcc cagcacctga gttcctgggg ggaccatcag tcttcctgtt ccccccaaaa 900
cccaaggaca ctctcatgat ctcccggacc cctgaggtca cgtgcgtggt ggtggacgtg 960
agccaggaag accccgaggt ccagttcaac tggtacgtgg atggcgtgga ggtgcataat 1020
gccaagacaa agccgcggga ggagcagttc aacagcacgt accgtgtggt cagcgtcctc 1080
accgtcctgc accaggactg gctgaacggc aaggagtaca agtgcaaggt ctccaacaaa 1140
ggcctcccgt cctccatcga gaaaaccatc tccaaagcca aagggcagcc ccgagagcca 1200
caggtgtaca ccctgccccc atcccaggag gagatgacca agaaccaggt cagcctgacc 1260
tgcctggtca aaggcttcta ccccagcgac atcgccgtgg agtgggagag caatgggcag 1320
ccggagaaca actacaagac cacgcctccc gtgctggact ccgacggctc cttcttcctc 1380
tacagcaggc taaccgtgga caagagcagg tggcaggagg ggaatgtctt ctcatgctcc 1440
gtgatgcatg aggctctgca caaccactac acacagaaga gcctctccct gtccctaggt 1500
aaaatgtttt gggtgctggt ggtggttggt ggagtcctgg cttgctatag cttgctagta 1560
acagtggcct ttattatttt ctgggtgagg agtaagagga gcaggggcgg acacagtgac 1620
tacatgaaca tgactccccg ccgccctggg cccacccgca agcattacca gccctatgcc 1680
ccaccacgcg acttcgcagc ctatcgctcc aaacggggca gaaagaaact cctgtatata 1740
ttcaaacaac catttatgag accagtacaa actactcaag aggaagatgg ctgtagctgc 1800
cgatttccag aagaagaaga aggaggatgt gaactgagag tgaagttcag caggagcgca 1860
gacgcccccg cgtaccagca gggccagaac cagctctata acgagctcaa tctaggacga 1920
agagaggagt acgatgtttt ggacaagaga cgtggccggg accctgagat ggggggaaag 1980
ccgagaagga agaaccctca ggaaggcctg tacaatgaac tgcagaaaga taagatggcg 2040
gaggcctaca gtgagattgg gatgaaaggc gagcgccgga ggggcaaggg gcacgatggc 2100
ctttaccagg gtctcagtac agccaccaag gacacctacg acgcccttca catgcaggcc 2160
ctgccccctc gctga 2175

<210> SEQ ID NO 38
<211> LENGTH: 715
<212> TYPE: PRT
<213> ORGANISM: Artificial Sequence
<220> FEATURE:
<223> OTHER INFORMATION: Synthetic construct

<400> SEQUENCE: 38

Met Gly Trp Ser Cys Ile Ile Leu Phe Leu Val Ala Thr Ala Thr Gly
1 5 10 15

Val His Ser Asp Ile Lys Met Thr Gln Ser Pro Ser Ser Met Tyr Ala
20 25 30

Ser Leu Gly Glu Arg Val Thr Ile Thr Cys Lys Ala Ser Pro Asp Ile
35 40 45

Asn Ser Tyr Leu Ser Trp Phe Gln Gln Lys Pro Gly Lys Ser Pro Lys
50 55 60

Thr Leu Ile Tyr Arg Ala Asn Arg Leu Val Asp Gly Val Pro Ser Arg
65 70 75 80

Phe Ser Gly Gly Gly Ser Gly Gln Asp Tyr Ser Leu Thr Ile Asn Ser
85 90 95

Leu Glu Tyr Glu Asp Met Gly Ile Tyr Tyr Cys Leu Gln Tyr Asp Glu
100 105 110

Phe Pro Tyr Thr Phe Gly Gly Gly Thr Lys Leu Glu Met Lys Gly Ser
115 120 125

Thr Ser Gly Ser Gly Lys Pro Gly Ser Gly Glu Gly Ser Thr Lys Gly
130 135 140

Glu Val Lys Leu Val Glu Ser Gly Gly Gly Leu Val Lys Pro Gly Gly
145 150 155 160

Ser Leu Lys Leu Ser Cys Ala Ala Ser Gly Phe Thr Phe Ser Ser Tyr
165 170 175

Ala Met Ser Trp Val Arg Gln Ile Pro Glu Lys Arg Leu Glu Trp Val
180 185 190

Ala Ser Ile Ser Arg Gly Gly Thr Thr Tyr Tyr Pro Asp Ser Val Lys
195 200 205

Gly Arg Phe Thr Ile Ser Arg Asp Asn Val Arg Asn Ile Leu Tyr Leu
210 215 220

Gln Met Ser Ser Leu Arg Ser Glu Asp Thr Ala Met Tyr Tyr Cys Gly
225 230 235 240

Arg Tyr Asp Tyr Asp Gly Tyr Tyr Ala Met Asp Tyr Trp Gly Gln Gly
245 250 255

Thr Ser Val Thr Val Ser Ser Glu Ser Lys Tyr Gly Pro Pro Cys Pro
260 265 270

Pro Cys Pro Ala Pro Glu Phe Leu Gly Gly Pro Ser Val Phe Leu Phe
275 280 285

Pro Pro Lys Pro Lys Asp Thr Leu Met Ile Ser Arg Thr Pro Glu Val
290 295 300

```
Thr Cys Val Val Val Asp Val Ser Gln Glu Asp Pro Glu Val Gln Phe
305                 310                 315                 320

Asn Trp Tyr Val Asp Gly Val Glu Val His Asn Ala Lys Thr Lys Pro
                325                 330                 335

Arg Glu Glu Gln Phe Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Gly Leu Pro Ser Ser Ile Glu Lys Thr Ile Ser Lys Ala
    370                 375                 380

Lys Gly Gln Pro Arg Glu Pro Gln Val Tyr Thr Leu Pro Pro Ser Gln
385                 390                 395                 400

Glu Glu Met Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Arg Leu Thr Val Asp Lys Ser Arg Trp Gln Glu
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Leu Gly Lys Met Phe Trp Val
                485                 490                 495

Leu Val Val Val Gly Gly Val Leu Ala Cys Tyr Ser Leu Leu Val Thr
            500                 505                 510

Val Ala Phe Ile Ile Phe Trp Val Arg Ser Lys Arg Ser Arg Gly Gly
        515                 520                 525

His Ser Asp Tyr Met Asn Met Thr Pro Arg Arg Pro Gly Pro Thr Arg
    530                 535                 540

Lys His Tyr Gln Pro Tyr Ala Pro Pro Arg Asp Phe Ala Ala Tyr Arg
545                 550                 555                 560

Ser Lys Arg Gly Arg Lys Lys Leu Leu Tyr Ile Phe Lys Gln Pro Phe
                565                 570                 575

Met Arg Pro Val Gln Thr Thr Gln Glu Glu Asp Gly Cys Ser Cys Arg
            580                 585                 590

Phe Pro Glu Glu Glu Glu Gly Gly Cys Glu Leu Arg Val Lys Phe Ser
        595                 600                 605

Arg Ser Ala Asp Ala Pro Ala Tyr Gln Gln Gly Gln Asn Gln Leu Tyr
    610                 615                 620

Asn Glu Leu Asn Leu Gly Arg Arg Glu Glu Tyr Asp Val Leu Asp Lys
625                 630                 635                 640

Arg Arg Gly Arg Asp Pro Glu Met Gly Gly Lys Pro Arg Arg Lys Asn
                645                 650                 655

Pro Gln Glu Gly Leu Tyr Asn Glu Leu Gln Lys Asp Lys Met Ala Glu
            660                 665                 670

Ala Tyr Ser Glu Ile Gly Met Lys Gly Glu Arg Arg Arg Gly Lys Gly
        675                 680                 685

His Asp Gly Leu Tyr Gln Gly Leu Ser Thr Ala Thr Lys Asp Thr Tyr
    690                 695                 700

Asp Ala Leu His Met Gln Ala Leu Pro Pro Arg
705                 710                 715
```

<210> SEQ ID NO 39
<211> LENGTH: 717
<212> TYPE: PRT
<213> ORGANISM: Artificial Sequence
<220> FEATURE:
<223> OTHER INFORMATION: Synthetic construct

<400> SEQUENCE: 39

Met Gly Trp Ser Cys Ile Ile Leu Phe Leu Val Ala Thr Ala Thr Gly
1 5 10 15

Val His Ser Asp Ile Gln Met Thr Gln Ser Pro Ser Ser Leu Ser Ala
20 25 30

Ser Val Gly Asp Arg Val Thr Ile Thr Cys Lys Ala Ser Pro Asp Ile
35 40 45

Asn Ser Tyr Leu Ser Trp Phe Gln Gln Arg Pro Gly Gln Ser Pro Arg
50 55 60

Arg Leu Ile Tyr Arg Ala Asn Arg Leu Val Asp Gly Val Pro Asp Arg
65 70 75 80

Phe Ser Gly Ser Gly Ser Gly Thr Asp Phe Thr Leu Lys Ile Ser Arg
85 90 95

Val Glu Ala Glu Asp Val Gly Val Tyr Tyr Cys Leu Gln Tyr Asp Glu
100 105 110

Phe Pro Tyr Thr Phe Gly Gln Gly Thr Lys Val Glu Ile Lys Gly Ser
115 120 125

Thr Ser Gly Ser Gly Lys Pro Gly Ser Gly Glu Gly Ser Thr Lys Gly
130 135 140

Glu Val Gln Leu Val Gln Ser Gly Ala Glu Val Lys Lys Pro Gly Glu
145 150 155 160

Ser Leu Arg Ile Ser Cys Lys Gly Ser Gly Phe Thr Phe Ser Ser Tyr
165 170 175

Ala Met Ser Trp Ile Arg Gln Ser Pro Ser Arg Gly Leu Glu Trp Leu
180 185 190

Gly Ser Ile Ser Arg Gly Gly Thr Thr Tyr Tyr Pro Asp Ser Val Lys
195 200 205

Gly Arg Phe Thr Ile Ser Arg Asp Asn Ala Lys Asn Ser Leu Tyr Leu
210 215 220

Gln Met Asn Ser Leu Arg Ala Glu Asp Thr Ala Val Tyr Tyr Cys Gly
225 230 235 240

Arg Tyr Asp Tyr Asp Gly Tyr Tyr Ala Met Asp Tyr Trp Gly Gln Gly
245 250 255

Thr Leu Val Thr Val Ser Ser Val Asp Glu Ser Lys Tyr Gly Pro Pro
260 265 270

Cys Pro Pro Cys Pro Ala Pro Glu Phe Leu Gly Gly Pro Ser Val Phe
275 280 285

Leu Phe Pro Pro Lys Pro Lys Asp Thr Leu Met Ile Ser Arg Thr Pro
290 295 300

Glu Val Thr Cys Val Val Val Asp Val Ser Gln Glu Asp Pro Glu Val
305 310 315 320

Gln Phe Asn Trp Tyr Val Asp Gly Val Glu Val His Asn Ala Lys Thr
325 330 335

Lys Pro Arg Glu Glu Gln Phe Asn Ser Thr Tyr Arg Val Val Ser Val
340 345 350

Leu Thr Val Leu His Gln Asp Trp Leu Asn Gly Lys Glu Tyr Lys Cys
355 360 365

```
Lys Val Ser Asn Lys Gly Leu Pro Ser Ser Ile Glu Lys Thr Ile Ser
    370                 375                 380

Lys Ala Lys Gly Gln Pro Arg Glu Pro Gln Val Tyr Thr Leu Pro Pro
385                 390                 395                 400

Ser Gln Glu Glu Met Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
            420                 425                 430

Gln Pro Glu Asn Asn Tyr Lys Thr Thr Pro Pro Val Leu Asp Ser Asp
        435                 440                 445

Gly Ser Phe Phe Leu Tyr Ser Arg Leu Thr Val Asp Lys Ser Arg Trp
    450                 455                 460

Gln Glu Gly Asn Val Phe Ser Cys Ser Val Met His Glu Ala Leu His
465                 470                 475                 480

Asn His Tyr Thr Gln Lys Ser Leu Ser Leu Ser Leu Gly Lys Met Phe
                485                 490                 495

Trp Val Leu Val Val Val Gly Gly Val Leu Ala Cys Tyr Ser Leu Leu
            500                 505                 510

Val Thr Val Ala Phe Ile Ile Phe Trp Val Arg Ser Lys Arg Ser Arg
        515                 520                 525

Gly Gly His Ser Asp Tyr Met Asn Met Thr Pro Arg Arg Pro Gly Pro
    530                 535                 540

Thr Arg Lys His Tyr Gln Pro Tyr Ala Pro Pro Arg Asp Phe Ala Ala
545                 550                 555                 560

Tyr Arg Ser Lys Arg Gly Arg Lys Lys Leu Leu Tyr Ile Phe Lys Gln
                565                 570                 575

Pro Phe Met Arg Pro Val Gln Thr Thr Gln Glu Glu Asp Gly Cys Ser
            580                 585                 590

Cys Arg Phe Pro Glu Glu Glu Glu Gly Gly Cys Glu Leu Arg Val Lys
        595                 600                 605

Phe Ser Arg Ser Ala Asp Ala Pro Ala Tyr Gln Gln Gly Gln Asn Gln
    610                 615                 620

Leu Tyr Asn Glu Leu Asn Leu Gly Arg Arg Glu Glu Tyr Asp Val Leu
625                 630                 635                 640

Asp Lys Arg Arg Gly Arg Asp Pro Glu Met Gly Gly Lys Pro Arg Arg
                645                 650                 655

Lys Asn Pro Gln Glu Gly Leu Tyr Asn Glu Leu Gln Lys Asp Lys Met
            660                 665                 670

Ala Glu Ala Tyr Ser Glu Ile Gly Met Lys Gly Glu Arg Arg Arg Gly
        675                 680                 685

Lys Gly His Asp Gly Leu Tyr Gln Gly Leu Ser Thr Ala Thr Lys Asp
    690                 695                 700

Thr Tyr Asp Ala Leu His Met Gln Ala Leu Pro Pro Arg
705                 710                 715


<210> SEQ ID NO 40
<211> LENGTH: 724
<212> TYPE: PRT
<213> ORGANISM: Artificial Sequence
<220> FEATURE:
<223> OTHER INFORMATION: Synthetic construct

<400> SEQUENCE: 40

Met Gly Trp Ser Cys Ile Ile Leu Phe Leu Val Ala Thr Ala Thr Gly
1               5                   10                  15
```

```
Val His Ser Asp Ile Val Met Thr Gln Thr Pro Leu Ser Leu Pro Val
            20                  25                  30

Thr Pro Gly Glu Pro Ala Ser Ile Ser Cys Arg Ala Ser Lys Ser Ile
        35                  40                  45

Ser Lys Tyr Leu Ala Trp Tyr Gln Gln Lys Pro Gly Gln Ala Pro Arg
    50                  55                  60

Leu Leu Ile Tyr Ser Gly Ser Thr Leu Gln Ser Gly Ile Pro Pro Arg
65                  70                  75                  80

Phe Ser Gly Ser Gly Tyr Gly Thr Asp Phe Thr Leu Thr Ile Asn Asn
                85                  90                  95

Ile Glu Ser Glu Asp Ala Ala Tyr Tyr Phe Cys Gln Gln His Asp Glu
            100                 105                 110

Ser Pro Tyr Thr Phe Gly Glu Gly Thr Lys Val Glu Ile Lys Gly Gly
        115                 120                 125

Gly Gly Ser Gly Ser Thr Ser Gly Ser Gly Lys Pro Gly Ser Gly Glu
    130                 135                 140

Gly Ser Thr Lys Gly Gly Gly Gly Gly Ser Gln Val Gln Leu Gln Glu
145                 150                 155                 160

Ser Gly Pro Gly Leu Val Lys Pro Ser Gln Thr Leu Ser Leu Thr Cys
                165                 170                 175

Thr Val Ser Gly Tyr Ala Phe Thr Ala Tyr Asn Ile His Trp Val Arg
            180                 185                 190

Gln Ala Pro Gly Gln Gly Leu Glu Trp Met Gly Ser Phe Asp Pro Tyr
        195                 200                 205

Asp Gly Gly Ser Ser Tyr Asn Gln Lys Phe Lys Asp Arg Leu Thr Ile
    210                 215                 220

Ser Lys Asp Thr Ser Lys Asn Gln Val Val Leu Thr Met Thr Asn Met
225                 230                 235                 240

Asp Pro Val Asp Thr Ala Thr Tyr Tyr Cys Ala Arg Gly Trp Tyr Tyr
                245                 250                 255

Phe Asp Tyr Trp Gly His Gly Thr Leu Val Thr Val Ser Ser Val Asp
            260                 265                 270

Glu Ser Lys Tyr Gly Pro Pro Cys Pro Pro Cys Pro Ala Pro Glu Phe
        275                 280                 285

Leu Gly Gly Pro Ser Val Phe Leu Phe Pro Pro Lys Pro Lys Asp Thr
    290                 295                 300

Leu Met Ile Ser Arg Thr Pro Glu Val Thr Cys Val Val Val Asp Val
305                 310                 315                 320

Ser Gln Glu Asp Pro Glu Val Gln Phe Asn Trp Tyr Val Asp Gly Val
                325                 330                 335

Glu Val His Asn Ala Lys Thr Lys Pro Arg Glu Glu Gln Phe Asn Ser
            340                 345                 350

Thr Tyr Arg Val Val Ser Val Leu Thr Val Leu His Gln Asp Trp Leu
        355                 360                 365

Asn Gly Lys Glu Tyr Lys Cys Lys Val Ser Asn Lys Gly Leu Pro Ser
    370                 375                 380

Ser Ile Glu Lys Thr Ile Ser Lys Ala Lys Gly Gln Pro Arg Glu Pro
385                 390                 395                 400

Gln Val Tyr Thr Leu Pro Pro Ser Gln Glu Glu Met Thr Lys Asn Gln
                405                 410                 415

Val Ser Leu Thr Cys Leu Val Lys Gly Phe Tyr Pro Ser Asp Ile Ala
            420                 425                 430

Val Glu Trp Glu Ser Asn Gly Gln Pro Glu Asn Asn Tyr Lys Thr Thr
```

```
        435                 440                 445

Pro Pro Val Leu Asp Ser Asp Gly Ser Phe Phe Leu Tyr Ser Arg Leu
    450                 455                 460

Thr Val Asp Lys Ser Arg Trp Gln Glu Gly Asn Val Phe Ser Cys Ser
465                 470                 475                 480

Val Met His Glu Ala Leu His Asn His Tyr Thr Gln Lys Ser Leu Ser
                485                 490                 495

Leu Ser Leu Gly Lys Met Phe Trp Val Leu Val Val Val Gly Gly Val
            500                 505                 510

Leu Ala Cys Tyr Ser Leu Leu Val Thr Val Ala Phe Ile Ile Phe Trp
        515                 520                 525

Val Arg Ser Lys Arg Ser Arg Gly Gly His Ser Asp Tyr Met Asn Met
    530                 535                 540

Thr Pro Arg Arg Pro Gly Pro Thr Arg Lys His Tyr Gln Pro Tyr Ala
545                 550                 555                 560

Pro Pro Arg Asp Phe Ala Ala Tyr Arg Ser Lys Arg Gly Arg Lys Lys
                565                 570                 575

Leu Leu Tyr Ile Phe Lys Gln Pro Phe Met Arg Pro Val Gln Thr Thr
            580                 585                 590

Gln Glu Glu Asp Gly Cys Ser Cys Arg Phe Pro Glu Glu Glu Glu Gly
        595                 600                 605

Gly Cys Glu Leu Arg Val Lys Phe Ser Arg Ser Ala Asp Ala Pro Ala
    610                 615                 620

Tyr Gln Gln Gly Gln Asn Gln Leu Tyr Asn Glu Leu Asn Leu Gly Arg
625                 630                 635                 640

Arg Glu Glu Tyr Asp Val Leu Asp Lys Arg Arg Gly Arg Asp Pro Glu
                645                 650                 655

Met Gly Gly Lys Pro Arg Arg Lys Asn Pro Gln Glu Gly Leu Tyr Asn
            660                 665                 670

Glu Leu Gln Lys Asp Lys Met Ala Glu Ala Tyr Ser Glu Ile Gly Met
        675                 680                 685

Lys Gly Glu Arg Arg Arg Gly Lys Gly His Asp Gly Leu Tyr Gln Gly
    690                 695                 700

Leu Ser Thr Ala Thr Lys Asp Thr Tyr Asp Ala Leu His Met Gln Ala
705                 710                 715                 720

Leu Pro Pro Arg


<210> SEQ ID NO 41
<211> LENGTH: 111
<212> TYPE: PRT
<213> ORGANISM: Artificial Sequence
<220> FEATURE:
<223> OTHER INFORMATION: Synthetic construct

<400> SEQUENCE: 41

Val Asp Glu Ser Lys Tyr Gly Pro Pro Cys Pro Pro Cys Pro Leu Pro
1               5                   10                  15

Pro Ser Gln Glu Glu Met Thr Lys Asn Gln Val Ser Leu Thr Cys Leu
            20                  25                  30

Val Lys Gly Phe Tyr Pro Ser Asp Ile Ala Val Glu Trp Glu Ser Asn
        35                  40                  45

Gly Gln Pro Glu Asn Asn Tyr Lys Thr Thr Pro Pro Val Leu Asp Ser
    50                  55                  60

Asp Gly Ser Phe Phe Leu Tyr Ser Arg Leu Thr Val Asp Lys Ser Arg
65                  70                  75                  80
```

```
Trp Gln Glu Gly Asn Val Phe Ser Cys Ser Val Met His Glu Ala Leu
                85                  90                  95

His Asn His Tyr Thr Gln Lys Ser Leu Ser Leu Ser Leu Gly Lys
            100                 105                 110


<210> SEQ ID NO 42
<211> LENGTH: 231
<212> TYPE: PRT
<213> ORGANISM: Artificial Sequence
<220> FEATURE:
<223> OTHER INFORMATION: Synthetic construct

<400> SEQUENCE: 42

Val Asp Glu Ser Lys Tyr Gly Pro Pro Cys Pro Pro Cys Pro Ala Pro
1               5                   10                  15

Glu Phe Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser Gln Glu Asp Pro Glu Val Gln Phe Asn Trp Tyr Val Asp
    50                  55                  60

Gly Val Glu Val His Asn Ala Lys Thr Lys Pro Arg Glu Glu Gln Phe
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Gly Leu
            100                 105                 110

Pro Ser Ser Ile Glu Lys Thr Ile Ser Lys Ala Lys Gly Gln Pro Arg
        115                 120                 125

Glu Pro Gln Val Tyr Thr Leu Pro Pro Ser Gln Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Arg Leu Thr Val Asp Lys Ser Arg Trp Gln Glu Gly Asn Val Phe Ser
        195                 200                 205

Cys Ser Val Met His Glu Ala Leu His Asn His Tyr Thr Gln Lys Ser
    210                 215                 220

Leu Ser Leu Ser Leu Gly Lys
225                 230


<210> SEQ ID NO 43
<211> LENGTH: 6
<212> TYPE: PRT
<213> ORGANISM: Artificial Sequence
<220> FEATURE:
<223> OTHER INFORMATION: Synthetic construct

<400> SEQUENCE: 43

Lys Ser Ile Ser Lys Tyr
1               5


<210> SEQ ID NO 44
<211> LENGTH: 3
<212> TYPE: PRT
```

<213> ORGANISM: Artificial Sequence
<220> FEATURE:
<223> OTHER INFORMATION: Synthetic construct

<400> SEQUENCE: 44

Ser Gly Ser
1

<210> SEQ ID NO 45
<211> LENGTH: 8
<212> TYPE: PRT
<213> ORGANISM: Artificial Sequence
<220> FEATURE:
<223> OTHER INFORMATION: Synthetic construct

<400> SEQUENCE: 45

Gln Gln His Asp Glu Ser Pro Tyr
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic construct

<400> SEQUENCE: 46

Gly Tyr Ala Phe Thr Ala Tyr Asn
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic construct

<400> SEQUENCE: 47

Phe Asp Pro Tyr Asp Gly Gly Ser
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic construct

<400> SEQUENCE: 48

Gly Trp Tyr Tyr Phe Asp Tyr
1               5

<210> SEQ ID NO 49
<211> LENGTH: 6
<212> TYPE: PRT
<213> ORGANISM: Artificial Sequence
<220> FEATURE:
<223> OTHER INFORMATION: Synthetic construct

<400> SEQUENCE: 49

Pro Asp Ile Asn Ser Tyr
1               5

<210> SEQ ID NO 50
<211> LENGTH: 3
<212> TYPE: PRT
<213> ORGANISM: Artificial Sequence
<220> FEATURE:
<223> OTHER INFORMATION: Synthetic construct

<400> SEQUENCE: 50

Arg Ala Asn
1

<210> SEQ ID NO 51
<211> LENGTH: 9
<212> TYPE: PRT
<213> ORGANISM: Artificial Sequence
<220> FEATURE:
<223> OTHER INFORMATION: Synthetic construct

<400> SEQUENCE: 51

Leu Gln Tyr Asp Glu Phe Pro Tyr Thr
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic construct

<400> SEQUENCE: 52

Gly Phe Thr Phe Ser Ser Tyr Ala
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic construct

<400> SEQUENCE: 53

Ile Ser Arg Gly Gly Thr Thr
1               5

<210> SEQ ID NO 54
<211> LENGTH: 11
<212> TYPE: PRT
<213> ORGANISM: Artificial Sequence
<220> FEATURE:
<223> OTHER INFORMATION: Synthetic construct

<400> SEQUENCE: 54

Tyr Asp Tyr Asp Gly Tyr Tyr Ala Met Asp Tyr
1               5                   10

<210> SEQ ID NO 55
<211> LENGTH: 937
<212> TYPE: PRT
<213> ORGANISM: Homo sapiens

<400> SEQUENCE: 55

Met His Arg Pro Arg Arg Arg Gly Thr Arg Pro Pro Leu Leu Ala Leu
1               5                   10                  15

Leu Ala Ala Leu Leu Leu Ala Ala Arg Gly Ala Ala Ala Gln Glu Thr
            20                  25                  30

Glu Leu Ser Val Ser Ala Glu Leu Val Pro Thr Ser Ser Trp Asn Ile
        35                  40                  45

Ser Ser Glu Leu Asn Lys Asp Ser Tyr Leu Thr Leu Asp Glu Pro Met
    50                  55                  60

-continued

```
Asn Asn Ile Thr Thr Ser Leu Gly Gln Thr Ala Glu Leu His Cys Lys
65                  70                  75                  80

Val Ser Gly Asn Pro Pro Pro Thr Ile Arg Trp Phe Lys Asn Asp Ala
                85                  90                  95

Pro Val Val Gln Glu Pro Arg Arg Leu Ser Phe Arg Ser Thr Ile Tyr
            100                 105                 110

Gly Ser Arg Leu Arg Ile Arg Asn Leu Asp Thr Thr Asp Thr Gly Tyr
        115                 120                 125

Phe Gln Cys Val Ala Thr Asn Gly Lys Glu Val Val Ser Ser Thr Gly
    130                 135                 140

Val Leu Phe Val Lys Phe Gly Pro Pro Pro Thr Ala Ser Pro Gly Tyr
145                 150                 155                 160

Ser Asp Glu Tyr Glu Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
            180                 185                 190

His Met Gln Gly Glu Ile Glu Asn Gln Ile Thr Ala Ala Phe Thr Met
        195                 200                 205

Ile Gly Thr Ser Ser His Leu Ser Asp Lys Cys Ser Gln Phe Ala Ile
    210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Ile Leu Glu
                245                 250                 255

Asn Val Leu Cys Gln Thr Glu Tyr Ile Phe Ala Arg Ser Asn Pro Met
            260                 265                 270

Ile Leu Met Arg Leu Lys Leu Pro Asn Cys Glu Asp Leu Pro Gln Pro
        275                 280                 285

Glu Ser Pro Glu Ala Ala Asn Cys Ile Arg Ile Gly Ile Pro Met Ala
    290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
                325                 330                 335

Trp Asn Ser Gln Tyr Pro His Thr His Thr Phe Thr Ala Leu Arg Phe
            340                 345                 350

Pro Glu Leu Asn Gly Gly His Ser Tyr Cys Arg Asn Pro Gly Asn Gln
        355                 360                 365

Lys Glu Ala Pro Trp Cys Phe Thr Leu Asp Glu Asn Phe Lys Ser Asp
    370                 375                 380

Leu Cys Asp Ile Pro Ala Cys Asp Ser Lys Asp Ser Lys Glu Lys Asn
385                 390                 395                 400

Lys Met Glu Ile Leu Tyr Ile Leu Val Pro Ser Val Ala Ile Pro Leu
                405                 410                 415

Ala Ile Ala Leu Leu Phe Phe Phe Ile Cys Val Cys Arg Asn Asn Gln
            420                 425                 430

Lys Ser Ser Ser Ala Pro Val Gln Arg Gln Pro Lys His Val Arg Gly
        435                 440                 445

Gln Asn Val Glu Met Ser Met Leu Asn Ala Tyr Lys Pro Lys Ser Lys
    450                 455                 460

Ala Lys Glu Leu Pro Leu Ser Ala Val Arg Phe Met Glu Glu Leu Gly
465                 470                 475                 480
```

-continued

```
Glu Cys Ala Phe Gly Lys Ile Tyr Lys Gly His Leu Tyr Leu Pro Gly
                485                 490                 495

Met Asp His Ala Gln Leu Val Ala Ile Lys Thr Leu Lys Asp Tyr Asn
            500                 505                 510

Asn Pro Gln Gln Trp Met Glu Phe Gln Gln Glu Ala Ser Leu Met Ala
        515                 520                 525

Glu Leu His His Pro Asn Ile Val Cys Leu Leu Gly Ala Val Thr Gln
    530                 535                 540

Glu Gln Pro Val Cys Met Leu Phe Glu Tyr Ile Asn Gln Gly Asp Leu
545                 550                 555                 560

His Glu Phe Leu Ile Met Arg Ser Pro His Ser Asp Val Gly Cys Ser
                565                 570                 575

Ser Asp Glu Asp Gly Thr Val Lys Ser Ser Leu Asp His Gly Asp Phe
            580                 585                 590

Leu His Ile Ala Ile Gln Ile Ala Ala Gly Met Glu Tyr Leu Ser Ser
        595                 600                 605

His Phe Phe Val His Lys Asp Leu Ala Ala Arg Asn Ile Leu Ile Gly
    610                 615                 620

Glu Gln Leu His Val Lys Ile Ser Asp Leu Gly Leu Ser Arg Glu Ile
625                 630                 635                 640

Tyr Ser Ala Asp Tyr Tyr Arg Val Gln Ser Lys Ser Leu Leu Pro Ile
                645                 650                 655

Arg Trp Met Pro Pro Glu Ala Ile Met Tyr Gly Lys Phe Ser Ser Asp
            660                 665                 670

Ser Asp Ile Trp Ser Phe Gly Val Val Leu Trp Glu Ile Phe Ser Phe
        675                 680                 685

Gly Leu Gln Pro Tyr Tyr Gly Phe Ser Asn Gln Glu Val Ile Glu Met
    690                 695                 700

Val Arg Lys Arg Gln Leu Leu Pro Cys Ser Glu Asp Cys Pro Pro Arg
705                 710                 715                 720

Met Tyr Ser Leu Met Thr Glu Cys Trp Asn Glu Ile Pro Ser Arg Arg
                725                 730                 735

Pro Arg Phe Lys Asp Ile His Val Arg Leu Arg Ser Trp Glu Gly Leu
            740                 745                 750

Ser Ser His Thr Ser Ser Thr Thr Pro Ser Gly Gly Asn Ala Thr Thr
        755                 760                 765

Gln Thr Thr Ser Leu Ser Ala Ser Pro Val Ser Asn Leu Ser Asn Pro
    770                 775                 780

Arg Tyr Pro Asn Tyr Met Phe Pro Ser Gln Gly Ile Thr Pro Gln Gly
785                 790                 795                 800

Gln Ile Ala Gly Phe Ile Gly Pro Pro Ile Pro Gln Asn Gln Arg Phe
                805                 810                 815

Ile Pro Ile Asn Gly Tyr Pro Ile Pro Pro Gly Tyr Ala Ala Phe Pro
            820                 825                 830

Ala Ala His Tyr Gln Pro Thr Gly Pro Pro Arg Val Ile Gln His Cys
        835                 840                 845

Pro Pro Pro Lys Ser Arg Ser Pro Ser Ser Ala Ser Gly Ser Thr Ser
    850                 855                 860

Thr Gly His Val Thr Ser Leu Pro Ser Ser Gly Ser Asn Gln Glu Ala
865                 870                 875                 880

Asn Ile Pro Leu Leu Pro His Met Ser Ile Pro Asn His Pro Gly Gly
                885                 890                 895

Met Gly Ile Thr Val Phe Gly Asn Lys Ser Gln Lys Pro Tyr Lys Ile
```

-continued

```
        900                 905                 910

Asp Ser Lys Gln Ala Ser Leu Leu Gly Asp Ala Asn Ile His Gly His
        915                 920                 925

Thr Glu Ser Met Ile Ser Ala Glu Leu
    930                 935


<210> SEQ ID NO 56
<211> LENGTH: 21
<212> TYPE: PRT
<213> ORGANISM: Homo sapiens

<400> SEQUENCE: 56

Val Ala Thr Asn Gly Lys Glu Val Val Ser Ser Thr Gly Val Leu Phe
1               5                   10                  15

Val Lys Phe Gly Pro
            20


<210> SEQ ID NO 57
<211> LENGTH: 15
<212> TYPE: PRT
<213> ORGANISM: Homo sapiens

<400> SEQUENCE: 57

Glu Val Val Ser Ser Thr Gly Val Leu Phe Val Lys Phe Gly Pro
1               5                   10                  15
```